US007750123B2

(12) United States Patent
Marasco et al.

(10) Patent No.: US 7,750,123 B2
(45) Date of Patent: Jul. 6, 2010

(54) ANTIBODIES AGAINST SARS-COV AND METHODS OF USE THEREOF

(75) Inventors: Wayne Marasco, Wellesley, MA (US); Jianhua Sui, Boston, MA (US)

(73) Assignee: Dana Farber Cancer Institute, Inc., Boston, MA (US)

( * ) Notice: Subject to any disclaimer, the term of this patent is extended or adjusted under 35 U.S.C. 154(b) by 1058 days.

(21) Appl. No.: 10/997,201

(22) Filed: Nov. 24, 2004

(65) Prior Publication Data

US 2005/0249739 A1 Nov. 10, 2005

Related U.S. Application Data

(60) Provisional application No. 60/524,840, filed on Nov. 25, 2003.

(51) Int. Cl.
*C12P 21/08* (2006.01)
*G01N 33/563* (2006.01)
*A61K 39/395* (2006.01)
*A61K 39/00* (2006.01)

(52) U.S. Cl. .............. 530/387.3; 530/388.1; 530/388.8; 436/512; 424/130.1; 424/136.1

(58) Field of Classification Search ................ None
See application file for complete search history.

(56) References Cited

U.S. PATENT DOCUMENTS

| | | | | |
|---|---|---|---|---|
| 3,773,919 | A | 11/1973 | Boswell et al. ............... 424/19 |
| 4,485,045 | A | 11/1984 | Regen ......................... 260/403 |
| 4,522,811 | A | 6/1985 | Eppstein et al. ............... 514/2 |
| 4,544,545 | A | 10/1985 | Ryan et al. ................... 424/1.1 |
| 4,676,980 | A | 6/1987 | Segal et al. ..................... 424/85 |
| 4,816,567 | A | 3/1989 | Cabilly et al. ............... 530/387 |
| 4,946,778 | A | 8/1990 | Ladner et al. ............... 435/69.6 |
| 5,013,556 | A | 5/1991 | Woodle et al. ............... 424/450 |
| 5,030,719 | A | 7/1991 | Umemoto et al. ........... 530/391 |
| 5,091,513 | A | 2/1992 | Huston et al. ............... 530/387 |
| 5,132,405 | A | 7/1992 | Huston et al. ............. 530/387.3 |
| 5,223,409 | A | 6/1993 | Ladner et al. ............... 435/69.7 |
| 5,233,409 | A | 8/1993 | Schwab ....................... 356/402 |
| 5,290,540 | A | 3/1994 | Prince et al. ................... 424/45 |
| 5,545,806 | A | 8/1996 | Lonberg et al. ................ 800/2 |
| 5,545,807 | A | 8/1996 | Surani et al. ..................... 800/2 |
| 5,569,825 | A | 10/1996 | Lonberg et al. ................ 800/2 |
| 5,625,126 | A | 4/1997 | Lonberg et al. ................ 800/2 |
| 5,633,425 | A | 5/1997 | Lonberg et al. ................ 800/2 |
| 5,661,016 | A | 8/1997 | Lonberg et al. ........... 435/172.3 |
| 5,707,626 | A | 1/1998 | Douvas et al. ............. 424/100.1 |
| 5,736,137 | A * | 4/1998 | Anderson et al. ......... 424/133.1 |
| 5,762,905 | A | 6/1998 | Burton et al. ............... 424/1.49 |
| 5,824,307 | A | 10/1998 | Johnson .................... 424/133.1 |
| 5,916,771 | A | 6/1999 | Hori et al. .................. 435/69.6 |
| 5,939,068 | A | 8/1999 | Brams et al. .............. 424/133.1 |
| 5,939,598 | A | 8/1999 | Kucherlapati et al. ......... 800/25 |
| 6,063,905 | A | 5/2000 | Capra et al. ............... 530/387.3 |
| 6,156,313 | A | 12/2000 | Burton et al. ............. 424/147.1 |
| 6,261,558 | B1 | 7/2001 | Barbas et al. ............. 424/133.1 |
| RE37,525 | E | 1/2002 | Prince et al. .................... 424/45 |
| 6,538,114 | B1 | 3/2003 | Persson et al. ............ 530/388.3 |
| RE38,071 | E | 4/2003 | Prince et al. .................... 424/45 |
| 2005/0069869 | A1 * | 3/2005 | Ambrosino et al. ............ 435/5 |
| 2005/0113298 | A1 * | 5/2005 | Farzan et al. .................. 514/12 |

FOREIGN PATENT DOCUMENTS

| | | |
|---|---|---|
| EP | 0 003 089 A1 | 7/1979 |
| WO | WO 91/00360 | 1/1991 |
| WO | WO 94/02602 | 2/1994 |
| WO | WO 94/11026 | 5/1994 |
| WO | WO 95/22618 | 8/1995 |
| WO | WO 96/33735 | 10/1996 |
| WO | WO 96/34096 | 10/1996 |
| WO | WO 99/53049 | 10/1999 |
| WO | WO 2004/085650 A1 | 10/2004 |
| WO | WO 2005/027963 A2 | 3/2005 |

OTHER PUBLICATIONS

Kashmiri S. et al. :SDR grafting—a new approach to antibody humanization Methods, 36 (2005) 25-34.*
Tamura M. et al. "Structural Correlates of an Anticarcinoma Antibody: Identification of Specificity-Determining Residues (SDRs) and Development of a Minimally Immunogenic Antibody Variant by Retention of SDRs Only". J. Immunology, 164 (2000):1432-1441.*
Keller et al. "Passive immunity in prevention and treatment of infectious diseases". Clin Microbiol Rev. Oct. 2000;13(4):602-14. Cited as ref 15 in IDS.*
Yoo D et al "A single amino acid change within antigenic domain II of the spike protein of bovine coronavirus confers resistance to virus neutralization". Clin Diagn Lab Immunol. 2001, 8(2)::297-302. Cited as Ref #113 in IDS.*
Cavanagh D. "Severer acute respiratory syndrome vaccine development: experience of vaccination against avain infectious bronchitis coronavirus" Avian Pathology, 32(6):567-582.*

(Continued)

*Primary Examiner*—Bo Peng
(74) *Attorney, Agent, or Firm*—Mintz, Levin, Cohen, Ferris, Glovsky and Popeo P.C.; Ivor R. Elrifi; Cynthia A. Kozakiewicz

(57) ABSTRACT

The invention provides scFv antibodies and monoclonal antibodies that neutralize SARS-CoV. Also provided are methods of treating and/or preventing a coronavirus-related disease or disorder such as SARS. The invention also provides methods of vaccinating a patient against SARS-CoV. Also provided are methods of diagnosing coronavirus-related diseases or disorders and methods of detecting the presence of a coronavirus in a sample. The invention additionally provides methods of screening for compounds that modulate the binding of SARS-CoV and the SARS-CoV receptor ACE2 as well as for compounds useful to treat SARS-CoV-related diseases or disorders.

4 Claims, 11 Drawing Sheets

OTHER PUBLICATIONS

Weiss SR et al. "Coronavirus pathogenesis and the emerging pathogen severe acute respiratory syndrome coronavirus" Microbiol Mol Biol Rev. 2005; 69(4):635-64.*

Bost K. et al. Antibodies against peptides sequence within the HIV envelope protein crossreact with human interleukin-2 Immunological Investigations, 17(6&7):577-586, 1988.*

Illustrated Dictionary of Immunology (1995, CRC Press, Inc. Boca Raton FL; JM Cruse and RE Lewis eds), pp. 18, 19, 22, 23, 102 and 103.*

International Search Report for PCT/US2004/039750, mailed Sep. 7, 2005.

Bai et al., "Inhibition of tat-mediated transactivation and HIV-1 replication by human anti-hCyclinT1 Intrabodies", *J. Biol. Chem.*, 278(3):1433-1442 (2003).

Barbas III et al., "Recombinant human Fab fragments neutralize human type 1 immunodeficiency virus in vitro", *Proc. Natl. Acad. Sci. USA*, 89:9339-9343 (1992).

Barnett et al., "Antibody production in Chinese hamster ovary cells using an impaired selectable marker", *Antibody Expression and Engineering*, Chapter 3, pp. 27-40 (1995).

Bobo et al., "Convection-enhanced delivery of macromolecules in the brain", *Proc. Natl. Acad. Sci. USA*, 91:2076-2080 (1994).

Bona et al., "Toward development of T-cell vaccines", *Immunol. Today*, 19(3):126-133 (1998).

Burton, D.R., "Antibodies, viruses and vaccines", *Nat. Rev. Immunol.*, 2(9):706-713 (2002).

Caron et al., "Engineered humanized dimeric forms of IgG are more effective antibodies", *J. Exp. Med.*, 176:1191-1195 (1992).

Carell et al., "A novel procedure for the synthesis of libraries containing small organic molecules", *Angew. Chem. Int. Ed. Engl.*, 33(20):2059-2061 (1994).

Carter, P., "Bispecific human IgG by design", *J. Immunol. Meth.*, 248(1-2):7-15 (2001).

Casadevall, A., "Antibodies for defense against biological attack", *Nat. Biotechnol.*, 20(2):114 (2002).

Casares et al., "Protective immunity elicited by vaccination with DNA encoding for a B cell and a T cell epitope of the A/PR/8/34 influenza virus", *Viral Immunol.*, 10(3):129-136 (1997).

Chinese SARS Molecular Epidemiology Consortium, "Molecular evolution of the SARS coronavirus during the course of the SARS epidemic in China", *Science*, 303(5664):1666-1669 (2004).

Cho et al., "An unnatural biopolymer", *Science*, 261:1303-1305 (1993).

Corapi et al., "Localization of antigenic sites of the S glycoprotein of feline infectious peritonitis virus involved in neutralization and antibody-dependent enhancement", *J. Virol.*, 69(5):2858-2862 (1995).

Cull et al., "Screening for receptor ligands using large libraries of peptides linked to the C terminus of the *lac* repressor", *Proc. Natl. Acad. Sci. USA*, 89:1865-1869 (1992).

Cwirla et al., "Peptides on phage: a vast library of peptides for indentifying ligands", *Proc. Natl. Acad. Sci. USA*, 87:6378-6382 (1990).

Davidson et al., "A model system for in vivo gene transfer into the central nervous system using an adenoviral vector", *Nat. Genet.*, 3(3):219-223 (1993).

Davies et al., "Antibody-antigen complexes, *Ann. Rev. Biochem.*, 59:439-473 (1990).

De Groot, A.S., "How the SARS vaccine effort can learn from HIV—speeding towards the future, learning from the past", *Vaccine*, 21:4095-4104 (2003).

Devlin et al., "Random peptide libraries: a source of specific protein binding molecules", *Science*, 249:404-406 (1990).

DeWitt et al., "Diversomers': an approach to nonpeptide, nonoligomeric chemical diversity", *Proc. Natl. Acad. Sci. USA*, 90:6909-6913 (1993).

Enshell-Seijffers et al., "The mapping and reconstitution of a conformational discontinuous B-cell Epitope of HIV-1", *J. Mol. Biol.*, 334(1):87-101 (2003).

Erb et al., "Recursive deconvolution of combinatorial chemical libraries", *Proc. Natl. Acad. Sci. USA*, 91:11422-11426 (1994).

Felici, F., "Selection of antibody ligands from a large library of oligopeptides expressed on a multivalent exposition vector", *J. Mol. Biol.*, 222(2):301-310 (1991).

Fishwild et al., "High-avidity human IgGκ monoclonal antibodies from a novel strain of minilocus transgenic mice", *Nat. Biotechnol.*, 14(7):845-851 (1996).

Fodor et al., "multiplexed biochemical assays with biological chips", *Nature*, 364(6437):555-556 (1993).

Fouchier et al., "Koch's postulates fulfilled for SARS virus", *Nature*, 423:240 (2003).

Gallagher et al., "Coronavirus spike proteins in viral entry and pathogenesis", *Virol.*, 279(2):371-374 (2001).

Gallop et al., "Applications of combinatorial technologies to drug discovery. 1. Background and peptide combinatorial libraries", *J. Med. Chem.*, 37(9):1233-1251 (1994).

Garrity et al., "Refocusing neutralizing antibody response by targeted dampening of an immunodominant Epitope", *J. Immunol.*, 159:279-289 (1997).

Gauduin et al., "Immunization with live attenuated simian immunodeficiency virus induces strong type 1 T helper responses and β-chemokine production", *Proc. Natl. Acad. Sci. USA*, 96(24):14031-14036 (1999).

Geller et al., "Infection of cultured central nervous system neurons with a defective herpes simplex virus 1 vector results in stable expression of *Escherichia coli* β-galactosidase", *Proc. Natl. Acad. Sci. USA*, 87:1149-1153 (1990).

Geller et al., "Long-term increases in neurotransmitter release from neuronal cells expressing a consitutively active adenylate cyclase from a herpes simplex virus type 1 vector", *Proc. Natl. Acad. Sci. USA*, 90:7603-7607 (1993).

Geller et al., "An HSV-1 vector expressing tyrosine hydroxylase causes production and release of $_L$-DOPA from cultured rat striatal cells", *J. Neurochem.*, 64:487-496 (1995).

GenBank Accession No. AY274119, Mar. 2004.

GenBank Accession No. AY525636, Feb. 2005.

GenBank Accession No. AY304486, Nov. 2003.

Gerloni et al., "Immunity to *Plasmodium falciparum* malaria sporozoites by somatic transgene immunization", *Nat. Biotechnol.*, 15(9):876-881 (1997).

Gerloni et al., "Somatic transgene immunization with DNS encoding an immunoglobulin heavy chain", *DNA Cell Biol.*, 16(5):611-625 (1997).

Godet et al., "Major receptor-binding and neutralization determinants are located within the same domain of the transmissible gastroenteritis virus (coronavirus) spike protein", *J. Virol.*, 68(12):8008-8016 (1994).

Guan et al., "Isolation and characterization of viruses related to the SARS coronavirus from animals in southern China", *Science*, 302:276-278 (2003).

Guo et al., "SARS corona virus peptides recognized by antibodies in the sera of convalescent cases", *Virol.*, 324:251-256 (2004).

Harrison et al., "Screening of phage anibody libraries", *Meth. Enzymol.*, 267:83-109 (1996).

Holmes, K.V., "SARS coronavirus: a new challenge for prevention and therapy", *J. Clin. Invest.*, 111(11):1605-1609 (2003).

Hoogenboom et al., "By-passing immunization—human antibodies from synthetic repertoires of germline $V_H$ gene segments rearranged in Vitro", *J. Mol. Biol.*, 227(2):381-388 (1992).

Houghten et al., "The use of synthetic peptide combinatorial libraries for the identification of bioactive peptides", *BioTechniques*, 13(3):412-421 (1992).

Huse et al., "Generation of a large combinatorial library of the Immunoglobulin repertoire in phage lambda", *Science*, 246:1275-1281 (1989).

Huston et al., "Antigen recognition and targeted delivery by the single-chain Fv", *Cell Biophy.*, 22(1-3):189-224 (1993).

Igarashi et al., "Human immunodeficiency virus type 1 neutralizing antibodies accelerate clearance of cell-free virions from blood plasma", *Nat. Med.*, 5(2):211-216 (1999).

Kaplitt et al., "Long-term gene expression and phenotypic correction using adeno-associated virus vectors in the mammalian brain", *Nat. Genet.*, 8(2)154:148-154 (1994).

Keller et al., "Passive immunity in prevention and treatment of infectious diseases", *Clin. Microbiol. Rev.*, 13(4):602-614 (2000).

Kida et al., "Neutralization of feline infectious peritonitis virus: preparation of monoclonal antibody that shows cell tropism in neutralizing activity after viral absorption into the cells", *Arch. Virol.*, 145(1):1-12 (2000).

Kolb et al., "Virus-neutralizing monoclonal antibody expressed in milk of transgenic mice provides full protection against virus-induced encephalitis", *J. Virol.*, 75(6):2803-2809 (2001).

Koo et al., "Protective immunity against murine hepatitis virus (MHV) induced by intranasal or subcutaneous administration of hybrids of tobacco mosaic virus that carries an MHV epitope", *Proc. Natl. Acad. Sci. USA*, 96(14):7774-7779 (1999).

Kuiken et al., "Newly discovered coronavirus as the primary cause of severe acute respiratory syndrome", *Lancet*, 362(9380):263-270 (2003).

Kuklin et al., "Modulation of mucosal and systemic immunity by enteric administration of nonreplicaating herpes simplex virus expressing cytokines", *Virol.*, 240(2):245-253 (1998).

Lam et al., "A new type of synthetic peptide library for identifying ligand-binding activity", *Nature*, 354(6348):82-84 (1991).

Lam, K.S., "Application of combinatorial library methods in cancer research and drug discovery", *Anti-cancer Drug Des.*, 12(3):145-167 (1997).

Lamarre et al., "A recombinant single chain antibody neutralizes coronavirus infectivity but only slightly delays lethal infection of mice", *Eur. J. Immunol.*, 27(12):3447-3455 (1997).

La Montagne et al., "Severe acute respiratory syndrome: developing a research response", *Infect. Dis.*, 189:634-641 (2004).

Lanza et al., "Active immunity against the CD4 receptor by using an antibody antigenized with residue 41-55 of the first extracellular domain", *Proc. Natl. Acad. Sci. USA*, 90:11683-11687 (1993).

La Salle et al., "An adenovirus vector for gene transfer into nervous and glia in the brain", *Science*, 259:988-990 (1993).

Li et al., "Profile of specific antibodies to the SARS-associated coronavirus", *N. Engl. J. Med.*, 349:508-509 (2003).

Li et al., "Angiotensin-converting enzyme 2 is a functional receptor for the SARS coronavirus", *Nature*, 426(6965):450-454 (2003).

Li et al., "Efficient replication of severe acute respiratory syndrome coronavirus in mouse cells is limited by murine angiotension-converting enzyme 2", *J. Virol.*, 78(20):11429-11433 (2004).

Lonberg et al., "Antigen-specific human antibodies from mice comprising four distinct genetic modifications", *Nature*, 368(6474):856-859 (1994).

Lonberg et al., "Human antibodies from transgenic mice", *Int. Rev. Immunol.*, 13(1):65-93 (1995).

Lunde et al., "Troybodies and pepbodies", *Biochem. Soc. Trans.*, 30(part 4):500-506 (2002).

Luo et al., "Roles in cell-to-cell fusion of two conserved hydrophobic regions in the murine coronavirus spike protein", *Virol.*, 244(2):483-494 (1998).

Malmqvist, M., "Biospecific interaction analysis using biosensor technology", *Nature*, 361(6408):186-187 (1993).

Marasco et al., "Design, intracellular expression, and activity of a human anti-human immunodeficiency virus type 1 gp120 single-chain antibody", *Proc. Natl. Acad. Sci. USA*, 90:7889-7893 (1993).

Marks et al., "By-passing immunization—human antibodies from V-gene libraries displayed on phage" *J. Mol. Biol.*, 222(3):581-597 (1991).

Marks et al., "By-passing immunization: building high affinity human antibodies by chain shuffling", *Biotechnol.*, 10(7):779-783 (1992).

Marra et al., "The genome sequence of the SARS-associated coronavirus", *Science*, 300:1399-1401 (2003).

Matthews et al.. "Immunogenically fit subunit vaccine components via Epitope discovery from natural peptide libraries", *J. Immunol.*, 169:837-846 (2002).

Milligan et al., "Generation of humoral immune respeonses against herpes simplex virus type 2 in the murine female genital tract", *Virol.*, 206(1):234-241 (1995).

Moore et al., "Identification of amino acids involved in a serotype and neutralization specific Epitope within the s1 subunit of avian infectious bronchitis virus", *Arch. Virol.*, 142(11):2249-2256 (1997).

Moore et al., "Retroviruses pseudotyped with the severe acute respiratory syndrome coronavirus spike protein efficiently infect cells expressing angiotension-converting enzyme 2", *J. Virol.*, 78(19):10628-10635 (2004).

Morrison, S.L., "Success in specification", *Nature*, 368(6474):812-813 (1994).

Morrison et al., "High-flow microinfusion: tissue penetration and pharmacodynamics", *Am. J. Physiol.*, 266(1):R292-R305 (1994).

Naldini et al., "Efficient transfer, integration, and sustained long-term expression of the transgene in adult rat brains injected with a lentiviral vector", *Proc. Natl. Acad. Sci. USA*, 93:11382-11388 (1996).

Neuberger, M., "Generating high-agidity human mabs in mice", *Nat. Biotechnol.*, 14(7):826 (1996).

Ogueta et al., "Design and in vitro characterization of a single regulatory module for efficient control of gene expression in both plasmid DNA and a self-inactivating lentiviral vector", *Mol. Med.*, 7(8):569-579 (2001).

Parren et al., "The anti viral activity of antibodies in vitro and in vivo", *Adv. Immunol.*, 77:195-262 (2001).

Pearson et al., "SARS—what have we learned?", *Nature*, 424:121-126 (2003).

Piccirillo et al., "Immune modulation by plasmid DNA-mediated cytokine gene transfer", *Curr. Pharm. Des.*, 9:83-94 (2003).

Radaelli et al., "Comparative analysis of immune responses and cytokine profiles elicited in rabbits by the combined use of recombinant fowlpox viruses, plasmids and virus-like particles in prime-boost vaccination protocols against SHIV", *Vaccine*, 21:2052-2064 (2003).

Reeves et al., "Sensitivity of HIV-1 to entry inhibitors correlates with envelope/coreceptor affinity, receptor density, and fusion kinetics", *Proc. Natl. Acad. Sci. USA*, 99(25)16249-16254 (2002).

Reff et al., "Depletion of B cells in vivo by a chimeric mouse human monoclonal antibody to CD20", *Blood*, 83(2):435-445 (1994).

Rota et al., "Characterization of a novel coronavirus associated with severe acute respiratory syndrome", *Science*, 300:1394-1399 (2003).

Ruan et al., "Comparative full-length genome sequence analysis of 14 SARS coronavirus isolates and common mutations associated with putative origins of infection", *Lancet*, 361(9371):1779-1785 (2003).

Schier et al., "In vitro and in vivo characterization of a human anti-c-erbB-2 single-chain Fv isolated from a filamentous phage antibody library", *Immunotechnol.*, 1:73-81 (1995).

Scott et al., "Searching for peptide ligands with an Epitope library", *Science*, 249:386-390 (1990).

Shibata et al., "Neutralizing antibody directed against the HIV-1 envelope glycoprotein can completely block HIV-1/SIV chimeric virus infections of macaque monkeys", *Nat. Med.*, 5(2):204-210 (1999).

Shopes, B., "A genetically engineered human IgG mutant with enhanced cytolytic activity", *J. Immunol.*, 148:2918-2922 (1992).

Song et al., "Induction of protective immunity in chickens vaccinated with infectious bronchitis virus S1 glycoprotein expressed by a recombinant baculovirus", *J. Gen. Virol.*, 79(4):719-723 (1998).

Steward et al., "A mimotope from a solid-phase peptide library induces a measles virus-neutralizing and protective antibody response", *J. Virol.*, 69(12):7668-7673 (1995).

Subbarao et al., "Prior infection and passive transfer of neutralizing antibody prevent replication of severe acute respiratory syndrome coronavirus in the respiratory tract of mice", *J. Virol.*, 78(7):3572-3577 (2004).

Sui et al., "Potent neutralization of severe acute respiratory syndrome (SARS) coronavirus by a human mAb to S1 protein that blocks receptor association", *Proc. Natl. Acad. Sci. USA*, 101(8):2536-2541 (2004).

Taboga et al., "A large-scale evaluation of peptide vaccines against foot-and-mouth disease: lack of solid protection in cattle and isolation of escape mutants", *J. Virol.*, 71(4):2606-2614 (1997).

Taguchi et al., "Functional analysis of a epitope in the S2 subunit of the murine coronavirus spike protein: involvement in fusion activity", *J. Gen. Virol.*, 81:2867-2871 (2000).

Tsai et al., "A 12-amino acid stretch in the hypervariable region of the spike protein S1 subunit is critical for cell fusion activity of mouse hepatitis virus", *J. Biol. Chem.*, 247(37):26085-26090 (1999).

Ulmer, J.B., "Elegantly presented DNA vaccines", *Nat. Biotechnol.*, 15(9):842-843 (1997).

Vennema et al., "Primary structure of the membrane and nucleocapsid protein genes of feline infectious peritonitis virus and immunogenicity of recombinant vaccinia viruses in kittens", *Virol.*, 181(1):327-335 (1991).

Wilkinson, D., "Immunochemical techniques inspire development of new antibody purification methods", *The Scientist*, 14(8):25-28 (2000).

Wong et al., "A 193-amino acid fragment of the SARS coronavirus S protein efficiently binds angiotensin-converting enzyme 2", *J. Biol. Chem.*, 279(5)3197-301 (2004.

Woo et al., "Relative rates of non-pneumonic SARS coronavirus infection and SARS coronavirus pneumonia", *Lancet*, 363(9412):841-845 (2004).

Xu et al., "Genetic variation of SARS coronavirus in Beijing hospital", *Emerging Infect. Dis.*, 10(5):789-794 (2004).

Yang et al., "Cellular and humoral immune responses to viral antigens create barriers to lung-directed gene therapy with recombinant adenoviruses", *J. Virol.*, 69(4):2004-2015 (1995).

Yang et al., "pH-dependent entry of severe acute respiratory syndrome coronavirus is mediated by the spike glycoprotein and enhanced by dendritic cell transfer through DC-SIGN", *J. Virol.*, 78(11):5642-5650 (2004).

Yeh et al., "Characterization of severe acute respiratory syndrome coronavirus genomes in Taiwan: molecular epidemiology and genome evolution", *Proc. Natl. Acad. Sci. USA*, 101(8):2542-2547 (2004).

You et al., "Targeting dendritic cells to enhance DNA vaccine potency", *Cancer Res.*, 61:3704-3711 (2001).

Yoo et al., "A single amino acid change within antigenic domain II of the spike protein of bovine coronavirus confers resistance to virus neutralization", *Clin. Diagn. Lab. Immunol.*, 8(2):297-302 (2001).

Yu et al., "Affinity maturation of phage-displayed peptide ligands", *Meth. Enzymol.*, 267:3-27 (1996).

Yu et al., "Characterization of murine coronavirus neutralization Epitopes with phage-displayed peptides", *Virol.*, 271(1):182-196 (2000).

Zaghouani et al., "Induction of antibodies to the human immunodeficiency virus type 1 by immunization of baboons with immunoglobulin molecules carrying the principal neutralizing determinant of the envelope protein", *Proc. Natl. Acad. Sci. USA*, 92:631-635 (1995).

Zanetti, M., "Antigenized antibodies", *Nature*, 355(6359):476-477 (1992).

Zebedee et al., "Human combinatorial antibody libraries to hepatitis B surface antigen, *Proc. Natl. Acad. Sci. USA*, 89:3175-3179 (1992).

Zhu et al., "Extended half-life and elevated steady-state level of a single-chain Fv intrabody are critical for specific intracellular retargeting of its antigen, caspase-7, *J. Immunol. Meth.*, 231(1-2):207-222 (1999).

Zhu et al., "Development of constitutive and inducible self-inactivating lentiviral vectors and their application in cardiovascular gene transfer", *Gene Ther. Mol. Biol.*, 8:91-102 (2004).

Zuber et al., "Induction of immune responses and break of tolerance by DNA against HIV-1 coreceptor CCR5 but no protection from SIVsm challenge", *Virol.*, 278(2):400-411 (2000).

Zuckermann et al., "Discovery of nanomolar ligands for 7-transmembrane G-protein-coupled receptors from a diverse N-(substituted)glycine peptoid library", *J. Med. Chem.*, 37(17):2678-2685 (1994).

Bonavia et al., "Identification of a receptor-binding domain of the spike glycoprotein of human coronavirus HcoV-229E", *J. Virol.*, 77(4):2530-2538 (2003).

Kubo et al., "Localization of neutralizing epitopes and the receptor-binding site within the amino-terminal 330 amino acids of the murine coronavirus spike protein", *J. Virol.*, 68(9):5403-5410 (1994).

Li et al., "The structural characterization and antigenicity of the S protein of SARS-CoV", *Geno, Prot. Bioinfo.*, 1(2):108-117 (2003).

\* cited by examiner

Fig. 1

MFIFLLFLTLTSGSDLDRCTTFDDVQAPNYTQHTSSMRGVYYPDEIFRSDTLYLTQDLFLPFYSNVTGFHTINHTFGNPV
IPFKDGIYFAATEKSNVVRGWVFGSTMNNKSQSVIINNSTNVIRACNFELCDNPFFAVSKPMGTQTHTMIFDNAFNCT
FEYISDAPSLDVSEKSGNFKHLREFVFKNKDGFLYVYKGYQPIDVVRDLPSGFNTLKPIFKLPLGINITNFRAILTAFSP
                                                  RTMHPSDEFLDLGMP (SEQ ID NO:23)
AQDIWGTSAAAYFVGYLKPTTFMLKYDENGTIITDAVDCSQNPLAELKCSVKSFEIDKGIYQTSNFRWAPSGPVRFPNIT
                                                                 WAPLGRCVSHPAIC
NLCPFGEVFNPSVYAWERKKISNCVADYSVLYNSTFFSTPKCYGVSATKLNDLCFSNVYADSFVVKGDDVRQIAPGQTGV
A (SEQ ID NO:24)
IADYNYKLPDDFMGCVLAWNTRNIDATSTGNYNYKYRYLRHGKLRPFERDISNVPFSPDGKPCTPPALNCYMPENDYGFY
                                                                SVDDCRWNENCEPPP (SEQ ID NO:25)
TTTGIGYQPYRVVLSFELLNAPAHVGGPKLSTDLIKNQCVNFNFNGLTGHGVLTPSSKRFQPFQQFGRDVSDFIDSVRD
                            CLSATCDCHLGGP          GHGLVPLFDPRVRFL (SEQ ID NO:26, SEQ ID NO:27)
PKTSEILDISPCAFGGVSVITPGTNASSEVAVLYQDVNCTDVSTAIHADQLTPAWRIYSTGNNVFQTAGCHIGAEHVDT
                  PNCWVGLHGAHSCFL (SEQ ID NO:28)                YQADCLMNRCPTAE (SEQ ID NO:29)
SYECDIPIGAGICASYHTVSLLRSTSQKS (SEQ ID NO:30)

Fig. 6

ANTIBODIES AGAINST SARS-COV AND METHODS OF USE THEREOF

RELATED APPLICATIONS

This application claims priority to U.S. Ser. No. 60/524,840, filed on Nov. 25, 2003, which is herein incorporated by reference in its entirety.

GRANT SUPPORT

This invention was made with United States Government support under National Institutes of Health Grants A128785, A148436, and A1053822. The United States Government may have certain rights in the invention.

FIELD OF THE INVENTION

This invention relates generally to anti-viral antibodies as well as to methods for use thereof.

BACKGROUND

Severe acute respiratory syndrome ("SARS") is highly communicable human disease. In the spring of 2003, a sudden, unexpected world-wide epidemic occurred in which more than 8000 people were believed to have been infected and more than 800 are known to have died (see Pearson et al., Nature 424:121 (2003)). Although the 2003 epidemic was stemmed by infection control measures, the infection could re-emerge at any time and has the potential to cause a global pandemic as devastating as HIV/AIDS (De Groot, Vaccine 21:4095-104 (2003)).

The etiologic agent of SARS was rapidly identified as a new coronavirus (SARS-CoV) (see Rota et al, Science 300: 1394-99 (2003)); Marra et al., Science 300:1399 (2003)) and found to cause a similar respiratory disease in a non-human primate model (see Fouchier et al., Nature 423:240 (2003); Kuiken et al., Lancet 362:263-70 (2003)). SARS is a highly communicable illness consisting of fever and respiratory symptoms that can progress to pneumonia, respiratory failure, and death. Infrequently, a subclinical or non-pneumonic form of the syndrome may also exist (see Ho et al., J. Infect Dis. 189:634-41 (2004); Woo et al., Lancet 363:841-45 (2004)).

Effective prophylaxis and therapies are urgently needed in the event that there is reemergence of the highly contagious and often lethal severe acute respiratory syndrome (SARS) coronavirus (SARS-CoV) infection. Currently, prevention of SARS has largely relied on improved awareness, surveillance, and institution of local, regional and international public-health-care measures (see Stadler et al., Nat Rev Microbiol 1:209-18 (2003)). Significant efforts in the area of SARS vaccine research have been initiated and several recent reports have documented that transfer of immune serum from mice with prior SARS-CoV infection, or from mice vaccinated with a DNA plasmid encoding SARS S protein or a vaccinia virus expressing the S protein, can prevent virus replication in the lungs and upper respiratory tract (see Bisht et al., Proc. Natl. Acad Sci USA 101:6641-46 (2004); Subbarao et al., J Virol 78:3572-77 (2004); Yang et al., Nature 428:561-64 (2004)). In addition, in SARS-CoV infection of humans, decreasing virus titers from nasopharyngeal aspirates, serum, urine and stool have been observed to be coincident with the development of neutralizing antibodies (see Li et al., N Engl Med 349:508-09 (2003); Peiris et al., Lancet 361:1767-72 (2003)). Treatment of SARS with convalescent plasma has been reported (see Burnouf et al., Hong Kong Med. J. 9:309-10 (2003); Wong et al., Hong Kong Med. J. 9:199-201 (2003)).

These studies support the importance of humoral immunity in protection against SARS-CoV and suggest that a specific and effective human monoclonal antibody (MAb) should be developed to provide a prophylaxis and early treatment against SARS in the event that episodic or even widespread reemergence into the human population occurs.

SUMMARY OF THE INVENTION

Provided herein are monoclonal antibodies which neutralize SARS-CoV. Specifically, such MAbs bind to an epitope on a region of the spike protein of SARS-CoV and neutralize SARS-CoV. For example, the region of the spike protein of SARS-CoV is the S1 region and/or the monoclonal antibody can be monoclonal antibody 80R. The monoclonal antibody can bind to a region between amino acid residues 318 and 510 of the SARS-CoV S1 region. More specifically, the monoclonal antibody can bind to a region between amino acid residues 324 and 503. Moreover, the best sequences for designing peptides that will produce antibodies similar to MAb 80R are likely SFELxxxPFGE (SEQ ID NO:33) and/or SFELxxxxxPFGE (SEQ ID NO:34) in forward or reverse orientation.

The monoclonal antibodies of the invention can have the binding affinity of monoclonal antibody 80R. Alternatively, the binding affinity can range from about $10^{-6}$ M to about $10^{-12}$ M.

The monoclonal antibodies of the invention can inhibit binding of the S1 region of the S protein of SARS-CoV to the ACE2 receptor. Moreover, the monoclonal antibodies can also inhibit syncytia formation between cells expressing SARS-CoV S protein and cells expressing the SARS-CoV receptor ACE2.

Also included are monoclonal antibodies that compete with the binding of monoclonal antibody 80R to the S1 region of the SARS-CoV S protein. Monoclonal antibodies of the invention are capable of neutralizing SARS-CoV, and include monoclonal antibodies that bind to the same epitope as the 80R monoclonal antibody.

The antibodies of the invention may contain one or more sequences selected from the group consisting of SEQ ID NOS:2, 3, 4, and 5.

Also included with in the invention are scFv antibodies which neutralize SARS-CoV. Specifically, such scFvs bind to an epitope on a region of the spike protein of SARS-CoV and neutralize SARS-CoV. For example, the region of the spike protein of SARS-CoV is the S1 region and/or the scFv can be scFv antibody 80R. The scFv antibody can bind to a region between amino acid residues 318 and 510 of the SARS-CoV S1 region. More specifically, the monoclonal antibody can bind to a region between amino acid residues 324 and 503. Additionally, the best sequences for designing peptides that will produce antibodies like MAb 80R are likely to be SFELxxxPFGE (SEQ ID NO:33) and/or SFELxxxxxPFGE (SEQ ID NO:34) in forward or reverse orientation. The scFv antibody can have the binding affinity of scFv antibody 80R. Alternatively, the binding affinity can range from about $10^{-6}$ M to about $10^{-12}$ M.

The scFv antibodies of the invention can inhibit binding of the S1 region of the S protein of SARS-CoV to the ACE2 receptor. Moreover, the scFv antibodies can also inhibit syncytia formation between cells expressing SARS-CoV S protein and cells expressing the SARS-CoV receptor ACE2.

Also included are scFv antibodies that compete with the binding of scFv antibody 80R to the S1 region of the SARS-CoV S protein. scFv antibodies of the invention are capable of neutralizing SARS-CoV, and include scFv antibodies that bind to the same epitope as the 80R scFv antibody.

The scFv antibodies of the invention may have the sequence of SEQ ID NO:1.

Also provided are methods of preventing a disease or disorder caused by a coronavirus by administering to a person at risk of suffering from said disease or disorder, a therapeutically effective amount of a monoclonal antibody or an scFv antibody of the invention to a person at risk of suffering from the disease or disorder. Such methods may also include administering other anti-viral drugs and/or entry inhibitors in addition to administering the monoclonal antibody or scFv antibody. Those of ordinary skill in the art will be able to routinely select an appropriate anti-viral drug or entry inhibitor for use in conjunction with the monoclonal antibodies or scFv antibodies of the invention. For example, when the coronavirus is SARS-CoV, suitable monoclonal antibodies include monoclonal antibody 80R, and suitable scFv antibodies include scFv 80R.

The invention also provides methods of treating a coronavirus-related disease or disorder by administering a therapeutically effective amount of a monoclonal antibody or a scFv antibody of the invention to a person suffering from a coronavirus-related disease or disorder. For example, the coronavirus-related disease or disorder can be SARS. The monoclonal antibody that is administered can be monoclonal antibody 80R. Suitable scFv antibodies include scFv 80R.

Also provided are methods for vaccinating a patient against SARS-CoV by administering an immunogenically effective amount of a vaccine candidate peptide to a patient in need of vaccination, wherein the vaccine candidate peptide binds to a monoclonal antibody or a scFv antibody of the invention. For example, the monoclonal antibody can be monoclonal antibody 80R, and the vaccine candidate peptide can contain the monoclonal antibody 80R epitope. Additionally or alternatively the scFv can be scFv 80R and the vaccine candidate peptide can contain the scFv 80R epitope.

The invention also provides methods of diagnosing a coronavirus-related disease or disorder. Such methods include the steps of contacting a test sample obtained from a patient suspected of having the coronavirus-related disease or disorder with the monoclonal antibody of the invention and detecting the presence or absence of an antibody-antigen complex, wherein the presence of the antibody-antigen complex indicates that the patient has the coronavirus-related disease or disorder. For example, the coronavirus-related disease or disorder can be SARS. Those skilled in the art will recognize that the monoclonal antibody can be monoclonal antibody 80R. The sample tested may be obtained from blood, hair, cheek scraping, saliva, biopsy, or semen. In some embodiments, the detecting occurs in vivo.

Also included are methods of detecting the presence of a coronavirus in a sample. Such methods involve the steps of contacting the sample with a monoclonal antibody of the invention and detecting the presence or absence of an antibody-antigen complex, thereby detecting the presence of a coronavirus in a sample. In some embodiments, the coronavirus is SARS-CoV. For example, the monoclonal antibody used in contacting step may be monoclonal antibody 80R. Moreover, the detecting step may occur in vivo. The sample tested may be obtained from blood, hair, cheek scraping, saliva, biopsy, or semen.

Also provided are compositions containing a monoclonal antibody or the scFv of the invention and a carrier. Such compositions can be provided in a kit containing the components in one or more containers. Also contemplated are passive vaccines against SARS-CoV, wherein the passive vaccines contain such compositions.

The invention additionally includes methods of screening for compounds that modulate the interaction between SARS-CoV and the SARS-CoV receptor, ACE2. Such methods include the steps of introducing a candidate compound to an antibody-antigen complex, wherein the antibody is monoclonal antibody 80R and said antigen is located on the S1 region of the S protein of SARS-CoV and determining whether the candidate compound disrupts the antibody-antigen complex, wherein the disruption of the antibody-antigen complex indicates that the candidate compound modulates the interaction between SARS-CoV and ACE2. The SARS-CoV-related disease or disorder can include, e.g., SARS.

Moreover, the invention also provides methods for identifying compounds useful to treat a SARS-CoV-related disease or disorder, by providing at least one SARS-CoV protein; exposing the SARS-CoV protein to a monoclonal antibody of the invention; detecting the formation of an antibody-antigen complex; introducing one or more candidate compounds; and determining whether the one or more candidate compounds disrupt the antibody-antigen complex, wherein the disruption of the antibody-antigen complex indicates that the one or more candidate compounds is useful to treat a SARS-CoV-related disease or disorder. In this method, the monoclonal antibody can be monoclonal antibody 80R and the at least one SARS-CoV protein may include the S1 region of the spike protein of SARS-CoV. For example, the region may be between amino acid residues 318 and 510 of the SARS-CoV S1 region. More specifically, this region may be between amino acid residues 324 and 503 of the SARS-CoV S1 region. This protein can be provided as part of a SARS-CoV molecule or it can be provided in a cell infected with the SARS-CoV.

Also provided herein are methods of enhancing the neutralization activity of MAb 80R and/or scFv 80R by performing complementarity determining region mutagenesis (e.g., by heavy and light chain swapping or by CDR doping) on the MAb 80R or scFv 80R binding site; determining the neutralization activity of the mutated MAbs and/or scFvs; and identifying those mutated MAbs and/or scFvs having increased neutralization activity. For example, those skilled in the art will recognize that enhancing the neutralization activity of MAb 80R and/or scFv 80R can be accomplished by increasing the affinity of the antibody for its epitope. However, any other method known to those skilled in the art that allows MAb 80R and/or scFv 80R to recognize SARS-CoV escape mutants can also be employed. By way of non-limiting example, an MAb 80R and/or scFv 80R having enhanced neutralization activity will be able to neutralize the SARS-CoV D480G mutation (e.g., the mutation found in the GD03T patient). The invention also encompasses mutants having enhanced neutralization activity which have been identified according to the methods described herein.

Also provided are monoclonal antibodies which neutralizes SARS-CoV, wherein said antibodies have a light chain with three CDRs comprising an amino acid sequence selected from the group consisting of the amino acid sequences of RASQVRSNLA (SEQ ID NO:37); DASTAT (SEQ ID NO:38); and QQRSNWPPT (SEQ ID NO:39); a heavy chain with three CDRs comprising an amino acid sequence selected from the group consisting of the amino acid sequences of AH; VYDNK (SEQ ID NO: 35); and RSYYL (SEQ ID NO:36); or a light chain with three CDRs comprising an amino acid sequence selected from the group consisting of the amino acid sequences of RASQVRSNLA (SEQ ID NO:37); DASTAT (SEQ ID NO:38); and QQRSNWPPT (SEQ ID NO:39) and a heavy chain with three CDRs comprising an amino acid sequence selected from the group consisting of the amino acid sequences of AH; VYDNK (SEQ ID NO: 35); and RSYYL (SEQ ID NO:36).

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In the case of conflict, the present specification, including definitions, will control. In addition, the materials, methods, and examples are illustrative only and are not intended to be limiting.

Other features and advantages of the invention will be apparent from the following detailed description and claims.

BRIEF DESCRIPTION OF THE DRAWINGS

FIG. 1 shows the amino acid sequences of eight anti-S1 scFvs (6A, 8C, 12E, 26H, 27D, 80R, 91M, and 92N). Framework regions 1-4 (FW1-4), and Complementarity determining regions 1-3 (CDR1-3) for both the VH and VL are shown. The VH and VL family designations are also shown.

FIG. 6 is a sequence alignment of seven affinity-selected peptide amino acid sequences to the SARS-CoV S1 protein. Peptide sequences are underlined and identities to SARS-CoV S1 protein are highlighted. These peptides were identified using S1 phage panning studies.

FIG. 8A shows the indicated amino acid residues in S1(318-510) of Tor2 that were individually replaced with corresponding variant amino acids found in SARS-like-CoVs or in other human SARS-CoVs. These residues also were substituted with alanine. Alterations of K344A, N479A and T487A affect the binding to 80R to some degree: N479K substitution results in a ~50% decrease of 80R binding, and D480G substitution totally abolishes binding to 80R. FIG. 8B shows that multiple substitutions with the amino acids of civet SZ3 virus (344R/360S/479K/487S) in the S1 (318-510)-Ig construct of Tor2 had no effect on 80R binding, as well as the full-length S1 (12-672) of SZ3 which was synthesized de novo. Multiple substitutions with the amino acids of human GD03T virus (344R/360S/472P/480G/487S) in the S1 (318-510)-Ig construct of Tor2 and the full length S1 (12-672) of GD03T completely lose binding to 80R. FIG. 8C demonstrates that the full-length S protein of Tor2 and variants containing amino-acid substitutions of isolates SZ3 or GD03T were precipitated by 1D4, which recognizes a C9 tag present at the carboxyl-terminus of each S protein, or by 80R IgG1, and analyzed by SDS-PAGE. Binding activities of these full-length S proteins to 80R IgG1 were consistent with that of their RBDs (318-510) or S1 domain (12-672) to 80R scFv.

FIG. 9A shows that S1 (324-503) is the smallest fragment bound to 80R. Either N-terminal or C-terminal truncation variants slightly smaller than S1(324-503) had either decreased expression or lost binding activity to 80R. FIG. 9B shows the critical residues for the 80R epitope that were observed. Specifically, individual alanine substitution of glutamic acid 452, aspartic acids 454 and 480 in the S1 (318-510) fragment impaired or abolished binding to 80R.

FIG. 10 is a series of graphs showing 80R IgG1 neutralization of pseudoviral infection mediated by full-length SARS-CoV spike variants. HIV viruses pseudotyped with the S protein from Tor2, SZ3 or GD03T isolates were incubated with the indicated concentration of 80R IgG1 (solid line, diamonds) or non-relevant human IgG1 (solid line, squares) for one hour prior to infection. 48 hours after infection, luciferase activities in target cells were measured, relative viral inhibition was calculated as the ratio of luciferase activity in the presence to absence of 80R IgG1 or non-relevant human IgG1.

DETAILED DESCRIPTION OF THE INVENTION

Figure 2A:
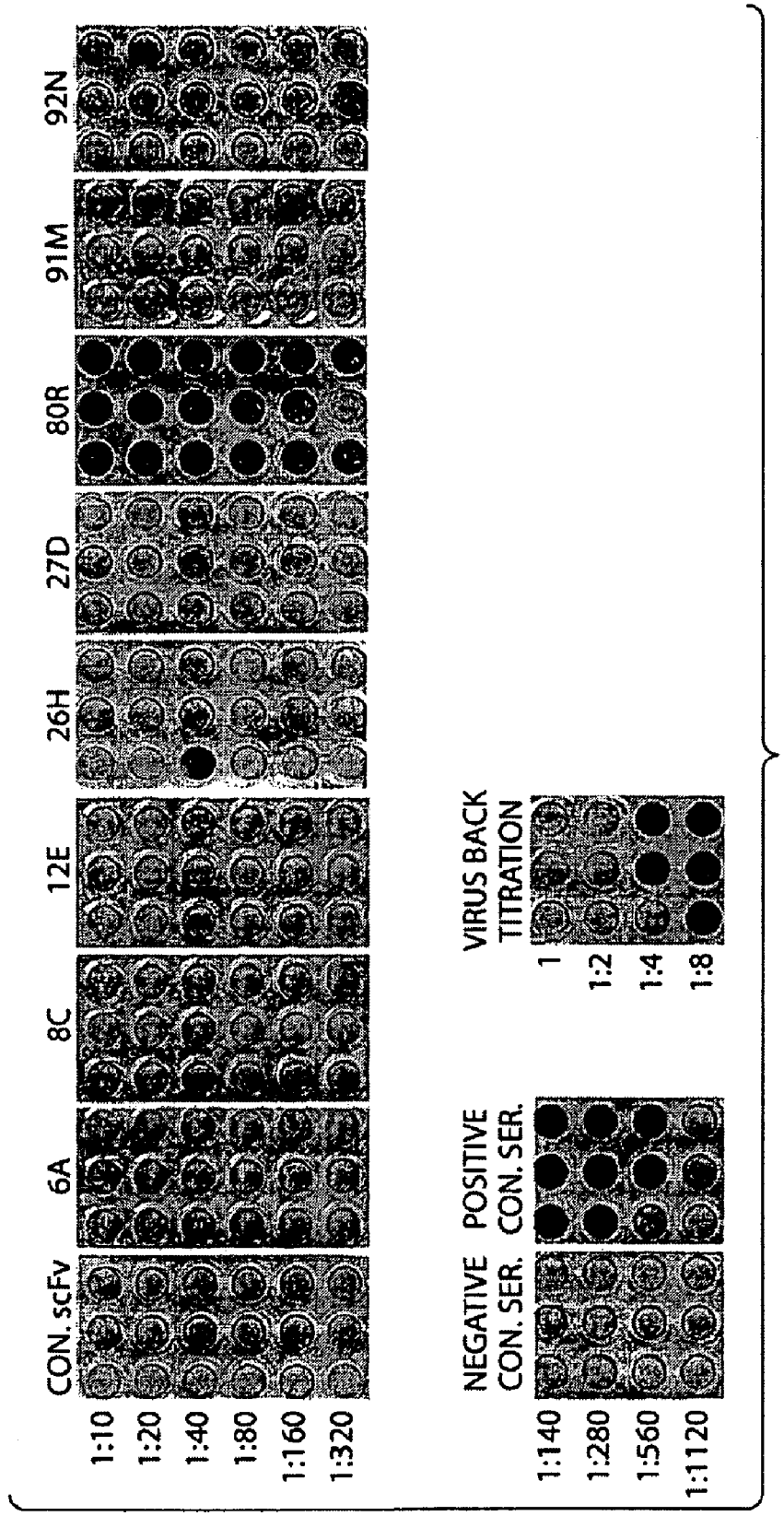
FIG. 2A shows the results of the micro-neutralization assay using anti-S1 scFvs. The positive control was convalescent serum from a SARS patient. The negative control was non-SARS human serum. The name of scFvs are labeled on the top. Antibody titers are indicated on the left. Undiluted SARS-CoV (~37 pfu) was loaded per well.

The SARS coronavirus (SARS-CoV) is a member of the Coronaviridae family of enveloped, positive-stranded RNA viruses, which as a group, have a broad host range. It contains three major structural proteins: spike (S), membrane (M), nucleocapsid (N). Though it has been shown that passive protection from murine hepatitis virus (MHV, a intensively investigated coronavirus), infection has been achieved by administration of MAb specific for all major structural proteins of the virus, the spike protein (S) is the major antigenic determinant for coronaviruses. The serological response in the host is typically raised against the S protein (see Moore et al., Arch. Virol. 142 (11):2249-56 (1997); Talbot et al., J. Virol. 62:3032 (1988); Gallagher et al., Virology 279(2):371-74 (2001); Song et al., J. Gen. Virol. 79(4):719-23 (1998); and Lamarre et al., Eur. J. Immunol. 27:3447-55 (1997), each of which are incorporated herein by reference).

Two functional domains at the amino (S1) and carboxyl (S2) termini of the S protein are conserved among the coronaviruses. The S1 domain of spike protein contains neutralizing epitopes for most known coronaviruses and therefore is likely to encode determinants for host tropism, neutralizing antibodies, and viral virulence. The S1 and S2 domains of SARS-CoV S protein can be identified by sequence alignment with other coronavirus S proteins, especially by aligning the more conserved S2 domain alignment.

Moreover, it has been demonstrated that the binding of S1 to its receptor, ACE2, on host cells is responsible for SARS-CoV entry into cells. (See Li W et al., Nature 426:450-54 (2003), incorporated herein by reference). In addition, the S2 domain is another functional domain of S protein that is also a useful target for generating neutralizing antibody. Both the S1 and S2 domains of coronavirus spike proteins have been shown to be critical for cell-to-cell fusion. (See Luo and Weiss, Virol. 244:483 (1998), Tsai et al., J. Biol. Chem. 247(37):26085 (1999); Taguchi et al., J. Gen. Virol. 81:2867 (2000), incorporated herein by reference).

The M glycoprotein is the most abundant transmembrane envelope glycoprotein in the virus particle. Neutralizing epitopes were found to be present on M protein for other coronaviruses. (See Kida et al., Arch. Virol. 145:1-12 (2000)). The transmembrane M glycoprotein binds to the nucleocapsid protein in vitro, is probably involved in viral budding, and is essential for envelope formation. (See Holmes and Lai, in Fields Virology, Third Edition, Fields et al., eds. Lippincott-Raven (Philadelphia), pp. 1075-94 (1996)). The internal structural protein N binds to viral genomic RNA during virion assembly to form the helical nucleocapsid.

The instant invention provides methods for the identification, production and characterization of neutralizing human anti-S1 monoclonal antibodies 80R against SARS-CoV that blocks the binding of S1 to ACE2. Monoclonal antibody 80R acts as a viral entry inhibitor (see Sui et al., Proc Natl Acad Sci USA 101:2536-41 (2004)) that act as a potent neutralizing antibody capable of blocking the binding of the S1 region of the spike protein of SARS-CoV to its receptor, ACE 2 (see Li et al., Nature 426:450-54 (2003)).

Recent studies of SARS-CoVs demonstrate that amino acid changes between SARS strains and/or outbreaks are mainly located within the S1 region, which also contains the ACE2 receptor-binding domain. A comparison of variations in the ACE2 receptor- and 80R-binding domains (residues 318-510 of S1) of 78 reported human SARS-CoV sequences and SARS-like-CoV (e.g. from the Himalayan palm civet) sequences is presented in Table 1. (see The Chinese SARS Molecular Epidemiology Consortium, Science 303:1666-69 (2004); Guan et al., Science 302:276-78 (2003); Xu et al, Emerging Infectious Diseases 10:789:794 92004); Yeh et al., Proc Natl Acad Sci USA 101:2542-47 (2004)).

TABLE 1

Amino Acid Changes in SARS-like CoVs and SARS-CoVs from Human Cases

| | Example | | | | | | | |
|---|---|---|---|---|---|---|---|---|
| | | GenBank | | | | | | |
| | Name of Genomic | Accession | | | Amino acid No. | | | |
| Viral isolate | sequence | No | 344 | 360 | 472 | 479 | 480 | 487 |
| Middle/late phase 2002/2003 | Tor2 | AY278741 | K | F | L | N | D | T |
| Early phase 2002/2003 | GD01 | AY278489 | R/K | F | L | N | D | T |
| Palm civet | SZ3 | AY304486 | R | S | L | K | D | S |
| Guangdong index patient 2003/2004 | GD03T0013 | AY525636 | R | S | P | N | G | S |

A total of six differences are observed at positions 344, 360, 472, 479, 480, and 487 in this region. Among the human SARS-CoVs isolated from the 2002/2003 epidemic, amino acids arginine or lysine were present at position 344 in the early isolates (K344K/R) but lysine was present in the middle and late isolates. (See The Chinese SARS Molecular Epidemiology Consortium, Science 303:1666-69 (2004)). The amino acids at positions 472 and 480 were lysine and aspartic acid in all reported SARS-like-CoV S sequences and human SARS-CoV S sequences but were proline and glycine in the S sequence of the 2003/2004 Guangdong index patient (GD03T0013, referred to herein as GD03T) (L472P and D480G). As shown in Table 1, supra, major amino-acid variations between human SARS-CoVs of 2002/2003 and SARS-like-CoVs are observed at positions 360, 479 and 487 (F360S, N479K, T487S, SARS-CoV/SARS-like-CoV).

80R may not recognize the prototype SARS-Like viruses that have recently been isolated from civet cats by virtue of the fact that the D480G amino acid change found in the GD03T patient (FIG. 9) is also found in 26 civet cat sequences. Thus, if MAb 80R is going to be used in an outbreak setting where the emergence of SARS-like viruses from civet cats is expected, it may be necessary to perform (CDR) (complementarity determining region) mutagenesis on the 80R binding site to allow the antibody to also bind 480G variants of S1 protein. For example, CDR mutagenesis may be accomplished by light and heavy chain swapping, by CDR doping, or by any other method known to those skilled in the art. Currently, 480G is the only amino acid that is known to occur in natural variants of SARS-like coronaviruses that are resistant to 80R binding. As shown in FIG. 9, other amino acid changes also knock out binding. However, these have not been found in nature (real viruses). Thus, methods of enhancing the neutralization activity of 80R can be employed to isolate scFvs and/or MAbs having increased neutralization activity. For example, using complementarity determining region (CDR) mutagenesis on the 80R binding site, it may be possible to identify antibodies having broader neutralization activity (e.g., increased affinity) such that the antibodies are able to recognize specific escape mutants.

Identification and Characterization of scFvs and Monoclonal Antibodies

Figure 1:
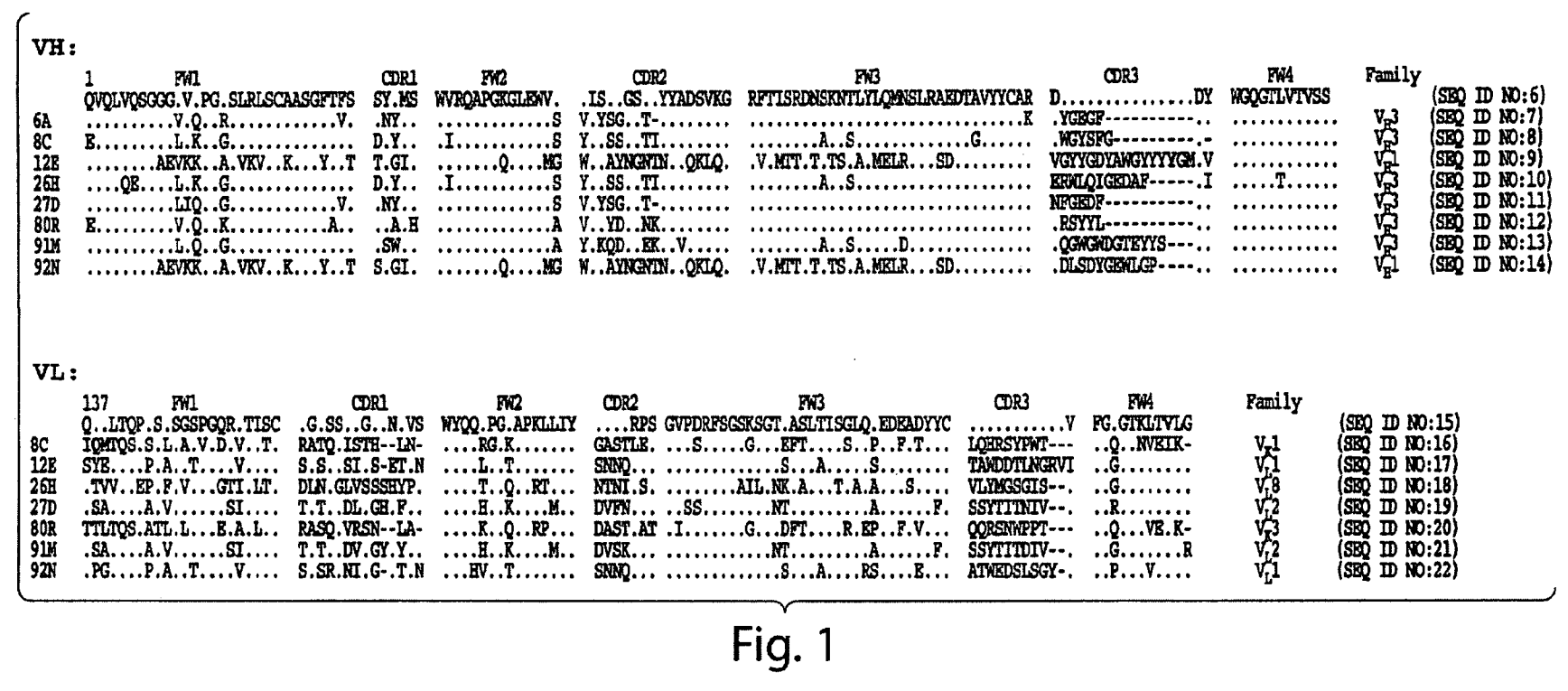

Eight unique anti-S1 scFvs were identified by sequencing analysis of individual clones. These scFvs were designated as 6A, 8C, 12E, 26H, 27D, 80R, 91M, 92N, and their amino acid sequences are presented in FIG. 1. Eight different VH and seven different VL sequences were revealed (scFv 6A did not have a VL sequence). The gene families for these scFvs were VH1 and VH3 for heavy chains and VL1, VL2, VL8, VK1 and VK3 for light chains. (See Examples 2, 3, and 14, infra).

Monovalent scFv 80R was shown to have potent neutralizing activity in vitro. (See FIG. 2). These results indicate that SARS-CoV neutralization does not require bivalent binding. However, those skilled in the art will recognize that monovalent scFv fragments are characterized by very fast blood clearance rates. Thus, in many cases, in order to achieve successful passive immunotherapy, the use of the bivalent full-length immunoglobulin is preferred due to avidity effects, effector functions, and prolonged serum half-life.

Therefore, as described in Example 3, infra, 80R scFv was converted to a bivalent human whole IgG1 (80R IgG1). Converting 80R to a bivalent human whole IgG1 molecule increases the half life of the antibody, as the half life of hIgG1 is approximately 21 days. Moreover, the 80R IgG1 monoclonal antibody includes various effector functions attributable to the immunoglobulin. As described herein, 80R IgG1 is a human antibody having a high affinity directed to the binding site of SARS-CoV to the ACE2 receptor.

As used herein, the terms "80R IgG1" and "monoclonal antibody 80R" and "full-length 80R" and "MAb 80R" and "80R MAb" are used interchangeably to refer to this bivalent full-length immunoglobulin.

The nucleic acid sequence of the 80R scFv and monoclonal antibody 80R are provided below:

80R scFv:

```
                                                          (SEQ ID NO:1)
GAGGTGCAGCTGGTGCAGTCTGGGGGAGGCGTGGTCCAGCCTGGGAAGTCCCTGAGACTCTC

CTGTGCAGCCTCTGGATTCGCCTTCAGTAGTTATGCTATGCACTGGGTCCGCCAGGCTCCAG

GCAAGGGGCTGGAGTGGGTGGCAGTTATATCATATGATGGAAGTAATAAATACTACGCAGAC

TCCGTGAAGGGCCGATTCACCATCTCCAGAGACAATTCCAAGAACACGCTGTATCTGCAAAT

GAACAGCCTGAGAGCTGAGGACACGGCTGTGTATTACTGTGCGAGGGACAGGAGCTACTACC

TTGACTACTGGGGCCAGGGAACCCTGGTCACCGTCTCCTCAGGTGGCGGCGGTTCCGGAGGT

GGTGGTTCTGGCGGTGGTGGCAGCGAAACGACACTCACGCAGTCTCCAGCCACCCTGTCTTT

GTCTCCAGGGGAAAGGGCCACCCTCTCCTGCAGGGCCAGTCAGAGTGTTAGGAGCAACTTAG

CCTGGTACCAGCAGAAACCTGGCCAGGCTCCCAGGCCCCTCATCTATGATGCATCCACCAGG

GCCACTGGCATCCCAGACAGGTTCAGTGGCAGTGGGTCTGGGACAGACTTCACTCTCACCAT

CAGCAGACTGGAGCCTGAAGATTTTGCAGTTTATTACTGTCAGCAGCGTAGCAACTGGCCTC

CGACGTTCGGCCAAGGGACCAAGGTGGAAGTCAAA
```

Variable region of heavy chain (VH) of 80R IgG1:

```
                                                          (SEQ ID NO:2)
GAGGTGCAGCTGGTGCAGTCTGGGGGAGGCGTGGTCCAGCCTGGGAAGTCCCTGAGACTCTC

CTGTGCAGCCTCTGGATTCGCCTTCAGTAGTTATGCTATGCACTGGGTCCGCCAGGCTCCAG

GCAAGGGGCTGGAGTGGGTGGCAGTTATATCATATGATGGAAGTAATAAATACTACGCAGAC
```

-continued
TCCGTGAAGGGCCGATTCACCATCTCCAGAGACAATTCCAAGAACACGCTGTATCTGCAAAT

GAACAGCCTGAGAGCTGAGGACACGGCTGTGTATTACTGTGCGAGGGACAGGAGCTACTACC

TTGACTACTGGGGCCAGGGAACCCTGGTCACCGTCTCCTCA

Constant region of heavy chain (Gammal, Cγ1) of 80R IgG1:

(SEQ ID NO:3)
GCTAGCACCAAGGGCCCATCGGTCTTCCCCCTGGCACCCTCCTCCAAGAGCACCTCTGGGGG

CACAGCGGCCCTGGGCTGCCTGGTCAAGGACTACTTCCCCGAACCGGTGACGGTGTCGTGGA

ACTCAGGCGCCCTGACCAGCGGCGTGCACACCTTCCCGGCTGTCCTACAGTCCTCAGGACTC

TACTCCCTCAGCAGCGTGGTGACCGTGCCCTCCAGCAGCTTGGGCACCCAGACCTACATCTG

CAACGTGAATCACAAGCCCAGCACCAAGGTGGACAAGAAAGCAGAGCCCAAATCTTGTGACA

AAACTCACACATCCCCACCGTGCCCAGCACCTGAACTCCTGGGGGGACCGTCAGTCTTCCTC

TTCCCCCCAAAACCCAAGGACACCCTCAGGATCTCCCGGACCCCTGAGGTCACATGCGTGGT

GGTGGACGTGAGCCACGAAGACCCTGAGGTCAAGTTCAACTGGTACGTGGACGGCGTGGAGG

TGCATAATGCCAAGACAAAGCCGCGGGAGGAGCAGTACAGCACGTACCGGGTGGTCAGCGTC

CTCACCGTCCTGCACCAGGACTGGCTGAATGGCAAGGAGTACAAGTGCAAGGTCTCCAACAA

AGCCCTCCCAGCCCCCATCGAGAAAACCATCTCCAAAGCCAAAGGGCAGCCCCGAGAACCAC

AGGTGTACACCCTGCCCCCATCCCGGGATGAGCTGACCAAGAACCAGGTCAGCCTGACCTGC

CTGGTCAAAGGCTTCTATCCCAGCGACATCGCCGTGGAGTGGGAGAGCAATGGGCAGCCGGA

GAACAACTACAAGACCACGCCTCCCGTGCTGGACTCCGACGGCTCCTTCTTCCTCTACAGCA

AGCTCACCGTGGACAAGAGCAGGTGGCAGCAGGGGAACGTCTTCTCATGCTCCGTGATGCAT

GAGGCTCTGCACAACCACTACACGCAGAAGAGCCTCTCCCTGTCTCCGGGTAAATGA

Variable region of light chain (Kappa, Vκ) of 80R IgG1:

(SEQ ID NO:4)
ACGACACTCACGCAGTCTCCAGCCACCCTGTCTTTGTCTCCAGGGGAAAGGGCCACCCTCTC

CTGCAGGGCCAGTCAGAGTGTTAGGAGCAACTTAGCCTGGTACCAGCAGAAACCTGGCCAGG

CTCCCAGGCCCCTCATCTATGATGCATCCACCAGGGCCACTGGCATCCCAGACAGGTTCAGT

GGCAGTGGGTCTGGGACAGACTTCACTCTCACCATCAGCAGACTGGAGCCTGAAGATTTTGC

AGTTTATTACTGTCAGCAGCGTAGCAACTGGCCTCCGACGTTCGGCCAAGGGACCAAGGTGG

AAGTCAAA

Constant region of light chain (Kappa, Cκ) of 80R IgG1:

(SEQ ID NO:5)
GATGGTACCAAGGTGGAAATCAAACGTACGGTGGCTGCACCATCTGTCTTCATCTTCCCGCC

ATCTGATGAGCAGTTGAAATCTGGAACTGCCTCTGTTGTGTGCCTGCTGAATAACTTCTATC

CCAGAGAGGCCAAAGTACAGTGGAAGGTGGATAACGCCCTCCAATCGGGTAACTCCCAGGAG

AGTGTCACAGAGCAGGACAGCAAGGACAGCACCTACAGCCTCAGCAGCACCCTGACGCTGAG

CAAAGCAGACTACGAGAAACACAAAGTCTACGCCTGCGAAGTCACCCATCAGGGCCTGAGCT

CGCCCGTCACAAAGAGCTTCAACAGGGGAGAGTGTTGA

The amino acid sequences of the VH and VL regions of scFv antibody 80R are shown in FIG. 1 along with the amino acid sequences of other scFvs identified according to the methods of the invention.

Binding kinetic rates ($k_{on}$ and $k_{off}$) and affinities ($K_a$ and $K_d$) of 80R scFv, monoclonal antibody 80R and ACE2 receptor for S1-Ig were measured using the BIAcore-evaluation software. (See Example 6, infra). As shown in Table 2, monoclonal antibody 80R had a 20-fold increase ($K_d$=1.59 nM) in binding affinity to S1 over its parental 80R scFv ($K_d$=32.3 nM). Moreover, this binding affinity is comparable to that of the receptor ACE2 ($K_d$=1.70 nM).

TABLE 2

Kinetic rates and binding affinity of 80R scFv, monoclonal antibody 80R and ACE2 to S1-Ig.

| | $k_{on}$ (M$^{-1}$s$^{-1}$) | $k_{off}$ (s$^{-1}$) | $K_a$ (M$^{-1}$) | $K_d$ (M) |
|---|---|---|---|---|
| 80R scFv | $2.29 \times 10^5$ | $8.36 \times 10^{-3}$ | $3.10 \times 10^7$ | $3.23 \times 10^{-8}$ |
| 80R IgG1 | $3.88 \times 10^5$ | $6.18 \times 10^{-4}$ | $6.28 \times 10^8$ | $1.59 \times 10^{-9}$ |
| ACE2 | $2.47 \times 10^5$ | $4.20 \times 10^{-4}$ | $5.88 \times 10^8$ | $1.70 \times 10^{-9}$ |

Those skilled in the art will recognize that additional scFvs and monoclonal antibodies having different binding affinities may also be therapeutically effective. For example, antibodies and scFvs having binding affinities ranging from about $10^{-6}$ M to about $10^{-12}$ M may also be therapeutically effective.

Figure 2B:
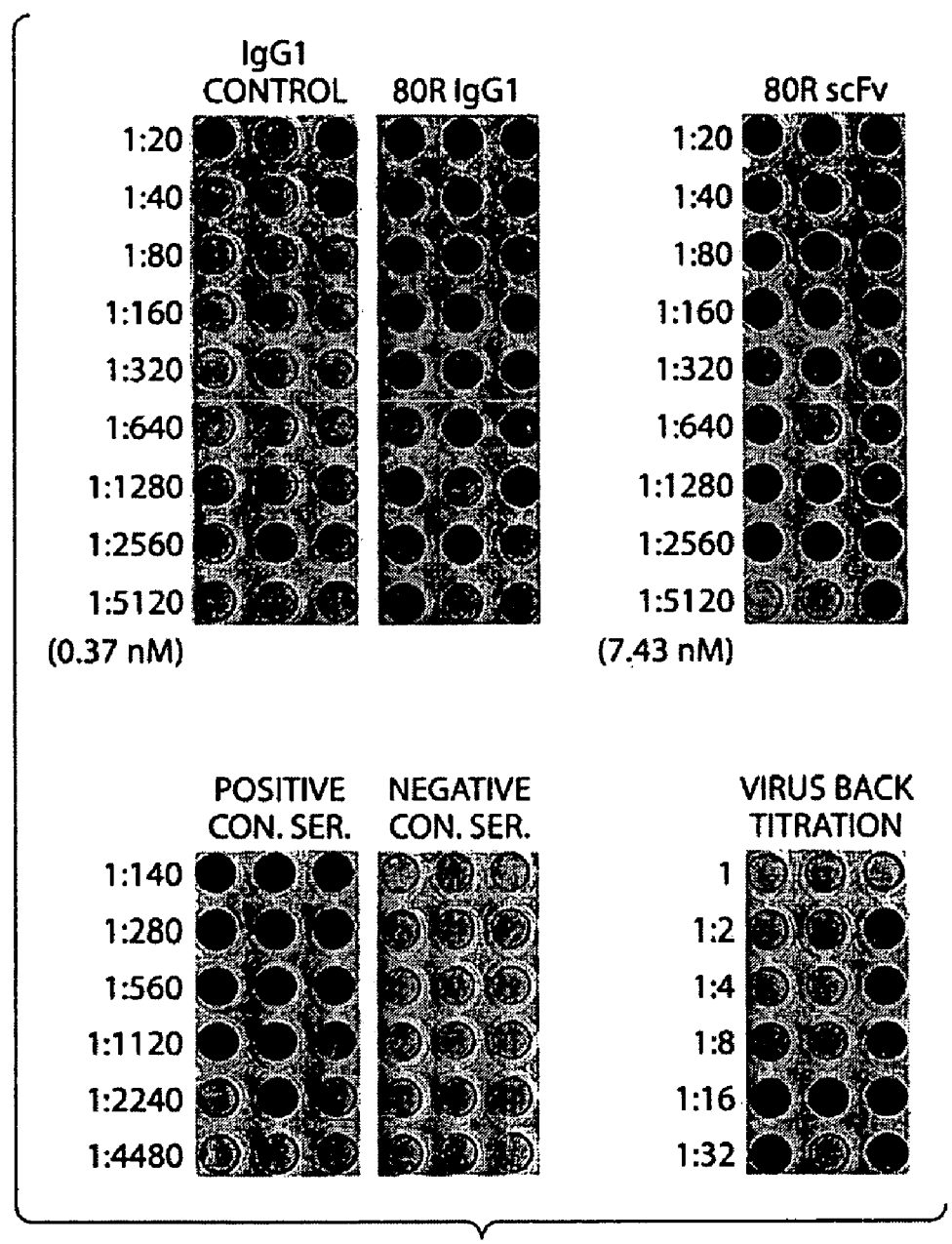
FIG. 2B shows the comparison of the neutralization activity of 80R scFv and full length 80R IgG1. The positive and negative control serum samples and the amount of virus used were the same as used in FIG. 2A. The titer and concentration of antibodies are labeled on the left.

In further micro-neutralization assays, as demonstrated in FIG. 2B, monoclonal antibody 80R was 20-fold more effective than 80R scFv on a molar basis comparison, which was consistent with its superior affinity (See FIG. 2B). At a concentration of 7.43 nM, 80R scFv can neutralize greater than 50% of the testing wells from infection, while the same neutralizing activity was achieved by 80R IgG1 at a concentration as low as 0.37 nM.

Figure 3:
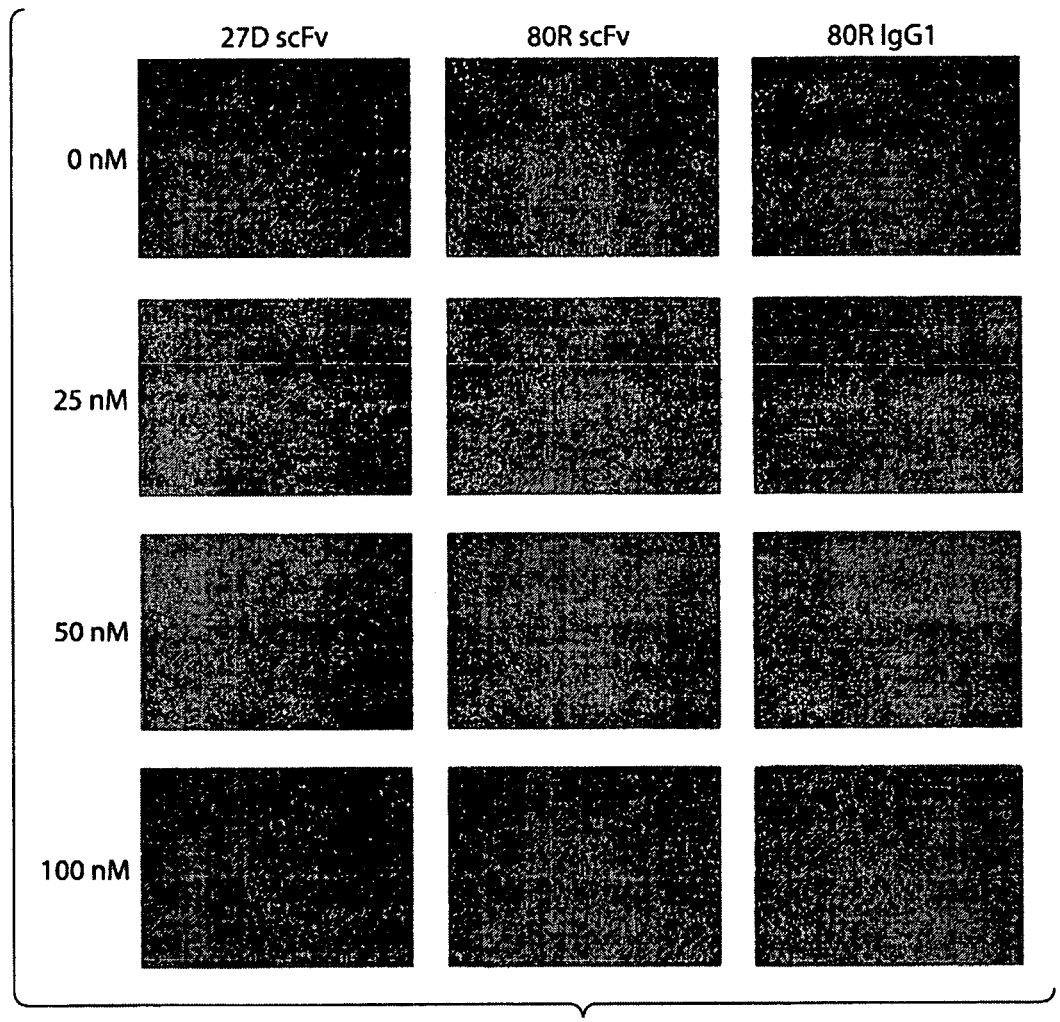
FIG. 3 is a series of photographs showing inhibition of syncytia formation by anti-S1 antibodies. A syncytia formation assay was performed using the anti-S1 antibodies. 293T cells expressing SARS-CoV S protein were pre-incubated with the indicated concentrations of anti-S1 scFvs or 80R IgG1 and then mixed with 293T cells expressing ACE2 (the SARS-CoV receptor). After culturing 36 hours in the presence of antibodies, dose dependent inhibition of syncytia formation by 80R scFv and 80R IgG1 were observed and photographed. Representative results are shown in FIG. 3.

Because SARS-CoV S protein expressing 293T cells can fuse with receptor ACE2 expressing 293T cells to form multinucleated syncytia, syncytia formation inhibition assays were performed with all eight anti-S1 scFvs and with monoclonal antibody 80R. Consistent with the neutralization results discussed above, 80R was the only scFv that inhibited syncytia formation. Moreover, as shown in FIG. 3, 80R IgG1 was more potent in blocking syncytia formation than 80R scFv.

Figure 4A:
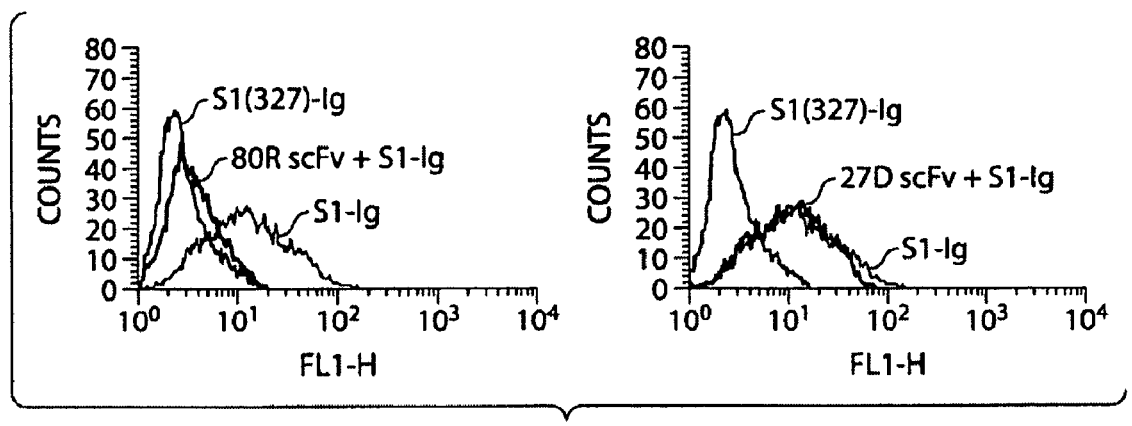
FIG. 4A are flow cytometry histograms showing staining of Vero E6 with S1-Ig and flow cytometry analysis. The dotted line represents control staining with S1 (327)-Ig; the thin line represents cells that were stained with S1-Ig; and the bold line represents staining with pre-mix of 0.3 μg S1-Ig and 0.3 μg of 80R scFv (left panel) or 27D scFv (right panel).
Figure 4B:
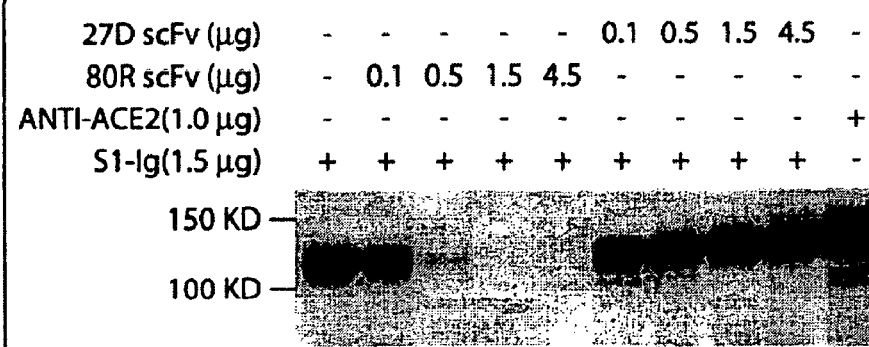
FIG. 4B shows scFv competition of S1-Ig binding to the ACE2 receptor in immunoprecipitation. Radiolabeled ACE2 was immunoprecipitated by S1-Ig that was preincubated with the indicated amounts of either 27D scFv or 80R scFv. Anti-ACE2 precipitates were used as a positive control. Immunoprecipiates were run on a reducing SDS-PAGE gel and visualized by autoradiography.

Thus, it was hypothesized that the mechanism by which 80R neutralizes SARS-CoV could be the direct inhibition of virus attachment to cell membrane through blocking binding of S1 to ACE2. To confirm this hypothesis directly, it was examined whether the 80R scFv could inhibit the binding of S1 to ACE2 expressing Vero E6 cells. As shown in FIG. 4A, when Vero E6 cells were incubated with S1-Ig in the presence of 80R scFv and analyzed by flow cytometry, 80R scFv completely inhibited the binding of S1-Ig to Vero E6 cells at a concentration of 15 µg/ml (about 5 times greater molar concentration than S1-Ig). A non-neutralizing antibody (27D) did not inhibit the binding under the same conditions. S1 (327)-Ig, which is not part of the receptor binding domain (see Li W et al., Nature 426:450-54 (2003)), was used as a control for S1-Ig specific binding to Vero E6 cells. The binding of S1-Ig to metabolically labeled soluble ACE2 was specifically inhibited by 80R scFv in a dose dependent manner (See FIG. 4B). Thus, a primary mechanism of the neutralizing activity of 80R occurs through blocking of S1 binding to ACE2.

Characterization of the 80R Epitope.

Figure 5:
FIG. 5 is a Western blot of S1-Ig using 80R scFv. Non-reduced, reduced or de-glycosylated S1-Ig were subjected to 10% SDS-PAGE gel, transferred to nitrocellulose membrane, and detected with anti-S1 80R scFv, followed by rabbit anti-His$_6$ Ig and HRP-labeled anti-rabbit IgG. 80R scFv recognized non-reduced S1 much stronger than reduced S1, and there was no further significant decrease of antibody binding to de-glycosylated S1 as compared to reduced S1.

Primary epitope mapping of 80R binding region on S1 showed that 80R did not recognize the N-terminal residues 12-327 of S1 domain, but demonstrated that 80R bound to the C-terminal residues of 261-672 and that the neutralizing activity of 80R was achieved by blocking the association of S protein to its cellular receptor ACE2. This binding was comparable to that of the full length of S1 domain by ELISA. In addition, 80R can recognize SDS-denatured, DTT reduced and PNGase F deglycosylated S1 in an immunoblotting assay (see FIG. 5), although binding is greater under non-reduced conditions. These results of the primary characterization suggest that the 80R epitope is more sensitive to reduction, more resistant to denaturation and independent of glycosylation.

80R Neutralizing Determinants are Located within the

ACE2 Receptor Binding Domain on SARS-CoV S Protein

A 193-aa region consisting of residues 318-510 of the S1 domain, was recently shown to contain the ACE2 receptor binding domain of the SARS-CoV S protein. (see Wong et al., J Biol Chem 279:3197-201 (2003)). Two truncation variants expressing fragments smaller than this 193-aa fragment (e.g., residues 318-490 and 327-510) did not bind to ACE2 by radioimmunoprecipitation. Thus, in order to more precisely map the binding domain of 80R, and to better understand how 80R blocks the binding of S protein to ACE2, the ability of these three fragments of the S1 domain (residues 318-510, 318-490 and 327-510) to bind to 80R was examined. See Example 11, infra.

The resulting data indicate that the 80R neutralizing determinant and the ACE2 receptor-binding domain are located within the same domain of the S protein, specifically, between residues 318 and 510. Smaller N-terminal and smaller C-terminal deletion variants of this domain (318-490 and 327-510, respectively) lost 80R-binding activity, which implies that some residues in the N-terminal and C-terminal of S1(318 to 510) contribute either directly to the binding of 80R with this domain or to the folding of the correct antibody-binding domain. In addition, these studies also demonstrate that the neutralizing epitope of MAb80R is absolutely conformationally dependent. The smallest 80R binding domain is located within amino acids 324-503.

Identification of Important Residues for 80R Binding to the ACE2 Receptor-Binding Domain of S1 Protein Some acidic residues between amino acid residues 318 and 510 (glutamic acid 452 and aspartic acid 454, 463 and 480) were individually substituted to alanine to test their effect on association with ACE2. It was shown that E452 and D454 individually made important contributions to the S1 interaction with ACE2. D463A alteration also resulted in a decrease of ACE2 binding, but no effect was found with a D480A alteration. (See Wong et al, J Biol Chem 279:3197-201 (2004)).

These point-substitution variants were also tested for 80R antibody binding. See Example 11, infra. Specifically, they were individually mutated to alanine in both S1 (318-510)-Ig and in full-length S1-Ig. The resulting data demonstrated that E452 and D454 contribute to the association of S1 protein with 80R antibody similarly to the association of S1 with ACE2. D463 does not affect 80R binding to S1, but affects the association of ACE2 to S1. D480 plays no significant role in S protein association with ACE2, but is critically important for 80R-antibody binding, as this substitution abolished binding to MAb 80R. These data suggest that the S1 regions involved in receptor- and neutralizing antibody-binding are, in part, overlapping.

80R Binding Characteristics of Variant S Proteins with Amino Acid Substitutions in the 80R-Binding Domain that Occur in SARS-Like-CoV from Civet Cats and that Evolved During Recent SARS Outbreaks To test whether the sequence variations in the 80R antibody binding domain presented in Table 1 could be associated with significant changes in the binding activity of 80R, the 80R antibody was originally screened against the S1 domain of S protein of a late phase human SARS-CoV isolate (Tor2, NC_004718). For substitution analysis, each amino acid in Tor2 was individually replaced with a corresponding changed amino acid in order to examine the effect of these residues on 80R antibody binding. For example, K (Tor2) at position 344 was replaced with R (Civet SARS-like-CoV, isolate SZ3). Each amino acid was also substituted with alanine to investigate whether these residues normally contribute to form the 80R epitope.

Figure 8A:
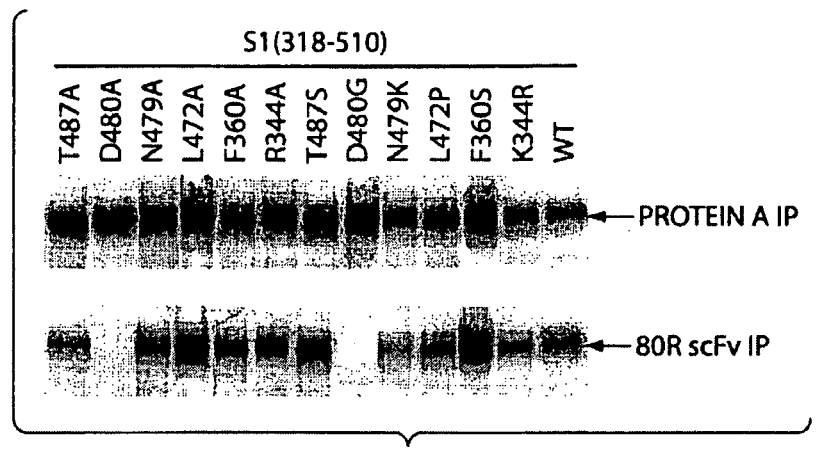
FIGS. 8A-8C show the effects on 80R binding of variant amino-acid substitutions of S protein that occur in animal SARS-like-CoVs and human SARS-CoVs.

As shown in FIG. 8A, no effect on the binding of 80R was found for the variants of either F360S and L472P or F360A and L472A in S1(318-510) and no significant changes in binding were observed with the variants K344R and T487S. However, mutation to alanine with the variants R344A and T487A resulted in ~20% and ~50% reductions in binding, respectively. At position 479, N479K substitution resulted in a ~50% decrease in 80R binding, whereas N479A substitution resulted in only ~20% reduction.

Figure 9A:
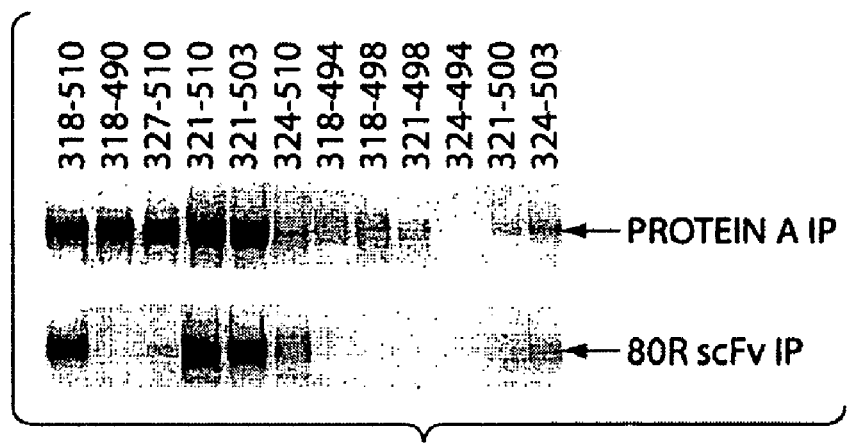
FIGS. 9A and 9B show the results obtained when truncations and point mutations of S1 (318-510) were analyzed to define the 80R antibody epitope. S1 residues 318-510 fused to the Fc region of human IgG1, and truncation or mutation variants of S1(318-510) containing indicated residues were metabolically labeled and precipitated by Protein A or 80R scFv.
Figure 9B:
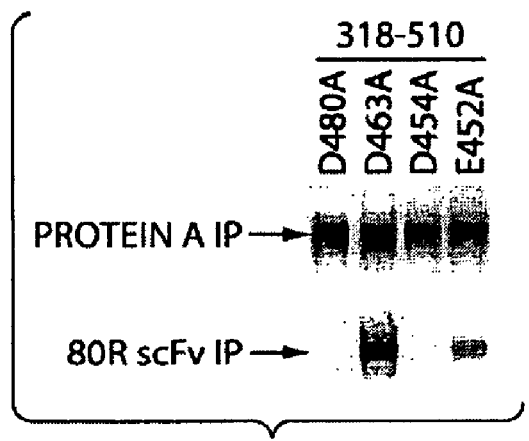

These results implied that lysine 344, asparagine 479 and threonine 487 normally contribute in some degree to the binding of 80R to the S1 domain, either by forming part of the 80R binding site, or by facilitating correct folding of the protein. As shown in FIGS. 9B and 8A, D480A substitution completely abolished binding to 80R. The same result was observed when aspartic acid was changed to glycine at position 480 of the sequence of the 2003/2004 Guangdong index patient GD03T.

Figure 8B:
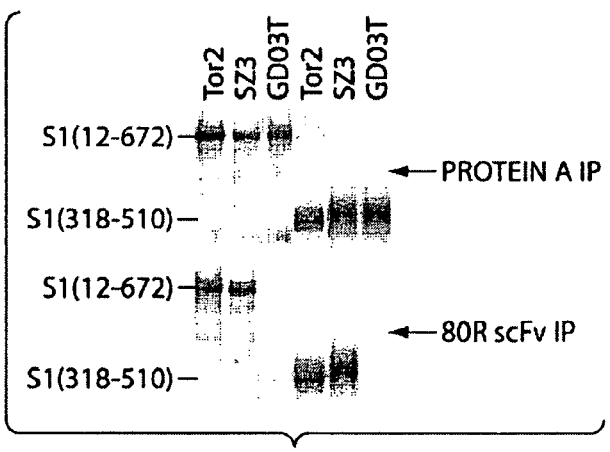

In addition, S1(318-510)-Ig corresponding to the civet SZ3 and human GD03T viral isolates was also made by introducing multiple amino acid substitutions 344R/360S/479K/487S for civet SZ3 and 344R/360S/472P/480G/487S for human GD03T in the Tor2 S1 (318-510)-Ig construct. Also, the full-length S1 genes (12-672) encoding the entire S1 protein of civet SZ3 and human GD03T were synthesized de novo for the entire human SARS-CoV S1 protein of the Tor2 isolate (see Li et al., Nature 426:450-54 (2003)). These two full-length S1 variants include amino-acid changes in residues 318-510, as well as changes outside this region. Both S1(318-510) and S1(12-672) of civet SZ3 bound to 80R similarly as did Tor2 (FIG. 8B).

The variant containing the single amino-acid substitution N479K, which reduced binding to 80R, did not appear to affect binding in the context of the multiply substituted variant. Neither the S1(318-510) nor the S1(12-672) of GD03T bound to 80R scFv. This is consistent with the critical role of D480 in the binding of 80R to S1 protein. A D480G change in the S protein of GD03T conferred complete resistance to 80R scFv.

Figure 8C:
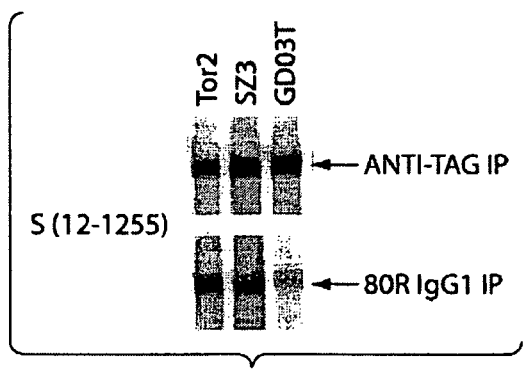

Finally, the effect of these alterations for binding to 80R IgG1 in context of the full-length S protein was also evaluated. As shown in FIG. 8C, consistent with the binding of S fragment of RBD and S1 to 80R scFv, 80R IgG1 efficiently precipitated the full-length S proteins of Tor2 and SZ3, but not GD03T, although very weak binding of GD03T to 80R IgG1 was traced due to much higher affinity of 80R IgG1 over 80R scFv.

These critical amino acids for the 80R epitope were not found to vary among the human SARS-CoVs isolated from the 2002/2003 epidemic. Therefore, the vast majority of SARS-CoV isolated to date are likely to be sensitive to MAb 80R.

Described below are the results of a screening assay using a preparation of cellulose membranes that had bound 4942 linear peptides spanning the entire SARS-CoV genome. These membranes had been previously used to probe acute and convalescent sera from four cases of patients with SARS. See Guo et al., Virology 324:251-56 (2004), incorporated herein by reference. A subset of the 4942 linear peptides representing Spike protein peptides of 10 amino acids in length that overlap by 8 residues were synthesized onto these membranes, but did not bind to MAb 80R. Based on the results of the SARS-CoV epitope mapping data, as described in FIG. 9A, additional conformational peptides were synthesized.

Specifically, peptides were synthesized that had amino acids at the N-terminus (approximately residues 318-424 of the S1 protein) and at the C-terminus (approximately residues 503-510) of a loop. Spacers of different lengths were inserted between the flanking regions. Two peptides were shown to bind to MAb 80R. These peptides are: RVVVLSFELGPPG-GPFGEVF (SEQ ID NO:31) and VVVSFELNLCPFGE (SEQ ID NO:32). These results imply that the region between the flanking residues can vary by between 3 and 5 amino acids. For example, the best sequences for designing peptides that will produce antibodies like 80R are likely SFELxxx-PFGE (SEQ ID NO:33) or SFELxxxxxPFGE (SEQ ID NO:34) in forward or reverse orientation.

Antibodies

As used herein, the term "antibody" refers to immunoglobulin molecules and immunologically active portions of immunoglobulin (Ig) molecules, i.e., molecules that contain an antigen binding site that specifically binds (immunoreacts with) an antigen. By "specifically binds" or "immunoreacts with" is meant that the antibody reacts with one or more antigenic determinants of the desired antigen and does not react with other polypeptides. Antibodies include, but are not limited to, polyclonal, monoclonal, chimeric, dAb (domain antibody), single chain, $F_{ab}$, $F_{ab'}$ and $F_{(ab')2}$ fragments, scFvs, and $F_{ab}$ expression libraries.

A single chain Fv ("scFv") polypeptide molecule is a covalently linked VH::VL heterodimer, which can be expressed from a gene fusion including $V_{H-}$ and $V_{L-}$ encoding genes linked by a peptide-encoding linker. (See Huston et al. (1988) Proc Nat Acad Sci USA 85(16):5879-5883). A number of methods have been described to discern chemical structures for converting the naturally aggregated, but chemically separated, light and heavy polypeptide chains from an antibody V region into an scFv molecule, which will fold into a three dimensional structure substantially similar to the structure of an antigen-binding site. See, e.g., U.S. Pat. Nos. 5,091,513; 5,132,405; and 4,946,778.

Very large naïve human scFv libraries have been and can be created to offer a large source of rearranged antibody genes against a plethora of target molecules. Smaller libraries can be constructed from individuals with infectious diseases in order to isolate disease-specific antibodies. (See Barbas et al., Proc. Natl. Acad. Sci. USA 89:9339-43 (1992); Zebedee et al., Proc. Natl. Acad. Sci. USA 89:3175-79 (1992)).

In general, antibody molecules obtained from humans relate to any of the classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain.

The term "antigen-binding site," or "binding portion" refers to the part of the immunoglobulin molecule that participates in antigen binding. The antigen binding site is formed by amino acid residues of the N-terminal variable ("V") regions of the heavy ("H") and light ("L") chains. Three highly divergent stretches within the V regions of the heavy and light chains, referred to as "hypervariable regions," are interposed between more conserved flanking stretches known as "framework regions," or "FRs". Thus, the term "FR" refers to amino acid sequences which are naturally found between, and adjacent to, hypervariable regions in immunoglobulins. In an antibody molecule, the three hypervariable regions of a light chain and the three hypervariable regions of a heavy chain are disposed relative to each other in three dimensional space to form an antigen-binding surface. The antigen-binding surface is complementary to the three-dimensional surface of a bound antigen, and the three hypervariable regions of each of the heavy and light chains are referred to as "complementarity-determining regions," or "CDRs."

As shown in FIG. 1, CDR1 of the VH region of the 80R heavy chain has the sequence: AH; CDR2 of the VH region of the 80R heavy chain has the sequence: VYDNK (SEQ ID NO: 35); CDR3 of the VH region of the 80R heavy chain has the sequence: RSYYL (SEQ ID NO:36); CDR1 of the VL region of the 80R light chain has the sequence RASQVRSNLA (SEQ ID NO:37); CDR2 of the VL region of the 80R light chain has the sequence: DASTAT (SEQ ID NO:38); and CDR3 of the VL region of the 80R light chain has the sequence: QQRSNWPPT (SEQ ID NO:39).

As used herein, the term "epitope" includes any protein determinant capable of specific binding to an immunoglobulin, an scFv, or a T-cell receptor. Epitopic determinants usually consist of chemically active surface groupings of molecules such as amino acids or sugar side chains and usually have specific three dimensional structural characteristics, as well as specific charge characteristics. For example, antibodies may be raised against N-terminal or C-terminal peptides of a polypeptide.

As used herein, the terms "immunological binding," and "immunological binding properties" refer to the non-covalent interactions of the type which occur between an immunoglobulin molecule and an antigen for which the immunoglobulin is specific. The strength, or affinity of immunological binding interactions can be expressed in terms of the dissociation constant ($K_d$) of the interaction, wherein a smaller $K_d$ represents a greater affinity. Immunological binding properties of selected polypeptides can be quantified using methods well known in the art. One such method entails measuring the rates of antigen-binding site/antigen complex formation and dissociation, wherein those rates depend on the concentrations of the complex partners, the affinity of the interaction, and geometric parameters that equally influence the rate in both directions. Thus, both the "on rate constant" ($K_{on}$) and the "off rate constant" ($K_{off}$) can be determined by calculation of the concentrations and the actual rates of association and dissociation. (See Nature 361:186-87 (1993)). The ratio of $K_{off}/K_{on}$ enables the cancellation of all parameters not related to affinity, and is equal to the dissociation constant $K_d$. (See, generally, Davies et al. (1990) Annual Rev Biochem 59:439-473). An antibody of the present invention is said to specifically bind to a SARS-CoV epitope when the equilibrium binding constant ($K_d$) is $\leq 1$ μM, preferably $\leq 100$ nM, more preferably $\leq 10$ nM, and most preferably $\leq 100$ pM to about 1 pM, as measured by assays such as radioligand binding assays or similar assays known to those skilled in the art.

A SARS-CoV protein (e.g., S1, S2 or M) of the invention, or a derivative, fragment, analog, homolog or ortholog thereof, may be utilized as an immunogen in the generation of antibodies that immunospecifically bind these protein components.

Those skilled in the art will recognize that it is possible to determine, without undue experimentation, if a human monoclonal antibody has the same specificity as a human monoclonal antibody of the invention (e.g., monoclonal antibody 80R) by ascertaining whether the former prevents the latter from binding to the S1 region of SARS-CoV. If the human monoclonal antibody being tested competes with the human monoclonal antibody of the invention, as shown by a decrease in binding by the human monoclonal antibody of the invention, then it is likely that the two monoclonal antibodies bind to the same, or to a closely related, epitope.

Another way to determine whether a human monoclonal antibody has the specificity of a human monoclonal antibody of the invention is to pre-incubate the human monoclonal antibody of the invention with the SARS-CoV S1 protein, with which it is normally reactive, and then add the human monoclonal antibody being tested to determine if the human monoclonal antibody being tested is inhibited in its ability to bind the S1 region. If the human monoclonal antibody being tested is inhibited then, in all likelihood, it has the same, or functionally equivalent, epitopic specificity as the monoclonal antibody of the invention. Screening of human monoclonal antibodies of the invention, can be also carried out by utilizing SARS-CoV and determining whether the test monoclonal antibody is able to neutralize SARS-CoV.

Various procedures known within the art may be used for the production of polyclonal or monoclonal antibodies directed against a protein of the invention, or against derivatives, fragments, analogs homologs or orthologs thereof. (See, for example, Antibodies: A Laboratory Manual, Harlow E, and Lane D, 1988, Cold Spring Harbor Laboratory Press, Cold Spring Harbor, N.Y., incorporated herein by reference).

Antibodies can be purified by well-known techniques, such as affinity chromatography using protein A or protein G, which provide primarily the IgG fraction of immune serum. Subsequently, or alternatively, the specific antigen which is the target of the immunoglobulin sought, or an epitope thereof, may be immobilized on a column to purify the immune specific antibody by immunoaffinity chromatography. Purification of immunoglobulins is discussed, for example, by D. Wilkinson (The Scientist, published by The Scientist, Inc., Philadelphia Pa., Vol. 14, No. 8 (Apr. 17, 2000), pp. 25-28).

The term "monoclonal antibody" or "MAb" or "monoclonal antibody composition", as used herein, refers to a population of antibody molecules that contain only one molecular species of antibody molecule consisting of a unique light chain gene product and a unique heavy chain gene product. In particular, the complementarity determining regions (CDRs) of the monoclonal antibody are identical in all the molecules of the population. MAbs contain an antigen binding site capable of immunoreacting with a particular epitope of the antigen characterized by a unique binding affinity for it.

Monoclonal antibodies can be prepared using hybridoma methods, such as those described by Kohler and Milstein, Nature, 256:495 (1975). In a hybridoma method, a mouse, hamster, or other appropriate host animal, is typically immunized with an immunizing agent to elicit lymphocytes that produce or are capable of producing antibodies that will specifically bind to the immunizing agent. Alternatively, the lymphocytes can be immunized in vitro.

The immunizing agent will typically include the protein antigen, a fragment thereof or a fusion protein thereof. Generally, either peripheral blood lymphocytes are used if cells of human origin are desired, or spleen cells or lymph node cells are used if non-human mammalian sources are desired. The lymphocytes are then fused with an immortalized cell line using a suitable fusing agent, such as polyethylene glycol, to form a hybridoma cell (Goding, *Monoclonal Antibodies: Principles and Practice*, Academic Press, (1986) pp. 59-103). Immortalized cell lines are usually transformed mammalian cells, particularly myeloma cells of rodent, bovine and human origin. Usually, rat or mouse myeloma cell lines are employed. The hybridoma cells can be cultured in a suitable culture medium that preferably contains one or more substances that inhibit the growth or survival of the unfused, immortalized cells. For example, if the parental cells lack the enzyme hypoxanthine guanine phosphoribosyl transferase (HGPRT or HPRT), the culture medium for the hybridomas typically will include hypoxanthine, aminopterin, and thymidine ("HAT medium"), which substances prevent the growth of HGPRT-deficient cells.

Preferred immortalized cell lines are those that fuse efficiently, support stable high level expression of antibody by the selected antibody-producing cells, and are sensitive to a medium such as HAT medium. More preferred immortalized cell lines are murine myeloma lines, which can be obtained, for instance, from the Salk Institute Cell Distribution Center, San Diego, Calif. and the American Type Culture Collection, Manassas, Va. Human myeloma and mouse-human heteromyeloma cell lines also have been described for the production of human monoclonal antibodies. (See Kozbor, J. Immunol., 133:3001 (1984); Brodeur et al., Monoclonal Antibody Production Techniques and Applications, Marcel Dekker, Inc., New York, (1987) pp. 51-63)).

The culture medium in which the hybridoma cells are cultured can then be assayed for the presence of monoclonal antibodies directed against the antigen. Preferably, the binding specificity of monoclonal antibodies produced by the hybridoma cells is determined by immunoprecipitation or by an in vitro binding assay, such as radioimmunoassay (RIA) or enzyme-linked immunoabsorbent assay (ELISA). Such techniques and assays are known in the art. The binding affinity of the monoclonal antibody can, for example, be determined by the Scatchard analysis of Munson and Pollard, Anal. Biochem., 107:220 (1980). Moreover, in therapeutic applications of monoclonal antibodies, it is important to identify antibodies having a high degree of specificity and a high binding affinity for the target antigen.

After the desired hybridoma cells are identified, the clones can be subcloned by limiting dilution procedures and grown by standard methods. (See Goding, *Monoclonal Antibodies: Principles and Practice*, Academic Press, (1986) pp. 59-103). Suitable culture media for this purpose include, for example, Dulbecco's Modified Eagle's Medium and RPMI-1640 medium. Alternatively, the hybridoma cells can be grown in vivo as ascites in a mammal.

The monoclonal antibodies secreted by the subclones can be isolated or purified from the culture medium or ascites fluid by conventional immunoglobulin purification procedures such as, for example, protein A-Sepharose, hydroxylapatite chromatography, gel electrophoresis, dialysis, or affinity chromatography.

Monoclonal antibodies can also be made by recombinant DNA methods, such as those described in U.S. Pat. No. 4,816,567. DNA encoding the monoclonal antibodies of the invention can be readily isolated and sequenced using conventional procedures (e.g., by using oligonucleotide probes that are capable of binding specifically to genes encoding the heavy and light chains of murine antibodies). The hybridoma cells of the invention serve as a preferred source of such DNA. Once isolated, the DNA can be placed into expression vectors, which are then transfected into host cells such as simian COS cells, Chinese hamster ovary (CHO) cells, or myeloma cells that do not otherwise produce immunoglobulin protein, to obtain the synthesis of monoclonal antibodies in the recombinant host cells. The DNA also can be modified, for example, by substituting the coding sequence for human heavy and light chain constant domains in place of the homologous murine sequences (see U.S. Pat. No. 4,816,567; Morrison, Nature 368, 812-13 (1994)) or by covalently joining to the immunoglobulin coding sequence all or part of the coding sequence for a non-immunoglobulin polypeptide. Such a non-immunoglobulin polypeptide can be substituted for the constant domains of an antibody of the invention, or can be substituted for the variable domains of one antigen-combining site of an antibody of the invention to create a chimeric bivalent antibody.

Fully human antibodies are antibody molecules in which the entire sequence of both the light chain and the heavy chain, including the CDRs, arise from human genes. Such antibodies are termed "human antibodies", or "fully human antibodies" herein. Human monoclonal antibodies can be prepared by using trioma technique; the human B-cell hybridoma technique (see Kozbor, et al., 1983 Immunol Today 4: 72); and the EBV hybridoma technique to produce human monoclonal antibodies (see Cole, et al., 1985 In: MONOCLONAL ANTIBODIES AND CANCER THERAPY, Alan R. Liss, Inc., pp. 77-96). Human monoclonal antibodies may be utilized and may be produced by using human hybridomas (see Cote, et al., 1983. Proc Natl Acad Sci USA 80: 2026-2030) or by transforming human B-cells with Epstein Barr Virus in vitro (see Cole, et al., 1985 In: MONOCLONAL ANTIBODIES AND CANCER THERAPY, Alan R. Liss, Inc., pp. 77-96).

In addition, human antibodies can also be produced using additional techniques, including phage display libraries. (See Hoogenboom and Winter, J. Mol. Biol., 227:381 (1991); Marks et al., J. Mol. Biol., 222:581 (1991)). Similarly, human antibodies can be made by introducing human immunoglobulin loci into transgenic animals, e.g., mice in which the endogenous immunoglobulin genes have been partially or completely inactivated. Upon challenge, human antibody production is observed, which closely resembles that seen in humans in all respects, including gene rearrangement, assembly, and antibody repertoire. This approach is described, for example, in U.S. Pat. Nos. 5,545,807; 5,545,806; 5,569,825; 5,625,126; 5,633,425; 5,661,016, and in Marks et al., Bio/Technology 10, 779-783 (1992); Lonberg et al., Nature 368 856-859 (1994); Morrison, Nature 368, 812-13 (1994); Fishwild et al, Nature Biotechnology 14, 845-51 (1996); Neuberger, Nature Biotechnology 14, 826 (1996); and Lonberg and Huszar, Intern. Rev. Immunol. 13 65-93 (1995).

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the Xenomouse™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

Human antibodies may additionally be produced using transgenic nonhuman animals which are modified so as to produce fully human antibodies rather than the animal's endogenous antibodies in response to challenge by an antigen. (See PCT publication WO94/02602). The endogenous genes encoding the heavy and light immunoglobulin chains in the nonhuman host have been incapacitated, and active loci encoding human heavy and light chain immunoglobulins are inserted into the host's genome. The human genes are incorporated, for example, using yeast artificial chromosomes containing the requisite human DNA segments. An animal which provides all the desired modifications is then obtained as progeny by crossbreeding intermediate transgenic animals containing fewer than the full complement of the modifications. The preferred embodiment of such a nonhuman animal is a mouse, and is termed the XENOMOUSE™ as disclosed in PCT publications WO 96/33735 and WO 96/34096. This animal produces B cells which secrete fully human immunoglobulins. The antibodies can be obtained directly from the animal after immunization with an immunogen of interest, as, for example, a preparation of a polyclonal antibody, or alternatively from immortalized B cells derived from the animal, such as hybridomas producing monoclonal antibodies. Additionally, the genes encoding the immunoglobulins with human variable regions can be recovered and expressed to obtain the antibodies directly, or can be further modified to obtain analogs of antibodies such as, for example, single chain Fv (scFv) molecules.

One method for producing an antibody of interest, such as a human antibody, is disclosed in U.S. Pat. No. 5,916,771. This method includes introducing an expression vector that contains a nucleotide sequence encoding a heavy chain into one mammalian host cell in culture, introducing an expression vector containing a nucleotide sequence encoding a light chain into another mammalian host cell, and fusing the two cells to form a hybrid cell. The hybrid cell expresses an antibody containing the heavy chain and the light chain.

In a further improvement on this procedure, a method for identifying a clinically relevant epitope on an immunogen, and a correlative method for selecting an antibody that binds immunospecifically to the relevant epitope with high affinity, are disclosed in PCT publication WO 99/53049.

The antibody can be expressed by a vector containing a DNA segment encoding the single chain antibody described above.

These can include vectors, liposomes, naked DNA, adjuvant-assisted DNA, gene gun, catheters, etc. Vectors include chemical conjugates such as described in WO 93/64701, which has targeting moiety (e.g. a ligand to a cellular surface receptor), and a nucleic acid binding moiety (e.g. polylysine), viral vector (e.g. a DNA or RNA viral vector), fusion proteins such as described in PCT/US 95/02140 (WO 95/22618) which is a fusion protein containing a target moiety (e.g. an antibody specific for a target cell) and a nucleic acid binding moiety (e.g. a protamine), plasmids, phage, etc. The vectors can be chromosomal, non-chromosomal or synthetic.

Preferred vectors include viral vectors, fusion proteins and chemical conjugates. Retroviral vectors include moloney murine leukemia viruses. DNA viral vectors are preferred. These vectors include pox vectors such as orthopox or avipox vectors, herpesvirus vectors such as a herpes simplex I virus (HSV) vector (see Geller, A. I. et al., J. Neurochem, 64:487 (1995); Lim, F., et al., in DNA Cloning: Mammalian Systems, D. Glover, Ed. (Oxford Univ. Press, Oxford England) (1995); Geller, A. I. et al., Proc Natl. Acad. Sci.: U.S.A. 90:7603 (1993); Geller, A. I., et al., Proc Natl. Acad. Sci. USA 87:1149 (1990), Adenovirus Vectors (see LeGal LaSalle et al., Science, 259:988 (1993); Davidson, et al., Nat. Genet 3:219 (1993); Yang, et al., J. Virol. 69:2004 (1995) and Adeno-associated Virus Vectors (see Kaplitt, M. G. et al., Nat. Genet. 8:148 (1994).

Pox viral vectors introduce the gene into the cells cytoplasm. Avipox virus vectors result in only a short term expression of the nucleic acid. Adenovirus vectors, adeno-associated virus vectors and herpes simplex virus (HSV) vectors are preferred for introducing the nucleic acid into neural cells. The adenovirus vector results in a shorter term expression (about 2 months) than adeno-associated virus (about 4 months), which in turn is shorter than HSV vectors. The particular vector chosen will depend upon the target cell and the condition being treated. The introduction can be by standard techniques, e.g. infection, transfection, transduction or transformation. Examples of modes of gene transfer include e.g., naked DNA, $CaPO_4$ precipitation, DEAE dextran, electroporation, protoplast fusion, lipofection, cell microinjection, and viral vectors.

The vector can be employed to target essentially any desired target cell. For example, stereotaxic injection can be used to direct the vectors (e.g. adenovirus, HSV) to a desired location. Additionally, the particles can be delivered by intracerebroventricular (icv) infusion using a minipump infusion system, such as a SynchroMed Infusion System. A method based on bulk flow, termed convection, has also proven effective at delivering large molecules to extended areas of the brain and may be useful in delivering the vector to the target cell. (See Bobo et al., Proc. Natl. Acad. Sci. USA 91:2076-2080 (1994); Morrison et al., Am. J. Physiol. 266: 292-305 (1994)). Other methods that can be used include catheters, intravenous, parenteral, intraperitoneal and subcutaneous injection, and oral or other known routes of administration.

These vectors can be used to express large quantities of antibodies that can be used in a variety of ways. For example, to detect the presence of SARS-CoV in a sample. The antibody can also be used to try to bind to and disrupt SARS-CoV Interaction with the SARS-CoV receptor ACE2.

Techniques can be adapted for the production of single-chain antibodies specific to an antigenic protein of the invention (see e.g., U.S. Pat. No. 4,946,778). In addition, methods can be adapted for the construction of $F_{ab}$ expression libraries (see e.g., Huse, et al., 1989 Science 246: 1275-1281) to allow rapid and effective identification of monoclonal $F_{ab}$ fragments with the desired specificity for a protein or derivatives, fragments, analogs or homologs thereof. Antibody fragments that contain the idiotypes to a protein antigen may be produced by techniques known in the art including, but not limited to: (i) an $F_{(ab')2}$ fragment produced by pepsin digestion of an antibody molecule; (ii) an $F_{ab}$ fragment generated by reducing the disulfide bridges of an $F_{(ab')2}$ fragment; (iii)

an $F_{ab}$ fragment generated by the treatment of the antibody molecule with papain and a reducing agent and (iv) $F_v$ fragments.

Heteroconjugate antibodies are also within the scope of the present invention. Heteroconjugate antibodies are composed of two covalently joined antibodies. Such antibodies have, for example, been proposed to target immune system cells to unwanted cells (see U.S. Pat. No. 4,676,980), and for treatment of HIV infection (see WO 91/00360; WO 92/200373; EP 03089). It is contemplated that the antibodies can be prepared in vitro using known methods in synthetic protein chemistry, including those involving crosslinking agents. For example, immunotoxins can be constructed using a disulfide exchange reaction or by forming a thioether bond. Examples of suitable reagents for this purpose include iminothiolate and methyl-4-mercaptobutyrimidate and those disclosed, for example, in U.S. Pat. No. 4,676,980.

It can be desirable to modify the antibody of the invention with respect to effector function, so as to enhance, e.g., the effectiveness of the antibody in treating SARS. For example, cysteine residue(s) can be introduced into the Fc region, thereby allowing interchain disulfide bond formation in this region. The homodimeric antibody thus generated can have improved internalization capability and/or increased complement-mediated cell killing and antibody-dependent cellular cytotoxicity (ADCC). (See Caron et al., J. Exp Med., 176: 1191-1195 (1992) and Shopes, J. Immunol., 148: 2918-2922 (1992)). Alternatively, an antibody can be engineered that has dual Fc regions and can thereby have enhanced complement lysis and ADCC capabilities. (See Stevenson et al., Anti-Cancer Drug Design, 3: 219-230 (1989)).

The invention also pertains to immunoconjugates comprising an antibody conjugated to a cytotoxic agent such as a toxin (e.g., an enzymatically active toxin of bacterial, fungal, plant, or animal origin, or fragments thereof), or a radioactive isotope (i.e., a radioconjugate).

Enzymatically active toxins and fragments thereof that can be used include diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes. A variety of radionuclides are available for the production of radioconjugated antibodies. Examples include $^{212}Bi$, $^{131}I$, $^{133}In$, $^{90}Y$, and $^{186}Re$.

Conjugates of the antibody and cytotoxic agent are made using a variety of bifunctional protein-coupling agents such as N-succinimidyl-3-(2-pyridyldithiol) propionate (SPDP), iminothiolane (IT), bifunctional derivatives of imidoesters (such as dimethyl adipimidate HCL), active esters (such as disuccinimidyl suberate), aldehydes (such as glutareldehyde), bis-azido compounds (such as bis (p-azidobenzoyl) hexanediamine), bis-diazonium derivatives (such as bis-(p-diazoniumbenzoyl)-ethylenediamine), diisocyanates (such as tolyene 2,6-diisocyanate), and bis-active fluorine compounds (such as 1,5-difluoro-2,4-dinitrobenzene). For example, a ricin immunotoxin can be prepared as described in Vitetta et al., Science 238: 1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. (See WO94/11026).

Those of ordinary skill in the art will recognize that a large variety of possible-moieties can be coupled to the resultant antibodies or to other molecules of the invention. (See, for example, "Conjugate Vaccines", Contributions to Microbiology and Immunology, J. M. Cruse and R. E. Lewis, Jr (eds), Carger Press, New York, (1989), the entire contents of which are incorporated herein by reference).

Coupling may be accomplished by any chemical reaction that will bind the two molecules so long as the antibody and the other moiety retain their respective activities. This linkage can include many chemical mechanisms, for instance covalent binding, affinity binding, intercalation, coordinate binding and complexation. The preferred binding is, however, covalent binding. Covalent binding can be achieved either by direct condensation of existing side chains or by the incorporation of external bridging molecules. Many bivalent or polyvalent linking agents are useful in coupling protein molecules, such as the antibodies of the present invention, to other molecules. For example, representative coupling agents can include organic compounds such as thioesters, carbodiimides, succinimide esters, diisocyanates, glutaraldehyde, diazobenzenes and hexamethylene diamines. This listing is not intended to be exhaustive of the various classes of coupling agents known in the art but, rather, is exemplary of the more common coupling agents. (See Killen and Lindstrom, Jour. Immun. 133:1335-2549 (1984); Jansen et al., Immunological Reviews 62:185-216 (1982); and Vitetta et al., Science 238: 1098 (1987)). Preferred linkers are described in the literature. (See, for example, Ramakrishnan, S. et al., Cancer Res. 44:201-208 (1984) describing use of MBS (M-maleimidobenzoyl-N-hydroxysuccinimide ester). See also, U.S. Pat. No. 5,030,719, describing use of halogenated acetyl hydrazide derivative coupled to an antibody by way of an oligopeptide linker. Particularly preferred linkers include: (i) EDC (1-ethyl-3-(3-dimethylamino-propyl) carbodiimide hydrochloride; (ii) SMPT (4-succinimidyloxycarbonyl-alpha-methyl-alpha-(2-pridyl-dithio)-toluene (Pierce Chem. Co., Cat. (21558G); (iii) SPDP (succinimidyl-6 [3-(2-pyridyldithio) propionamido]hexanoate (Pierce Chem. Co., Cat #21651G); (iv) Sulfo-LC-SPDP (sulfosuccinimidyl 6 [3-(2-pyridyldithio)-propianamide] hexanoate (Pierce Chem. Co. Cat. #2165-G); and (v) sulfo-NHS(N-hydroxysulfo-succinimide: Pierce Chem. Co., Cat. #24510) conjugated to EDC.

The linkers described above contain components that have different attributes, thus leading to conjugates with differing physio-chemical properties. For example, sulfo-NHS esters of alkyl carboxylates are more stable than sulfo-NHS esters of aromatic carboxylates. NHS-ester containing linkers are less soluble than sulfo-NHS esters. Further, the linker SMPT contains a sterically hindered disulfide bond, and can form conjugates with increased stability. Disulfide linkages, are in general, less stable than other linkages because the disulfide linkage is cleaved in vitro, resulting in less conjugate available. Sulfo-NHS, in particular, can enhance the stability of carbodimide couplings. Carbodimide couplings (such as EDC) when used in conjunction with sulfo-NHS, forms esters that are more resistant to hydrolysis than the carbodimide coupling reaction alone.

The antibodies disclosed herein can also be formulated as immunoliposomes. Liposomes containing the antibody are prepared by methods known in the art, such as described in Epstein et al., Proc. Natl. Acad. Sci. USA, 82: 3688 (1985); Hwang et al., Proc. Natl. Acad. Sci. USA, 77: 4030 (1980); and U.S. Pat. Nos. 4,485,045 and 4,544,545. Liposomes with enhanced circulation time are disclosed in U.S. Pat. No. 5,013,556.

Particularly useful liposomes can be generated by the reverse-phase evaporation method with a lipid composition comprising phosphatidylcholine, cholesterol, and PEG-derivatized phosphatidylethanolamine (PEG-PE). Liposomes are extruded through filters of defined pore size to yield liposomes with the desired diameter. Fab' fragments of the antibody of the present invention can be conjugated to the liposomes as described in Martin et al., J. Biol. Chem., 257: 286-288 (1982) via a disulfide-interchange reaction.

Use of Antibodies Against SARS-CoV

Methods for the screening of antibodies that possess the desired specificity include, but are not limited to, enzyme linked immunosorbent assay (ELISA) and other immunologically mediated techniques known within the art.

Antibodies directed against a SARS-CoV protein (or a fragment thereof) may be used in methods known within the art relating to the localization and/or quantitation of a SARS-CoV protein (e.g., for use in measuring levels of the SARS-CoV protein within appropriate physiological samples, for use in diagnostic methods, for use in imaging the protein, and the like). In a given embodiment, antibodies specific to a SARS-CoV protein, or derivative, fragment, analog or homolog thereof, that contain the antibody derived antigen binding domain, are utilized as pharmacologically active compounds (referred to hereinafter as "Therapeutics").

An antibody specific for a SARS-CoV protein of the invention can be used to isolate a SARS-CoV polypeptide by standard techniques, such as immunoaffinity, chromatography or immunoprecipitation. Antibodies directed against a SARS-CoV protein (or a fragment thereof) can be used diagnostically to monitor protein levels in tissue as part of a clinical testing procedure, e.g., to, for example, determine the efficacy of a given treatment regimen. Detection can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}$I, $^{131}$I, $^{35}$S or $^{3}$H.

Antibodies of the invention, including polyclonal, monoclonal, humanized and fully human antibodies, may used as therapeutic agents. Such agents will generally be employed to treat or prevent a coronavirus-related disease or pathology (e.g., SARS) in a subject. An antibody preparation, preferably one having high specificity and high affinity for its target antigen, is administered to the subject and will generally have an effect due to its binding with the target. Administration of the antibody may abrogate or inhibit or interfere with the binding of the target (e.g., ACE2) with an endogenous ligand (e.g., S1 region of SARS-CoV spike protein) to which it naturally binds. In this case, the antibody binds to the target and masks a binding site of the naturally occurring ligand, thereby neutralizing SARS-CoV by inhibiting binding of S1 to ACE2.

A therapeutically effective amount of an antibody of the invention relates generally to the amount needed to achieve a therapeutic objective. As noted above, this may be a binding interaction between the antibody and its target antigen that, in certain cases, interferes with the functioning of the target. The amount required to be administered will furthermore depend on the binding affinity of the antibody for its specific antigen, and will also depend on the rate at which an administered antibody is depleted from the free volume other subject to which it is administered. Common ranges for therapeutically effective dosing of an antibody or antibody fragment of the invention may be, by way of nonlimiting example, from about 0.1 mg/kg body weight to about 50 mg/kg body weight. Common dosing frequencies may range, for example, from twice daily to once a week.

Antibodies specifically binding a SARS-CoV protein or a fragment thereof of the invention, as well as other molecules identified by the screening assays disclosed herein, can be administered for the treatment of SARS-CoV-related disorders in the form of pharmaceutical compositions. Principles and considerations involved in preparing such compositions, as well as guidance in the choice of components are provided, for example, in Remington: The Science And Practice Of Pharmacy 19th ed. (Alfonso R. Gennaro, et al., editors) Mack Pub. Co., Easton, Pa., 1995; Drug Absorption Enhancement: Concepts, Possibilities, Limitations, And Trends, Harwood Academic Publishers, Langhorne, Pa., 1994; and Peptide And Protein Drug Delivery (Advances In Parenteral Sciences, Vol. 4), 1991, M. Dekker, New York.

Where antibody fragments are used, the smallest inhibitory fragment that specifically binds to the binding domain of the target protein is preferred. For example, based upon the variable-region sequences of an antibody, peptide molecules can be designed that retain the ability to bind the target protein sequence. Such peptides can be synthesized chemically and/ or produced by recombinant DNA technology. (See, e.g., Marasco et al., Proc. Natl. Acad. Sci. USA, 90: 7889-7893 (1993)). The formulation can also contain more than one active compound as necessary for the particular indication being treated, preferably those with complementary activities that do not adversely affect each other. Alternatively, or in addition, the composition can comprise an agent that enhances its function, such as, for example, a cytotoxic agent, cytokine, chemotherapeutic agent, or growth-inhibitory agent. Such molecules are suitably present in combination in amounts that are effective for the purpose intended.

The active ingredients can also be entrapped in microcapsules prepared, for example, by coacervation techniques or by interfacial polymerization, for example, hydroxymethylcellulose or gelatin-microcapsules and poly-(methylmethacrylate) microcapsules, respectively, in colloidal drug delivery systems (for example, liposomes, albumin microspheres, microemulsions, nano-particles, and nanocapsules) or in macroemulsions.

The formulations to be used for in vivo administration must be sterile. This is readily accomplished by filtration through sterile filtration membranes.

Sustained-release preparations can be prepared. Suitable examples of sustained-release preparations include semipermeable matrices of solid hydrophobic polymers containing the antibody, which matrices are in the form of shaped articles, e.g., films, or microcapsules. Examples of sustained-release matrices include polyesters, hydrogels (for example, poly(2-hydroxyethyl-methacrylate), or poly(vinylalcohol)), polylactides (U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(−)-3-hydroxybutyric acid. While polymers such as ethylene-vinyl acetate and lactic acid-glycolic acid enable release of molecules for over 100 days, certain hydrogels release proteins for shorter time periods.

An antibody according to the invention can be used as an agent for detecting the presence of SARS-CoV (or a protein or a protein fragment thereof) in a sample. Preferably, the antibody contains a detectable label. Antibodies can be polyclonal, or more preferably, monoclonal. An intact antibody, or a fragment thereof (e.g., $F_{ab}$, scFv, or $F_{(ab)2}$) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. Included within the usage of the term "biological sample", therefore, is blood and a fraction or component of blood including blood serum, blood plasma, or lymph. That is, the detection method of the invention can be used to detect an analyte mRNA, protein, or genomic DNA in a biological sample in vitro as well as in vivo. For example, in vitro techniques for detection of an analyte mRNA include Northern hybridizations and in situ hybridizations. In vitro techniques for detection of an analyte protein include enzyme linked immunosorbent assays (ELISAs), Western blots, immunoprecipitations, and immunofluorescence. In vitro techniques for detection of an analyte genomic DNA include Southern hybridizations. Procedures for conducting immunoassays are described, for example in "ELISA: Theory and Practice: Methods in Molecular Biology", Vol. 42, J. R. Crowther (Ed.) Human Press, Totowa, N.J., 1995; "Immunoassay", E. Diamandis and T. Christopoulus, Academic Press, Inc., San Diego, Calif., 1996; and "Practice and Theory of Enzyme Immunoassays", P. Tijssen, Elsevier Science Publishers, Amsterdam, 1985. Furthermore, in vivo techniques for detection of an analyte protein include introducing into a subject a labeled anti-analyte protein antibody. For example, the antibody can be labeled with a radioactive marker whose presence and location in a subject can be detected by standard imaging techniques.

Pharmaceutical Compositions

The antibodies or agents of the invention (also referred to herein as "active compounds"), and derivatives, fragments, analogs and homologs thereof, can be incorporated into pharmaceutical compositions suitable for administration. Such compositions typically comprise the antibody or agent and a pharmaceutically acceptable carrier. As used herein, the term "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (i.e., topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR® EL; BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active-compound for the treatment of individuals.

The pharmaceutical compositions can be included in a container, pack, or dispenser together with instructions for administration.

Screening Methods

The invention provides methods (also referred to herein as "screening assays") for identifying modulators, i.e., candidate or test compounds or agents (e.g., peptides, peptidomimetics, small molecules or other drugs) that modulate or otherwise interfere with the binding of SARS-CoV to the SARS-CoV receptor, ACE2. Also provided are methods of identifying compounds useful to treat SARS infection. The invention also encompasses compounds identified using the screening assays described herein.

For example, the invention provides assays for screening candidate or test compounds which modulate the interaction between SARS-CoV and its receptor, ACE2. The test compounds of the invention can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds. (See, e.g., Lam, 1997. Anticancer Drug Design 12: 145).

A "small molecule" as used herein, is meant to refer to a composition that has a molecular weight of less than about 5 kD and most preferably less than about 4 kD. Small molecules can be, e.g., nucleic acids, peptides, polypeptides, peptidomimetics, carbohydrates, lipids or other organic or inorganic molecules. Libraries of chemical and/or biological mixtures, such as fungal, bacterial, or algal extracts, are known in the art and can be screened with any of the assays of the invention.

Examples of methods for the synthesis of molecular libraries can be found in the art, for example in: DeWitt, et al., 1993. Proc. Natl. Acad. Sci. U.S.A. 90: 6909; Erb, et al., 1994. Proc. Natl. Acad. Sci. U.S.A. 91: 11422; Zuckermann, et al., 1994. J. Med. Chem. 37: 2678; Cho, et al., 1993. Science 261: 1303; Carrell, et al., 1994. Angew. Chem. Int. Ed. Engl. 33: 2059; Carell, et al., 1994. Angew. Chem. Int. Ed. Engl. 33: 2061; and Gallop, et al., 1994. J. Med. Chem. 37:1233.

Libraries of compounds may be presented in solution (see e.g., Houghten, 1992. Biotechniques 13: 412-421), or on beads (see Lam, 1991. Nature 354: 82-84), on chips (see Fodor, 1993. Nature 364: 555-556), bacteria (see U.S. Pat. No. 5,223,409), spores (see U.S. Pat. No. 5,233,409), plasmids (see Cull, et al., 1992. Proc. Natl. Acad. Sci. USA 89: 1865-1869) or on phage (see Scott and Smith, 1990. Science 249: 386-390; Devlin, 1990. Science 249: 404-406; Cwirla, et al., 1990. Proc. Natl. Acad. Sci. U.S.A. 87: 6378-6382; Felici, 1991. J. Mol. Biol. 222: 301-310; and U.S. Pat. No. 5,233, 409.).

In one embodiment, a candidate compound is introduced to an antibody-antigen complex and determining whether the candidate compound disrupts the antibody-antigen complex, wherein a disruption of this complex indicates that the candidate compound modulates the interaction between SARS-CoV and ACE2. For example, the antibody may be monoclonal antibody 80R and the antigen may be located on the S1 region of the S protein of SARS-CoV.

In another embodiment, at least one SARS-CoV protein is provided, which is exposed to at least one neutralizing monoclonal antibody. Formation of an antibody-antigen complex is detected, and one or more candidate compounds are introduced to the complex. If the antibody-antigen complex is disrupted following introduction of the one or more candidate compounds, the candidate compounds is useful to treat a SARS-CoV-related disease or disorder, e.g. SARS. For example, the at least one SARS-CoV protein may be provided as a SARS-CoV molecule, or, in another embodiment, the at least one SARS-CoV protein may be provided in a cell infected with SARS-CoV. The cell, for example, can of mammalian origin or a yeast cell.

Determining the ability of the test compound to interfere with or disrupt the antibody-antigen complex can be accomplished, for example, by coupling the test compound with a radioisotope or enzymatic label such that binding of the test compound to the antigen or biologically-active portion thereof can be determined by detecting the labeled compound in a complex. For example, test compounds can be labeled with $^{125}I$, $^{35}S$, $^{14}C$, or $^{3}H$, either directly or indirectly, and the radioisotope detected by direct counting of radioemission or by scintillation counting. Alternatively, test compounds can be enzymatically-labeled with, for example, horseradish peroxidase, alkaline phosphatase, or luciferase, and the enzymatic label detected by determination of conversion of an appropriate substrate to product.

In one embodiment, the assay comprises contacting an antibody-antigen complex with a test compound, and determining the ability of the test compound to interact with the antigen or otherwise disrupt the existing antibody-antigen complex. In this embodiment, determining the ability of the test compound to interact with the antigen and/or disrupt the antibody-antigen complex comprises determining the ability of the test compound to preferentially bind to the antigen or a biologically-active portion thereof, as compared to the antibody.

In another embodiment, the assay comprises contacting an antibody-antigen complex with a test compound and determining the ability of the test compound to modulate the antibody-antigen complex. Determining the ability of the test compound to modulate the antibody-antigen complex can be accomplished, for example, by determining the ability of the antigen to bind to or interact with the antibody, in the presence of the test compound.

Those skilled in the art will recognize that, in any of the screening methods disclosed herein, the antibody may be a SARS-CoV neutralizing antibody, such as monoclonal antibody 80R. Additionally, the antigen may be a SARS-CoV protein, or a portion thereof (e.g., the S1 region of the SARS-CoV S protein). In any of the assays described herein, the ability of a candidate compound to interfere with the binding between the 80R monoclonal antibody and the S1 region of the SARS-CoV spike protein indicates that the candidate compound will be able to interfere with or modulate the binding of SARS-CoV to the ACE2 receptor. Moreover, because the binding of the S1 protein to ACE2 is responsible for SARS-CoV entry into cells (see Li et al., Nature 426:450-54 (2003), incorporated herein by reference), such candidate compounds will also be useful in the treatment of a SARS-CoV-related disease or disorder, e.g. SARS.

The screening methods disclosed herein may be performed as a cell-based assay or as a cell-free assay. The cell-free assays of the invention are amenable to use of both the soluble form or the membrane-bound form of SARS-CoV proteins and fragments thereof. In the case of cell-free assays comprising the membrane-bound forms of the SARS-CoV proteins, it may be desirable to utilize a solubilizing agent such that the membrane-bound form of the proteins are maintained in solution. Examples of such solubilizing agents include non-ionic detergents such as n-octylglucoside, n-dodecylglucoside, n-dodecylmaltoside, octanoyl-N-methylglucamide, decanoyl-N-methylglucamide, TRITON® X-100 (t-octylphenoxypolyethoxyethanol) TRITON® X-114 (polyethylene glycol tert-octylphenyl ether), THESIT® (polyethylene glycol dodecyl ether), Isotridecypoly(ethylene glycol ether)$_n$, N-dodecyl-N,N-dimethyl-3-ammonio-1-propane sulfonate, 3-(3-cholamidopropyl) dimethylamminiol-1-propane sulfonate (CHAPS), or 3-(3-cholamidopropyl)dimethylamminiol-2-hydroxy-1-propane sulfonate (CHAPSO).

In more than one embodiment, it may be desirable to immobilize either the antibody or the antigen to facilitate separation of complexed from uncomplexed forms of one or both following introduction of the candidate compound, as well as to accommodate automation of the assay. Observation of the antibody-antigen complex in the presence and absence of a candidate compound, can be accomplished in any vessel suitable for containing the reactants. Examples of such vessels include microtiter plates, test tubes, and micro-centrifuge tubes. In one embodiment, a fusion protein can be provided that adds a domain that allows one or both of the proteins to be bound to a matrix. For example, GST-antibody fusion proteins or GST-antigen fusion proteins can be adsorbed onto glutathione sepharose beads (Sigma Chemical, St. Louis, Mo.) or glutathione derivatized microtiter plates, that are then combined with the test compound, and the mixture is incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly. Alternatively, the complexes can be dissociated from the matrix, and the level of antibody-antigen complex formation can be determined using standard techniques.

Other techniques for immobilizing proteins on matrices can also be used in the screening assays of the invention. For example, either the antibody (e.g. 80R) or the antigen (e.g. the S1 protein of SARS-CoV) can be immobilized utilizing conjugation of biotin and streptavidin. Biotinylated antibody or antigen molecules can be prepared from biotin-NHS (N-hydroxy-succinimide) using techniques well-known within the art (e.g., biotinylation kit, Pierce Chemicals, Rockford, Ill.), and immobilized in the wells of streptavidin-coated 96 well plates (Pierce Chemical). Alternatively, other antibodies reactive with the antibody or antigen of interest, but which do not interfere with the formation of the antibody-antigen complex of interest, can be derivatized to the wells of the plate, and unbound antibody or antigen trapped in the wells by antibody conjugation. Methods for detecting such complexes, in addition to those described above for the GST-immobilized complexes, include immunodetection of complexes using such other antibodies reactive with the antibody or antigen.

The invention further pertains to novel agents identified by any of the aforementioned screening assays and uses thereof for treatments as described herein.

Diagnostic Assays

Antibodies of the present invention can be detected by appropriate assays, e.g., conventional types of immunoassays. For example, a sandwich assay can be performed in which a SARS-CoV protein (e.g., S1, S2, and/or M) or fragment thereof is affixed to a solid phase. Incubation is maintained for a sufficient period of time to allow the antibody in the sample to bind to the immobilized polypeptide on the solid phase. After this first incubation, the solid phase is separated from the sample. The solid phase is washed to remove unbound materials and interfering substances such as non-specific proteins which may also be present in the sample. The solid phase containing the antibody of interest (e.g. monoclonal antibody 80R) bound to the immobilized polypeptide is subsequently incubated with a second, labeled antibody or antibody bound to a coupling agent such as biotin or avidin. This second antibody may be another anti-SARS-CoV antibody or another antibody. Labels for antibodies are well-known in the art and include radionuclides, enzymes (e.g. maleate dehydrogenase, horseradish peroxidase, glucose oxidase, catalase), fluors (fluorescein isothiocyanate, rhodamine, phycocyanin, fluorescarmine), biotin, and the like. The labeled antibodies are incubated with the solid and the label bound to the solid phase is measured. These and other immunoassays can be easily performed by those of ordinary skill in the art.

An exemplary method for detecting the presence or absence of a coronavirus (e.g. SARS-CoV) in a biological sample involves obtaining a biological sample from a test subject and contacting the biological sample with a labeled monoclonal or scFv antibody according to the invention such that the presence of the coronavirus is detected in the biological sample.

As used herein, the term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with another reagent that is directly labeled. Examples of indirect labeling include detection of a primary antibody using a fluorescently-labeled secondary antibody and end-labeling of a DNA probe with biotin such that it can be detected with fluorescently-labeled streptavidin. The term "biological sample" is intended to include tissues, cells and biological fluids isolated from a subject, as well as tissues, cells and fluids present within a subject. That is, the detection method of the invention can be used to detect SARS-CoV in a biological sample in vitro as well as in vivo. For example, in vitro techniques for detection of SARS-CoV include enzyme linked immunosorbent assays (ELISAs), Western blots, immunoprecipitations, and immunofluorescence. Furthermore, in vivo techniques for detection of SARS-CoV include introducing into a subject a labeled anti-SARS-CoV antibody. For example, the antibody can be labeled with a radioactive marker whose presence and location in a subject can be detected by standard imaging techniques.

In one embodiment, the biological sample contains protein molecules from the test subject. One preferred biological sample is a peripheral blood leukocyte sample isolated by conventional means from a subject.

The invention also encompasses kits for detecting the presence of SARS-CoV in a biological sample. For example, the kit can comprise: a labeled compound or agent capable of detecting SARS-CoV (e.g., an anti-SARS-CoV scFv or monoclonal antibody) in a biological sample; means for determining the amount of SARS-CoV in the sample; and means for comparing the amount of SARS-CoV in the sample with a standard. The compound or agent can be packaged in a suitable container. The kit can further comprise instructions for using the kit to detect SARS-CoV in a sample.

Passive Immunization

Passive immunization has proven to be an effective and safe strategy for the prevention and treatment of viral diseases. (See Keller et al., Clin. Microbiol. Rev. 13:602-14 (2000); Casadevall, Nat. Biotechnol. 20:114 (2002); Shibata et al., Nat. Med. 5:204-10 (1999); and Igarashi et al., Nat. Med. 5:211-16 (1999), each of which are incorporated herein by reference)). Passive immunization using neutralizing human monoclonal antibodies could provide an immediate treatment strategy for emergency prophylaxis and treatment of SARS while the alternative and more time-consuming development of vaccines and new drugs in underway. Investigations with other coronaviruses have indicated that passively administered neutralizing antibodies can protect against disease (see Kolb et al., J. Virol. 75:2803 (2001)), and that it is possible to elicit neutralizing antibodies against both linear (Godet et al., J. Virol. 68:8008 (1994); Talbot et al., J. Virol. 62:3032 (1988); and Yu et al., Virology 271:182 (2000)) and conformational (see Yu et al., Virology 271:182 (2000)) epitopes of coronavirus spike proteins, and/or membrane proteins. (See Kida et al., Arch. Virol. 75:2803 (2001) and Vennema et al., Virology 181:327 (1991)). In some cases, these neutralizing antibodies have also been shown to confer protection. (See Talbot et al., 1988; Koo et al., Proc. Natl. Acad. Sci. USA 96(14):7774-79 (1999); and Yu et al., 2000)).

Moreover, it has been reported that high titers of protecting IgG antibody to SARS-CoV are present in convalescent patients. Likewise, SARS patients show clinical improvement if they are given serum from previously infected patients. (See Pearson et al., Nature 424:121-26 (2003); Li et al., N. Engl. J. Med. 349:508-9 (2003)). These observations suggest that passive immunization with human monoclonal antibodies could be developed for the treatment of SARS. (See Holmes, J. Clin. Invest. 111: 1605-9 (2003)).

As shown in Example 9, infra, passive transfer of 80R IgG1 can completely protect mice from SARS-CoV replication in lung tissue, at doses that are therapeutically achievable in humans. The potent virus-neutralizing activity of MAb 80R is likely due to the overlap between the 80R epitope and the ACE2 receptor-binding domain of S protein. Because variations in the genome of SARS-like-CoVs will likely occur because of the high mutation rate of RNA viruses, a genotyping monitor will be necessary for an effective use of a prophylaxis strategy based on neutralizing antibody responses.

Based on experience with other coronaviruses, those skilled in the art will recognize that a subunit vaccine can be designed to elicit neutralizing antibodies against SARS. Thus, the development of neutralizing human monoclonal antibodies and subunit vaccine candidates that are based on the epitopes on SARS-CoV spike and membrane proteins will play an important role in such therapeutic methods.

Subunit vaccines potentially offer significant advantages over conventional immunogens. They avoid the safety hazards inherent in production, distribution, and delivery of conventional killed or attenuated whole-pathogen vaccines. Furthermore, they can be rationally designed to include only confirmed protective epitopes, thereby avoiding suppressive T epitopes (see Steward et al., J. Virol. 69:7668 (1995)) or immunodominant B epitopes that subvert the immune system by inducing futile, non-protective responses (e.g. "decoy" epitopes). (See Garrity et al., J. Immunol. 159:279 (1997)).

Importantly for SARS, a subunit vaccine may circumvent the problem of antibody-dependent disease enhancement, which has been shown to occur in some other coronaviruses (see De Groot, Vaccine 21:4095-104 (2003)) and, which may be epitope dependent (see Vennema et al., Virology 181:327 (1991) and Corapi et al., J. Virol. 69:2858 (1995)). Subunit vaccines also offer potential solutions to problems including pathogen variation and hypermutability that often plague vaccine development efforts. Only epitopes from invariant, conserved regions of a pathogen's antigenic structure need be included in the subunit vaccine, thereby ensuring long-term protection for individuals and populations. Alternatively, a cocktail of peptides representing multiple variants of an antigen could be assembled, in order to mimic a range of variants of a highly mutable epitope. (See Taboga et al., J. Virol.

71:2606 (1997)). Finally, subunit vaccines are cheaper to manufacture and more stable than many other vaccine formulations.

Moreover, those skilled in the art will recognize that good correlation exists between the antibody neutralizing activity in vitro and the protection in vivo for many different viruses, challenge routes, and animal models. (See Burton, Natl. Rev. Immunol. 2:706-13 (2002); Parren et al., Adv. Immunol. 77:195-262 (2001)). The in vitro and in vivo data presented herein suggest that the 80R human monoclonal antibody can be further developed and tested in in vivo animal studies to determine its clinical utility as a potent viral entry inhibitor for emergency prophylaxis and treatment of SARS. Thus, the 180 amino acid region of the SAR-CoV S protein encompassing the 80R epitope is an essential core region of the S protein for subunit vaccines aimed at eliciting potent neutralizing antibody responses.

Antigen-Ig Chimeras in Vaccination

It has been over a decade since the first antibodies were used as scaffolds for the efficient presentation of antigenic determinants to the immune systems. (See Zanetti, Nature 355:476-77 (1992); Zaghouani et al., Proc. Natl. Acad. Sci. USA 92:631-35 (1995)). When a peptide is included as an integral part of an IgG molecule (e.g., the 80R IgG1 monoclonal antibody described herein), the antigenicity and immunogenicity of the peptide epitopes are greatly enhanced as compared to the free peptide. Such enhancement is possibly due to the antigen-IgG chimeras longer half-life, better presentation and constrained conformation, which mimic their native structures.

Moreover, an added advantage of using an antigen-Ig chimera is that either the variable or the Fc region of the antigen-Ig chimera can be used for targeting professional antigen-presenting cells (APCs). To date, recombinant Igs have been generated in which the complementarity-determining regions (CDRs) of the heavy chain variable gene ($V_H$) are replaced with various antigenic peptides recognized by B or T cells. Such antigen-Ig chimeras have been used to induce both humoral and cellular immune responses. (See Bona et al., Immunol. Today 19:126-33 (1998)).

Chimeras with specific epitopes engrafted into the CDR3 loop have been used to induce humoral responses to either HIV-1 gp120 V3-loop or the first extracellular domain (D1) of human CD4 receptor. (See Lanza et al., Proc. Natl. Acad. Sci. USA 90:11683-87 (1993); Zaghouani et al., Proc. Natl. Acad. Sci. USA 92:631-35 (1995)). The immune sera were able to prevent infection of CD4 SupT1 cells by HIV-1MN (anti-gp120 V3C) or inhibit syncytia formation (anti-CD4-D1). The CDR2 and CDR3 can be replaced with peptide epitopes simultaneously, and the length of peptide inserted can be up to 19 amino acids long.

Alternatively, one group has developed a "troybody" strategy in which peptide antigens are presented in the loops of the Ig constant (C) region and the variable region of the chimera can be used to target IgD on the surface of B-cells or MHC class II molecules on professional APCs including B-cells, dendritic cells (DC) and macrophages. (See Lunde et al., Biochem. Soc. Trans. 30:500-6 (2002)).

An antigen-Ig chimera can also be made by directly fusing the antigen with the Fc portion of an IgG molecule. You et al., Cancer Res. 61:3704-11 (2001) were able to obtain all arms of specific immune response, including very high levels of antibodies to hepatitis B virus core antigen using this method.

DNA Vaccination

DNA vaccines are stable, can provide the antigen an opportunity to be naturally processed, and can induce a longer-lasting response. Although a very attractive immunization strategy, DNA vaccines often have very limited potency to induce immune responses. Poor uptake of injected DNA by professional APCs, such as dendritic cells (DCs), may be the main cause of such limitation. Combined with the antigen-Ig chimera vaccines, a promising new DNA vaccine strategy based on the enhancement of APC antigen presentation has been reported (see Casares, et al., Viral Immunol. 10:129-36 (1997); Gerloni et al., Nat. Biotech. 15:876-81 (1997); Gerloni et al., DNA Cell Biol. 16:611-25 (1997); You et al., Cancer Res. 61:3704-11 (2001)), which takes advantage of the presence of Fc receptors (FcγRs) on the surface of DCs.

It is possible to generate a DNA vaccine encoding an antigen (Ag)-Ig chimera. Upon immunization, Ag-Ig fusion proteins will be expressed and secreted by the cells taking up the DNA molecules. The secreted Ag-Ig fusion proteins, while inducing B-cell responses, can be captured and internalized by interaction of the Fc fragment with FcγRs on DC surface, which will promote efficient antigen presentation and greatly enhance antigen-specific immune responses. Applying the same principle, DNA encoding antigen-Ig chimeras carrying a functional anti-MHC II specific scFv region gene can also target the immunogens to all three types of APCs. The immune responses could be further boosted with use of the same protein antigens generated in vitro (i.e., "prime and boost"), if necessary. Using this strategy, specific cellular and humoral immune responses against infection of influenza virus were accomplished through intramuscular (i.m.) injection of a DNA vaccine. (See Casares et al., Viral. Immunol. 10: 129-36 (1997)).

Vaccine Compositions

Therapeutic or prophylactic compositions are provided herein, which generally comprise mixtures of one or more monoclonal antibodies or ScFvs and combinations thereof. The prophylactic vaccines can be used to prevent SARS-CoV infection and the therapeutic vaccines can be used to treat individuals following SARS-CoV infection. Prophylactic uses include the provision of increased antibody titer to SARS-CoV in a vaccination subject. In this manner, subjects at high risk of contracting SARS can be provided with passive immunity to SARS-CoV.

These vaccine compositions can be administered in conjunction with ancillary immunoregulatory agents. For example, cytokines, lymphokines, and chemokines, including, but not limited to, IL-2, modified IL-2 (Cys125→Ser125), GM-CSF, IL-12, γ-interferon, IP-10, MIP1β, and RANTES.

Evaluation of Antigenic Protein Fragments (APFs) for Vaccine Potential

A vaccine candidate targeting humoral immunity must fulfill at least three criteria to be successful: it must provoke a strong antibody response ("immunogenicity"); a significant fraction of the antibodies it provokes must cross-react with the pathogen ("immunogenic fitness"); and the antibodies it provokes must be protective. While immunogenicity can often be enhanced using adjuvants or carriers, immunogenic fitness and the ability to induce protection (as evidenced by neutralization) are intrinsic properties of an antigen which will ultimately determine the success of that antigen as a vaccine component.

Evaluation of Immunogenic Fitness

"Immunogenic fitness" is defined as the fraction of antibodies induced by an antigen that cross-react with the pathogen. (See Matthews et al., J. Immunol. 169:837 (2002)). It is distinct from immunogenicity, which is gauged by the titer of all of the antibodies induced by an antigen, including those antibodies that do not cross-react with the pathogen. Inadequate immunogenic fitness has probably contributed to the disappointing track record of peptide vaccines to date. Peptides that bind with high affinity to antibodies and provoke high antibody titers frequently lack adequate immunogenic fitness, and, therefore, they fail as potential vaccine components. Therefore, it is important to include immunogenic fitness as one of the criteria for selecting SARS vaccine candidates.

A common explanation for poor immunogenic fitness is the conformational flexibility of most short peptides. Specifically, a flexible peptide may bind well to antibodies from patients, and elicit substantial antibody titers in naïve subjects. However, if the peptide has a large repertoire of conformations, a preponderance of the antibodies it induces in naïve subjects may fail to cross-react with the corresponding native epitope on intact pathogen.

Like short peptides, some APFs may be highly flexible and, therefore may fail as vaccine components. The most immunogenically fit APFs are likely to consist of self-folding protein subdomains that are intrinsically constrained outside the context of the whole protein.

Because immunogenic fitness is primarily a property of the APF itself, and not of the responding immune system, immunogenic fitness can be evaluated in an animal model (e.g. in mice) even though ultimately the APF will have to perform in humans.

The immunogenic fitness achieved by APFs is evaluated by immunosorption of anti-APF sera with purified spike or membrane protein, in a procedure analogous to that described in Matthews et al., J. Immunol. 169:837 (2002). IgG is purified from sera collected from mice that have been immunized. Purified, biotinylated spike and membrane proteins (as appropriate, depending on the particular APF with which the mice were immunized) are mixed with the mouse IgG and incubated. Streptavidin-coated sepharose beads are then added in sufficient quantity to capture all of the biotinylated spike or membrane protein, along with any bound IgG. The streptavidin-coated beads are removed by centrifugation at 13,000 rpm in a microcentrifuge, leaving IgG that has been depleted of antibodies directed against the spike or membrane protein, respectively. Mock immunoabsorptions are performed in parallel in the same way, except that biotinylated BSA will be substituted for SARS protein as a mock absorbent.

To measure the immunogenic fitness of APFs, the spike- or membrane-absorbed antibodies and the mock-absorbed antibodies are titered side-by-side in ELISA against the immunizing APF. For APFs affinity selected from a phage display NPL, the antigen for these ELISAs will be purified APF-GST fusion proteins. For the potentially glycosylated APFs from the mammalian cell display NPL, the antigen for these ELISAs will be APF-Fc fusion proteins secreted by mammalian cells and purified with protein A. The percentage decrease in the anti-APF titer of spike- or membrane-absorbed antibodies compared with the mock-absorbed antibodies will provide a measure of the immunogenic fitness of the APF.

Methods of Treatment

The invention provides for both prophylactic and therapeutic methods of treating a subject at risk of (or susceptible to) a coronavirus-related disease or disorder. Such diseases or disorders include but are not limited to, e.g., SARS.

Prophylactic Methods

In one aspect, the invention provides methods for preventing a coronavirus-related disease or disorder in a subject by administering to the subject a monoclonal antibody or scFv antibody of the invention or an agent identified according to the methods of the invention. For example, scFv 80R and/or monoclonal antibody 80R may be administered in therapeutically effective amounts.

Subjects at risk for coronavirus-related diseases or disorders include patients who have come into contact with an infected person or who have been exposed to the coronavirus in some other way. Administration of a prophylactic agent can occur prior to the manifestation of symptoms characteristic of the coronavirus-related disease or disorder, such that a disease or disorder is prevented or, alternatively, delayed in its progression.

The appropriate agent can be determined based on screening assays described herein. Alternatively, or in addition, the agent to be administered is a scFv or monoclonal antibody that neutralizes SARS that has been identified according to the methods of the invention.

Therapeutic Methods

Another aspect of the invention pertains to methods of treating a coronavirus-related disease or disorder in a patient. In one embodiment, the method involves administering an agent (e.g., an agent identified by a screening assay described herein and/or an scFv antibody or monoclonal antibody identified according to the methods of the invention), or combination of agents that neutralize the coronavirus to a patient suffering from the disease or disorder.

The invention will be further described in the following examples, which do not limit the scope of the invention described in the claims.

EXAMPLES

Example 1

Expression and Purification of SARS-CoV S1 and Truncated S1

Plasmids encoding S1 domain of SARS-CoV S protein (residues 12-672), N-terminal of the S1 (residues 12-327) or C-terminal of the S1 (residues 264-672) fused with Fc region of human IgG1 (named S1-Ig, S1 (327)-Ig and S1 (264-672)-Ig, respectively) were transfected into 293T cells for transient expression. Plasmids encoding the S1 domain (residues 12-672) fused C-terminally with C9 (S1-C9) was also transfected into 293T for expression. The Ig-tagged proteins were purified by protein A Sepharose. Anti-C9 antibody 1D4 (obtained from the National Cell Culture Center) was conjugated with protein A Sepharose and was used for purification of S1-C9. The purity was detected by SDS-PAGE and the protein concentration was determined by a protein assay kit (Bio Rad, Hercules, Calif.).

Example 2

Selection of Phase Library and Screening of Phage Antibodies

Two human non-immune scFv libraries (having a total of $2.7 \times 10^{10}$ members) constructed from B-cells of 57 un-immunized donors were used for selection of scFvs against the purified S1-C9. $5 \times 10^{11}$ pfu of phage-scFvs prepared from each library were mixed and introduced for panning into Maxisorp immunotubes (Nunc, Naperville, Ill.) coated with 10 μg S1-C9. Non-specifically absorbed phages were removed by intensive washings. Specific bound phages were eluted with 100 mM triethylamine, neutralized, amplified and used for further selections as described by Harrison et al., Methods. Enzymol. 267:83-109 (1996).

Randomly picked single phage-scFv clones were screened for specific binding to S1-C9 by enzyme-linked immunosorbent assay (ELISA) after three rounds of panning. 96-well Maxisorp immunoplates were coated with 0.2 μg S1-C9 per well or control proteins HIV-1 gp120-C9 and BSA, blocked with PBS containing 4% nonfat milk. Phage-scFvs in PBS containing 2% nonfat milk were added. Specific bound phages were detected by adding HRP-conjugated mouse anti-M13 and the system was developed by adding TMB substrate. Absorbance at 450 nm was measured. Clones that bound to S1-C9 with $A_{450}$ values of >1.0 were scored as positive, whereas negative clones gave values of <0.2. For S1-C9 specific binding clones, the genes of variable regions of heavy (VH) and light (VL) chain were sequenced and their corresponding amino acid sequences were aligned. (See FIG. 1).

Example 3

Expression and Purification of ScFvs and Whole Human IgG1

The VH and VL gene fragments of eight S1-specific scFvs (6A, 8C, 12E, 26H, 27D, 80R, 91M, and 92N) were cloned into prokaryotic expressing vectors. Some of them (scFvs 6A, 80R, 91M and 92N) were cloned into pSyn1 vector (see Schier et al., Immunotechnology 1:73-81 (1995); Bai et al, J. Biol. Chem. 278:1433-42 (2003)), expressed in *E. Coli*. XL1-Blue (Stratagene, La Jolla, Calif.), and purified from the periplasmic fractions. The others (scFvs 8C, 12E, 26H, and 27D) were cloned into pET22b(+) vector (Novagen, Madison, Wis.), expressed in *E. coli* BL21(DE3) (Novagen) and purified from insoluble fraction of the inclusion bodies.

All scFvs contain a His-6 tag that allows purification by immobilized metal affinity chromatography (IMAC). The scFvs purified from the periplasmic extracts were dialyzed in PBS, and the scFvs purified from inclusion bodies were renatured by dialyzing in 0.4 M L-Arginine containing buffer followed by PBS. The S1-binding activity of purified soluble scFvs were confirmed by ELISA using S1-C9 and S1-Ig. The rabbit anti-His-6 polyclonal antibody (Santa Cruz, Santa Cruz, Calif.) and HRP-labeled anti-rabbit Ig (Pierce, Rockford, Ill.) were used to detect the bound scFvs in ELISA.

For production of whole human IgG1, the VH and VL gene fragments of the scFv were separately subcloned into human IgG1 kappa light chain expression vector TCAE5. (See Reff et al., Blood 83:435-45 (1994)). IgG1 was expressed in 293T cells by transient transfection and purified by protein A sepharose affinity chromatography.

Example 4

Micro-Neutralization Assay

To pre-serially diluted antibody samples in 96-well tissue culture plates, ~37 plaque forming units (pfu) of SARS-CoV (Urbani strain) was added, and the mixture was incubated at 37° C. for 1 hour. Subsequently, ~$2\times10^5$ Vero E6 cells were added to each antibody/virus mixture, and the plate was incubated further at 37° C./5% $CO_2$ for 3-4 days. To visualize the results, the plate was stained with crystal violet-formaldehyde stain (0.013% crystal violet, 2.5% Ethanol and 10% formaldehyde in 0.01M Phosphate buffered saline) for an hour at room temperature. The assay was performed in triplicate.

Example 5

Syncytia Inhibition Assay with Anti-S1 Antibodies 293T cells, (approximately 30% confluent in T75 flask), were transfected with plasmids encoding a codon-optimized form of full length of SARS-CoV S protein or receptor ACE2. One day after transfection, cells were trypsinized and washed once in medium. Those S protein expressing cells were premixed with 0, 25, 50 and 100 nM of anti-S1 scFvs or IgG1 for 10 minutes at room temperature. These cells were then mixed with cells expressing ACE2 at a 1:1 ratio and were plated on 24-well plates. Cells were cultured in the presence of antibodies. After 36 hours, syncytia were observed and representative photographs were taken. Representative results are shown in FIG. 3.

Example 6

Affinity Measurement by BIAcore

The binding kinetics and affinity of neutralizing antibody and receptor ACE2 to the purified S1-Ig were analyzed by surface plasmon resonance (BIAcore 3000, Sweden). The purified S1-Ig was covalently immobilized to a CM5 sensor chip via amine group using the amine coupling kit (BIAcore) in 10 mM sodium acetate buffer, at pH 4.5. Experiments were run at a flow rate of 10 μl/min in HBS-EP buffer (BIAcore). The surface was regenerated with 10 mM glycine-HCl at pH 2.0. Binding kinetic parameters were measured with antibodies or receptor at different molar concentrations, and evaluated with the BIA-evaluation software.

Example 7

Flow Cytometry Analysis of Inhibition of S1 Binding to Vero E6 Cells by Antibody 0, 5, 15 or 30 μg/ml of scFvs were mixed with 15 μg/ml S1-Ig in a 40 μl volume at 4° C. for 1 hour. Each mixture was added to Vero E6 cells ($2\times10^5$) and incubated at 4° C. for 1 hour. S1 (327)-Ig was used as S1-Ig control also incubated with Vero E6 cells. Cells were washed three times with PBS containing 0.5% BSA and 0.1% $NaN_3$. For detection of S1-Ig binding to Vero E6 cells, FITC-labeled goat anti-human IgG (Pierce) was used as secondary antibody and incubated with cells at 4° C. for 30 min. Cells were washed as above. Samples were analyzed using a Becton Dickinson FACScan with CellQuest software.

Example 8

Radio-Immunoprecipitation Assay of Inhibition of S1 Binding to Soluble ACE2 by Antibody 1.5 μg S1-Ig was mixed with different amounts (0.1, 0.5, 1.5, 4.5 μg) of scFvs and incubated at 4° C. for 1 hour. Soluble ACE2 was expressed in 293T cells and metabolically labeled for 24 hours with [$^{35}$S]-cysteine and -methionine (NEN Life Science, Boston, Mass.). The premixed S1-Ig and scFvs or goat anti-human ACE2 polyclonal antibody (R&D system, Minneapolis, Minn.) were added to 100 μl of metabolically labeled ACE2 and protein A Sepharose beads and incubated for 1 hours at 4° C. The beads were washed four times with PBS containing 0.25% $NP_{40}$ and 0.01% SDS. Bound proteins were eluted in reducing Lammlie-sample buffer at 100° C. for 5 mins. Proteins were separated by 8% SDS-PAGE and visualized by autoradiography on Kodak Biomax MR film.

Example 9

Evaluation of Human MAb 80R in Immunoprophylaxis of SARS in Mouse Studies

All mouse studies were approved by the NIH Animal Care and Use Committee and were carried out in an approved animal biosafety level 3 facility and personnel entering the facility wore powered air purifying respirators (3M HEPA AirMate, Saint Paul, Minn.).

Sixteen-week-old female BALB/c mice were housed four per cage (see Subbarao et al., J Virol 78:3572-77 (2004)). Mice were lightly anesthetized with isoflurane before receiving injections of antibodies. On day 0, three groups of mice (n=4 for each) were intraperitoneally injected with 3 different doses of 80R IgG1(500 μl of 500 μg/ml, 100 μg/ml and 20 μg/ml of 80R IgG1 in PBS). The control group (n=4) was injected with 500 μl of 500 μg/ml of a human IgG1 isotype control antibody in the same buffer as 80R IgG1. One day later, mice were challenged with $10^4$ 50% tissue culture infectious dose ($TCID_{50}$) of SARS-CoV (Urbani Strain) intranasally, and they were sacrificed 2 days later. The lungs were removed and homogenized in a 10% w/v suspension in Leibovitz 15 medium (Invitrogen, Carlsbad, Calif.) and virus titers were determined in Vero cell monolayers in 96-well plates.

80R IgG1 was given intraperitoneally to BALB/c mice 1 day before SARS-CoV ($10^4$ $TCID_{50}$) intranasal challenge and two days later, the virus titer of lung tissue was determined. As shown in Table 3, at the highest 80R dose tested (undiluted, 250 μg/mouse, ≅12.5 mg/kg body weight), 4/4 mice had a more than 4 log reduction in viral load (to below the assay limit), whereas the equivalent amount of human IgG1 had no effect. At a dose of 50 ug/mouse, ¼ of the mice again showed a viral load reduction to below the limit of detection and ¾ of the mice showed a nearly 4 log reduction in viral titer. At the lowest dose (1:25 dilution, 10 μg/mouse), 4/4 mice became infected and the virus load was reduced about 10-fold.

This level of protection is comparable to that seen when the animals were injected with convalescent sera from previously infected mice (see Subbarao et al., J Virol 78:3572-77 (2004)). These results indicate that the prophylactic administration of 80R can efficiently protect mice from SARS-CoV infection.

TABLE 3

Protection from virus replication in the lower respiratory tract of mice following passive transfer of an anti-SARS monoclonal antibody 80R

| Passive transfer MAb[1] (500 μg/ml) | # infected/ # tested | Virus replication in lungs of challenged mice[2] Mean (± SE) virus titer[4] | P Value[3] |
|---|---|---|---|
| Undiluted control MAb | 4/4 | 5.7 ± 0.1 | |
| 80R undiluted | 0/4 | ≦1.5 ± 0* | 0.00000001 |
| 80R diluted 1:5 | 3/4 | 2.0 ± 0.2 | 0.0000035 |
| 80R diluted 1:25 | 4/4 | 4.6 ± 0.26 | 0.007 |

[1]The indicated dilutions of Ab in 500 μl were administered to recipient mice by intraperitoneal injection.
[2]Mice were challenged with $10^4$ $TCID_{50}$ SARS-CoV intranasally.
[3]P values comparing titers with those seen in mice that received the control antibody in a two-tailed Student's t-test.
[4]Virus titers are expressed as $log_{10}$ $TCID_{50}$/gm of tissue.
*Virus not detected; the lower limit of detection of infectious virus in a 10% w/v suspension of lung homogenate was 1.5 $log_{10}$ $TCID_{50}$/gm.

Example 10

Construction of Full Length Spike, S1-Ig, Truncation Variants, and Mutants

The plasmid encoding a codon-optimized form of the S1 gene (residues 12-672 was defined as S1 domain of the SARS-CoV S protein), fused with the Fc portion of human IgG1 (S1-Ig), was previously described (see Li et al., J. Virol. 78:11429-33 (2004); Li et al., Nature 426:450-54 (2003); Wong et al., J Biol Chem 279:3197-201 (2004)). Plasmids encoding residues 318-510, 327-510, 318-490 and other truncation variants of S1 were generated by PCR using S1-Ig as a template.

Mutations within S1-Ig or within S1(318-510)-Ig were generated by site-directed mutagenesis using the QuikChange method (Stratagene). S1 or full-length spike genes of SARS-CoV Tor2 (GenBank accession number: AY274119), GD03T (GenBank accession number: AY525636) and SARS-like-CoV SZ3 (GenBank accession number: AY304486) were generated de novo by recursive PCR. Full-length spike proteins for immunoprecipitation were fused with a carboxyl-terminal nine amino-acid (C9) tag (see Li et al., Nature 426:450-54 (2003); Moore et al., J Virol 78:10628-35 92004)). All variants and mutations were confirmed by DNA sequencing.

Example 11

Radioimmunoprecipitation of S1, Truncation Variants and Mutations

S1-Ig, S1(318-510)-Ig, and other truncations and mutations were expressed in 293T cells, secreted in culture supernatants and metabolically labeled for 24 h with [$^{35}$S]-cysteine and [$^{35}$S]-methionine (NEN Life Science). 1 μg of 80R scFv was conjugated to 20 μl of anti-His6 agarose beads in PBS buffer by incubating 2 h at 4° C. and followed by washing 2 times with 1 ml of PBS. The 80R scFv beads were used to precipitate Fc-tagged S1 or its derivates. 500 μl of culture supernatants which contains metabolically labeled S1 or its derivates were incubated with beads for 4 h at 4° C., then beads were washed three times with PBS containing 0.25% Nonidet P40. Full-length S protein were also expressed in 293T cells and metabolically labeled, cells were lysed with 1% CHAPSO/PBS. 1 μg of 80R IgG1 or anti-C9 antibody 1D4 was used to precipitate S protein from cellular lysate. Bound proteins were eluted in reducing Laemmli sample buffer at 100° C. for 5 min. Proteins were subjected to 10% SDS/PAGE, visualized by phosphorimaging, and quantified using ImageQuant software.

80R Neutralizing Determinants are Located within the ACE2 Receptor Binding Domain 80R scFv-conjugated agarose and Protein A Sepharose were individually used to precipitate a metabolically labeled Fc-tagged soluble form of these three S1 truncations. The amount of S1-Ig protein precipitated by 80R scFv was normalized to the amount precipitated by Protein-A. As shown in FIG. 9A, the variants expressed similar amount of proteins, as demonstrated by Protein A precipitation. 80R scFv precipitated the 193-aa fragment S1(318-510)-Ig as efficiently as Protein A. However, under similar conditions, 80R scFv did not precipitate the smaller deletion of S1(318-490), and it precipitated only 5% of the amount of S1(327-510) that Protein A precipitated. This same precipitation pattern was observed in ACE2 precipitation studies using these variants.

These data indicate that the 80R neutralizing determinant and the ACE2 receptor-binding domain are located within the same domain of the S protein, specifically, between residues 318 and 510. Both smaller N-terminal and C-terminal deletion variants of this domain (318-490 and 327-510, respectively) lost 80R-binding activity, which implies that some residues in the N-terminal and C-terminal of S1(318 to 510) contribute either directly to the binding of 80R with this domain or to the folding of the correct antibody-binding domain.

A further series of slightly smaller Fc-tagged N-terminal and C-terminal deletions of S1(318-510) were made to define the smallest binding domain of monoclonal antibody 80R. As shown in FIG. 9A, the 321-503 variant expressed as well as S1(318-510) and displayed the same 80R binding activity as S1(318-510). The variant 321-500 did not express well and 80R binding was not detectable. However, the 80R binding of variant 324-503 remained the same as for S1(318-510) even though its expression was greatly reduced Therefore, the smallest 80R binding domain is located within amino acids 324-503.

Identification of Some Important Residues for 80R Binding
to the ACE2 Receptor-Binding Domain of S1 Protein Some acidic residues between amino acid residues 318 and 510 (glutamic acid 452 and aspartic acid 454, 463 and 480) were previously individually substituted to alanine to test their effect on association with ACE2. It was shown that E452 and D454 individually made important contributions to the S1 interaction with ACE2. D463A alteration also resulted in a decrease of ACE2 binding, but no effect was found with a D480A alteration. (See Wong et al, J Biol Chem 279:3197-201 (2004)).

These point-substitution variants were tested for 80R antibody binding. Specifically, they were mutated to alanine individually in both S1(318-510)-Ig and in full-length S1-Ig. Protein A and 80R-scFv-conjugated beads were used to precipitate metabolically labeled S1(318-510)-Ig, S1-Ig or their variants. A ratio of one was set for the amount of 80R-scFv-precipitated S1(318-510)-Ig or S1-Ig to that of Protein A—precipitated S1(318-510)-Ig or S1-Ig, and the amount of 80R-scFv-precipitated variants was normalized accordingly. As shown in FIG. 9B, E452A and D463A variants were precipitated ~10% and 100% of wild type S1(318-510)-Ig by 80R scFv, respectively. D454A and D480A variants were not detectable on precipitation with 80R scFv. The same result was obtained for variants in S1-Ig.

Example 12

80R Inhibition of Infection by
S-Protein-Pseudotyped Viruses

S-protein-pseudotyped lentiviruses expressing a luciferase reporter gene were produced as described previously (see Naldini et al., Proc. Natl. Acad. Sci. USA 93:11382-88 (1996); Yang et al., J Virol 78:5642-50 (2004)). Briefly, 293T cells were cotransfected with a plasmid encoding S-protein variants with a modified carboxyl-terminal ht2(15), a plasmid pCMVΔR8.2 encoding HIV-1 Gag-Pol, and a plasmid pHIV-Luc encoding the firefly luciferase reporter gene under control of the HIV-1 long terminal repeat. Forty-eight hours posttransfection, viral supernatants were harvested and 5 μl of S-protein-pseudotyped virus was used for infection of 6,000 ACE2-expressing 293T cells in 96 well plate. Infection efficiency was quantitated by measuring the luciferase activity in the target cells with an EG&G Berthold Microplate Luminometer LB 96V.

Figure 10A:
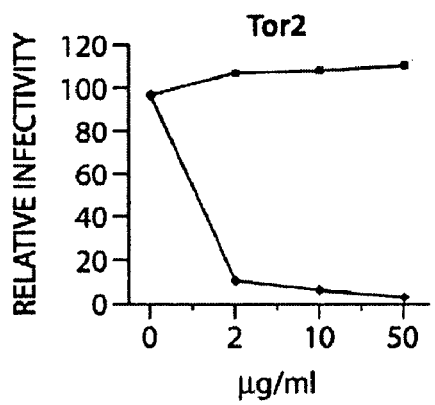
FIG. 10A shows that 80R IgG1 efficiently blocked Tor2 S protein pseudotyped HIV viral infection, with a 90% inhibitory concentration around 2 µg/ml.
Figure 10B:
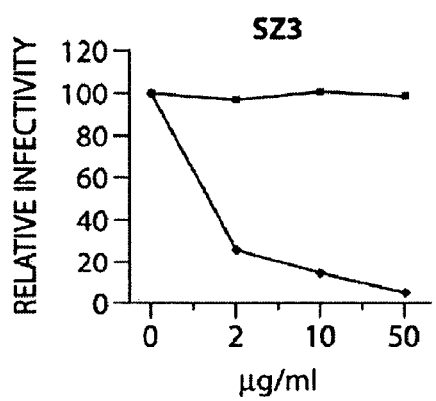
FIG. 10B shows that 80R IgG1 also efficiently neutralized SZ3 S protein pseudoviral infection.
Figure 10C:
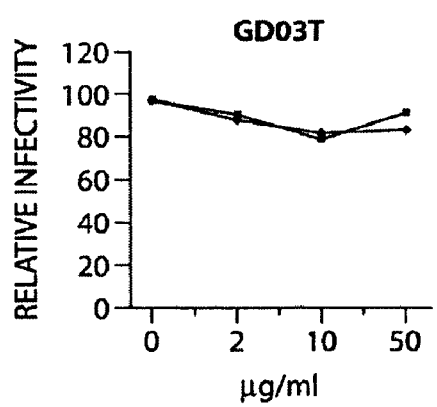
FIG. 10c shows that, in contrast to Tor2 and SZ3, GD03T S protein pseudotyped viruses was essentially resistant to the neutralization of 80R IgG1 with a concentration up to 50 µg/ml. These results are representatives of two experiments with similar results.

The neutralization activity of 80R against variant SARS-CoV was evaluated by using a pseudoviruses system. HIV viruses pseudotyped by S protein variants of Tor2, SZ3 or GD03T were tested for neutralization sensitivity to increasing concentration of 80R IgG1 or non-relevant human IgG1. As expected, Tor2 is very sensitive to neutralization of 80R IgG1, with a 90% inhibitory concentration around 2 ug/ml (FIG. 10A). 80R IgG1 could also efficiently block SZ3 pseudoviral infection (FIG. 10B). In contrast, GD03T is essentially resistant to the neutralization of 80R IgG1 in the concentration range assayed (FIG. 10C).

Example 13

De-Glycosylation of S1-Ig and Western Blotting
with ScFv

Purified S1-Ig was de-glycosylated with PNGase F (New England Biolabs, Beverley, Mass.), an enzyme that removes N-linked glycosylation, under denaturing conditions according to the manufacturer's instructions. For Western blotting, untreated or de-glycosylated S1-Ig (50 ng) were denaturated or reduced by boiling in 20 μl denaturing (1% SDS) or reducing (50 mM DTT, 1% SDS) sample buffers and run on 10% SDS-PAGE. The S1 were blotted by anti-S1 scFv and followed by polyclonal rabbit anti-His$_6$ antibody (Santa Cruz) and then HRP-labeled anti-rabbit IgG (Pierce). The luminometric detection was performed using the SuperSignal Chemiluminescent substrate kit (Pierce).

Example 14

Identification of Anti-S1 Phage Antibodies,
Expression and Purification of Soluble scFvs Purified recombinant S1-C9 was used as antigen to select antibodies from two non-immune human scFv libraries. After three rounds of selection on S1-C9, a total of 288 clones were screened for S1 specific binding by ELISA. 104 clones specifically recognized S1-C9 protein, but not HIV-1 gp120-C9 and BSA control proteins. Eight unique anti-S1 scFvs were identified (ScFvs 6A, 8C, 12E, 26H, 27D, 80R, 91M, 92N) by sequencing analysis of the individual clones. Further, the eight scFvs tagged with His$_6$ were expressed in E. coli and purified by IMAC. Vector pSyn1 was used for expression of the 6A, 80R, 91M and 92N, and vector pET22b(+) was used for the other four scFvs (8C, 12E, 26H, 27D) expression because of their lower expression level in pSyn1. The binding activity and specificity of the scFvs were confirmed by ELISA with S1-C9 and S1-Ig.

Example 15

Phage Peptide Mapping of the 80R Epitope on S1
Protein

In a preliminary attempt to fine map the region of S1 recognized by the scFv 80R neutralizing antibody, scFv 80R was used to affinity select ten phage display random peptide libraries, in which phage-displayed peptides are encoded by synthetic random degenerate oligonucleotide inserts. The libraries differed with respect to display format and the presence or absence of constraints imposed by disulfide bonded cysteine molecules in fixed positions. (See Matthews. et al., J. Immunol. 169:837 (2002)).

Purified scFv 80R was used to affinity-select phage-borne peptides from each of the ten libraries by the "one-step" method. (See Yu and Smith, Methods in Enzymology 267:3 (1996)). Following three rounds of affinity-selection, forty-eight individual clones were propagated from the output of each of the ten libraries. These 480 clones were screened for ability to bind to scFv 80R by ELISA. 284 clones were positive according to the criterion that their ELISA binding activity for 80R was at least 5 times their binding activity for a control, irrelevant scFv with similar VH and VL gene family framework. 120 clones showing the highest ELISA activity, including at least eight from each of the eight libraries with positive clones, were DNA sequenced to deduce the amino acid sequence of the displayed peptide. Seven of the peptide sequences aligned somewhat to sequences in the S1 protein. (See FIG. 6).

Figure 7:
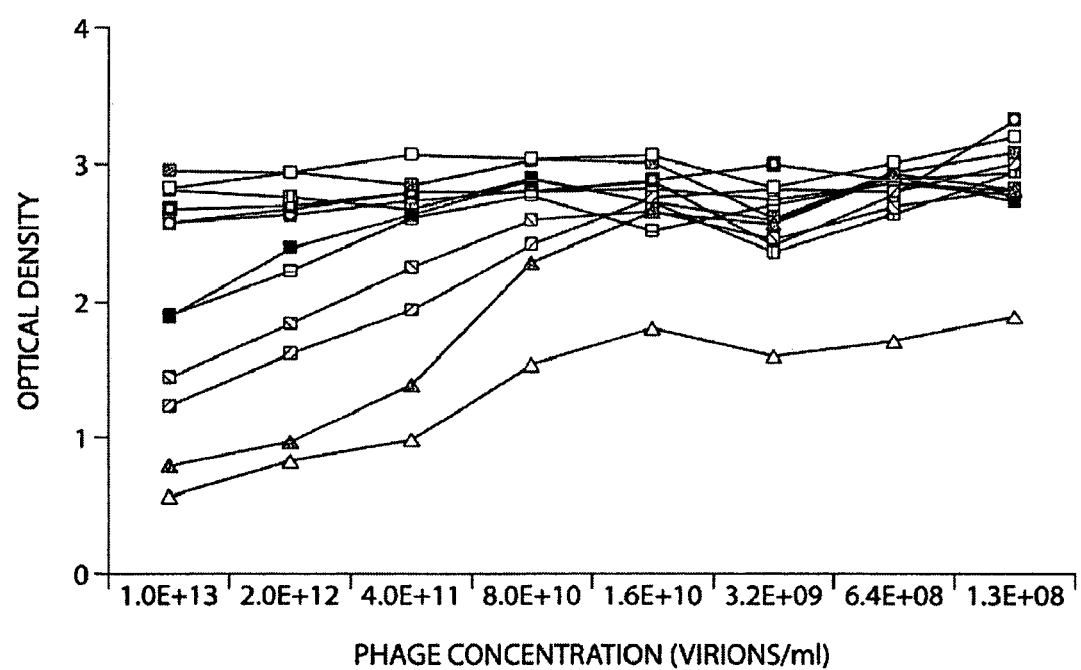
FIG. 7 is a graph showing inhibition of scFv 80R binding to S1 protein by selected phage displayed peptides. Pre-mixed his-tagged scFv 80R (1 μg/ml) and serially-diluted phage were added to wells of a microtiter dish that had been coated with purified Spike protein (0.15 μg/well) in a final volume of 100 μl. After washing the wells, rabbit anti-his antibody was added and binding activity was detected by anti-rabbit antibody conjugated to HRP. (■) Phage-displayed peptides showing moderate or no inhibition. (▲) Phage displayed peptide (CLSATCDCTLCGP) (SEQ ID NO:40), showing substantial inhibition. (□) Negative control; phage clone which showed no binding to S180. (Δ) Positive control; 2-fold serial dilutions (highest concentration 40 μg/ml) of purified Spike protein were added to the wells.

Eleven phage clones, including the seven which showed some sequence similarity to the SARS Spike protein, were tested for the ability to block scFv 80R binding to the Spike protein (See FIG. 7). One phage-displayed peptide (CLSATCDCTLCGP (SEQ ID NO:26), see FIG. 7) substantially inhibited binding of scFv 80R to Spike protein (▲, FIG. 7), while a few others inhibited binding moderately.

There appears to be a discrepancy between this data (which was obtained using S1 phage panning studies) and the data which was obtained using cellulose membrane staining, wherein the peptides were synthesized based on deletional studies and represent real amino acid sequences of the SARS-CoV S1 protein. In contrast, the peptides isolated in FIG. 6 were obtained from a random peptide library. Thus, those skilled in the art will recognize that two complementary methods were used to obtain this data and that these two methods gave discrepant results. Additional studies will be needed to determine which results are correct. Experiments to verify which peptide is correct will ultimately determine which of the two methods described herein is correct. For example, Enshell-Seijffers et al. describe a computer algorithm, which can be used to help decode conformational discontinuous epitopes. (See Enshell-Seijffers et al., J. Mol. Biol. 334:87-101 (2003), incorporated herein by reference). Moreover, the co-crystal structure of 80R scFv and S1(318-510) will provide additional information regarding the random peptide data of FIG. 6.

Until the correct peptide is verified experimentally, those skilled in the art will recognize that it is likely that either of the peptides isolated in FIG. 6 could be incorporated as antigens. However, it should be noted that the data presented is most consistent with the extensive epitope mapping data presented in FIGS. 8 and 9.

Example 16

Design of SARS-CoV Spike/Membrane Fusion Proteins as Protein and DNA Vaccines

Different forms of IgG molecules, single-chain Fv fragments (scFv), Fab, scFv-Fc, and/or full-length IgG can be produced in various cell types. A large collection of IgG- or Fc-containing DNA plasmids and lentiviral transfer plasmids can be utilized to produce these molecules. For example, SARS S1, S2 or M-IgG fusion proteins can be used for protein and DNA vaccines. IgG-fusion scaffolds can be created that present SARS-related epitopes in a format that is optimal for vaccination.

To test for expression and secretion, DNA plasmids encoding SARS-IgG fusions are transiently transfected into 293T cells. The presence of secreted fusion proteins in the culture supernatants is determined by (1) a quantitative ELISA using goat-anti-human IgG1-Fc sandwich assay (Bethyl Laboratories) and (2) SDS-PAGE analysis of the secreted, Protein G affinity-purified, $^{35}$S-met/cys metabolically labeled fusion proteins.

It has been found that the intrachain-linker (ICL) of an scFv antibody can accommodate a properly folded loop structure of ~30 amino acids in length while preserving its antigen binding specificity. (See Q. Zhu and W. Marasco, unpublished data). This experimental finding can be exploited by engrafting loop structures into the ICL from neutralizing epitopes, such as the 80R epitope, when the fine structure of this and other discovered epitopes are revealed.

Example 17

Production of GLP Grade 80R hMAb to be Tested as an Immunoprophylaxis and Treatment Strategy Against SARS in an Animal Model Animal models of SARS infection in the mouse and African Green Monkey are used to perform prophylaxis model and post exposure treatment model experiments. Currently, both models are infection models rather than pathogenesis models. However, it is hoped that a pathogenesis model will evolve that will be used to see if the 80R MAb can block the clinical development of SARS in a pre- and post-exposure model. Establishment of a high secretor 80R hMAb transfectoma cell line and purification of gram quantities of 80R MAb will be needed to move forward into non-human primate studies.

The expression levels of transfected genes in mammalian cells are primarily determined by the cellular DNA at the site of integration. The human immunoglobulin IgG1 kappa expression vector 80R TCAE5 will be utilized to target mammalian loci that support high levels of expression. These vectors encode immunoglobulin heavy and light chain genes, the dihydrofolate reductase (DHFR) gene, and the dominant selectable marker neomycin phosphotransferase (Neo) gene. By intentional impairment of the Kozak sequence surrounding the Neomycin initiation codon to create a fully impaired Kozak sequence, most single copy integrants will not express enough Neo to survive selection. (See Kozak, Nucleic Acid Research 15:8125-32 (1987)). The result is that the overall number of G418 resistant cells is greatly reduced, facilitating screening. A higher percentage of the clones surviving selection are those in which the impaired Neo gene has been integrated into "hot spots" with the genome, which concomitantly yield very high levels of linked gene expression. (See Barnett et al., in Antibody Expression and Engineering, Chapter 3, pgs. 27-40 (1995)).

Once isolated, transfectants which display a very high level of immunoglobulin protein production are induced to undergo gene amplification by selection in methotrexate (MTX) for the dihydrofolate reductase gene (Kaufman and Sharp, J. Molecular Biology 159:601-602 (1982)). As the DHFR gene copy number increases through amplification, there is a parallel increase in the closely linked immunoglobulin gene copy number with an accompanying rise in immunoglobulin production. Amplification of initially very high level expression clones yields cells producing even greater levels of immunoglobulin protein from a minimal number of gene copies (Reff et al., Blood 83:435-45 (1994)).

2-4 µg plasmid DNA is transfected by electroporation into $4\times10^6$ CHO DG44 cells (adapted to grow in serum free media) and then selected for G418 resistance. At least 100 G418 resistant colonies (from circa twenty 96 well plates) are screened for IgG production (anti-human IgG ELISA) when they are between 30% to 100% confluent, i.e. 30,000 to 100,000 cells. The 10-12 highest Ig producers will be expanded and HMW DNA will be isolated for Southern blotting to determine the number of integrated copies. This is accomplished by using 5 mg HMW DNA digested with EcoR1 which cuts once in each plasmid, giving two bands of different sized for each integration site into cellular DNA.

The three highest Ig producing, lowest copy number cells are then subjected to gene amplification by using increasing concentrations of MTX (5 nM→50 nM→500 nM). At the 5 nM MTX stage, the best amplificants from each of the three G418 clones are further amplified at the 50 nM and 500 nM stage. At this stage, the selected amplificants are readapted to grow in spinner flasks. During this time transfectoma antibody can be purified from the supernatants over protein A. When the cell is producing 50 pg/cell/day and has a doubling time of 36 hours or less, it will be considered to be a production cell line and a Parent Seed Stock will be prepared. This total process will take approximately 35-45 weeks to complete. However, culture supernatants can be harvested earlier for characterization of the 80R.

Initially, animal studies are performed at 1 mg/kg and 10 mg/kg doses of MAb IgG. In the mouse studies, the amount of protein needed is rather small and can be produced by transient transfection of 293T cells and purification on Protein A columns. Three groups of four mice each are given a different concentration of 80R i.p. 24 hours prior to intranasal exposure with SARS-CoV. Prior to challenge a bleed is obtained to measure the serum concentration of the 80R MAb. The animals are then inoculated with virus 48 hrs later, the lungs are harvested, the tissue prepared, and the virus titers are performed on Vero-E6 cells. The current assay used is a virus titer reduction assay from the target organ, (i.e., lung).

Example 18

Study of SARS-CoV Escape from MAb 80R

SARS-CoV, like HIV, is an RNA virus whose replication is error-prone. The high rate of genetic mutation can lead to evolution of new viral strains and is a mechanism by which viruses escape host defenses. Studies of 14 separate SARS strains that emerged from a single source suggest a pattern of evolution in response to immune pressure. (See Ruan, et al., The Lancet 361 (9371):1779-1785 (2003)). Some coronaviruses are well known to mutate to escape from host immune response.

The mutation pattern of SARS is important both in its pathogenesis and its control in the case of a possible disease emergence. Examination of neutralizing antibody escape mutants in vitro using the neutralizing antibody 80R will provide information regarding whether the escape mutants would emerge during in vitro treatment of SARS-CoV infection.

If neutralization escape does occur, the biological characteristics of the mutant viruses will be tested to determine if they are more or less cytopathic and whether S1 escape viruses encode an S1 protein that has a higher affinity for the S1 receptor out compete the neutralizing antibody for binding to ACE2.

Development of Neutralization Escape Mutants from 80R MAb

Strategy I

To develop 80R escape mutants, the IC90 of 80R to neutralize the SARS-CoV infection in Vero-E6 cells is determined using the microneutralizing assay described above. (See Example 4, supra). The procedure for generation of mutants reported by Dalziel, et al., J. Virol. 59:4636, 71 (1986) and Yoo et al., Clin. Diagn. Lab. Immunol. 8:297-302 (2001), can be modified and used to develop 80R escape SARS-CoV mutants. An equal volume of neat wild-type SARS-CoV (Urbani strain) and 80R neutralizing antibody is incubated at 37° C. for 60 min and then is added to Vero-E6 cells in a 6-well plates at 37° C. for 1 h.

As a control, cells are treated with an identical concentration of an irrelevant hMAb. Next, the virus inoculum is removed and the cells are overlaid with 0.7% agarose containing a range of different concentrations of MAb 80R, including a 10 fold lesser amount of 80R MAb. At three days of incubation, the cells will be stained to visualize plaques. Plaques are first picked from the plates containing the highest concentration of 80R MAb and resuspended in 1 ml of medium. Partial resistant plaques are isolated from plates that are treated with lower concentrations of 80R MAb. The plaque-picked viruses are propagated in Vero-E6 cells in the presence of 80R MAb for three passages until a cytopathic effect is evident. Ten-fold dilutions of the passaged virus are then incubated in presence or absence of 80R MAb and are propagated in the plaque assay to confirm a MAb resistance phenotype and to generate plaque-purified (subcloned) mutant viruses. Passage in the absence of 80R MAb also serves as a control to determine if the 80R resistant phenotype is stable in the absence of selection pressure. Subclones of the escape virus mutant are propagated in Vero cells, retested for the 80R resistant mutant phenotype, aliquoted, and stored at −70° C. To perform DNA sequencing and sequence analysis of the 80R resistant viruses, Total RNA is extracted from fresh Vero cells that have been infected with the 80R resistant viruses. RT-PCR is performed with primers specific for the S gene of SARS-CoV to amplify the S gene mutants.

To determine if there is a discernable pattern of S1 amino acid differences in the different S1 mutants showing resistance to the 80R MAb, the PCR products are cloned in Topo cloning vectors. DNA is sequenced and predicted amino acids sequences of the mutants are determined. The S1 protein sequence is evaluated for amino acid changes of the partial and resistant viruses. For these studies, ten full-length S1 gene sequences from the partial and resistant viruses are cloned by PCR and DNA sequenced and these DNA sequences are compared to S1 genes that are cloned from control (irrelevant MAb treated) viruses isolated from the same time points. DNA sequence alignments are performed to determine if any DNA sequence changes that have been reported to occur naturally in human SARS-CoV infections can be identified. (See Ruan, et al., The Lancet 361 (9371): 1779-1785 (2003)).

Strategy II

Experiment A:

1) 100 μl SARS-CoV ($1 \times 10^5$ PFU [plaque forming units]) with equal volumes of ½ serial dilutions of hMAb 80R (i.e. with final dilutions from 1:100-1:3200) was incubated in a 37° C./$CO_2$ humidified incubator for 45 minutes. The experiment was run in triplicate.

2) The "virus+80R" mixtures were adsorbed separately onto Vero-E6 monolayer in 24 wells tissue culture plate. Adsorption took place for 45 minutes in a 37° C./$CO_2$ humidified incubator.

3) The "virus+80R" inoculums were removed, and 1 ml of MEM-agarose was added to each wells. The MEM-agarose was left to solidify for 20 minutes at room temperature and was later incubated in a 37° C./$CO_2$ humidified incubator for 2 days.

4) The plaques were visible under inverted microscope on 2 days post infection. The plates were stained with neutral red-PBS staining and were left in a 37° C./$CO_2$ humidified incubator overnight.

Results: The number of plaques observed per dilution of 80R: 1:100 (5, 4, 0); 1:200 (13, 14, 14); 1:400 (discernible plaques but too many to count), 1: 800 and higher (complete lysis of monolayers).

Experiment B:

1) Using sterile pasteur pipette, 15 plaques were isolated from the 1:100 and 1:200 dilutions, and saved them (separately) in 200 uls of MEM. The plaques were frozen and thawed 3×.

2) Vero-E6 monolayer were infected in 24 wells tissue culture plates and allowed to adsorb in a 37° C./$CO_2$ humidified incubator for 45 minutes.

3) 300 μls MEM/5% fcs were added to each well and the corresponding final dilutions of 80R. These were left in a 37° C./$CO_2$ humidified incubator for 3-5 days.

Results: While only one plaque isolated at 1:100 dilution of 80R produced cytopathic effect (CPE), three plaques from 1:200 dilution showed CPE. The infected cells were harvested separately, frozen and thawed 3×, and labeled as "1° (primary) lysates" of 1:100, or 1:200 (A, B, and C).

Experiment C:

1) 200 μls of each of the four "1° lysates" were incubated with corresponding 1:100, or 1:200 dilutions of 80R separately, and incubated in a 37° C./$CO_2$ humidified incubator for 45 minutes.

2) The lysate+80R mixture was separately adsorbed onto Vero-E6 monolayer in 24 tissue culture plates and allowed to adsorb in a 37° C./$CO_2$ humidified incubator for 45 minutes.

3) 300 μls of fresh MEM/fcs was added to each of the infection as well as corresponding final dilutions of 80R. Incubation continued in a 37° C./$CO_2$ humidified incubator for 2-3 days.

Results: All the four primary lysates showed good CPE by day 2. They were harvested as before (2° [secondary] lysates) and frozen and thawed 3×. Experiment C was repeated in 25 cm² flask for each 2° lysates. After day 2, all flasks showed good CPE. They were harvested as before (3° [tertiary] lysates) and frozen and thawed 3×.

Strategy III

Experiment A:

1) 100 μls (1×10⁵ PFU), 10 μls (1×10⁴ PFU), and 1 μl (1×10³ PFU) of stock SARS-CoV was mixed separately with 100 μls of MEM containing either 1:200, or 1:400 final dilutions of 80R. The virus-80R mixtures were incubated in a 37° C./$CO_2$ humidified incubator for 45 minutes.

2) Each virus-80R mixture was adsorbed onto Vero-E6 monolayer cells in 24 tissue culture plates in a 37° C./$CO_2$ humidified incubator for 45 minutes.

3) 300 μls of fresh MEM/fcs was added to each of the infections as well as corresponding final dilutions of 80R. Incubation continued in a 37° C./$CO_2$ humidified incubator for 3-5 days. Plates were observed daily for CPE.

Results: Only three mixtures showed CPE—1:200 (100 μls), 1:400 (100 μls), and 1:400 (10 μls). These were harvested (+1 lysates) separately and were freeze-thawed 3×.

Experiment B:

1) 200 μls of each "+1 lysates" were separately mixed with corresponding dilutions of 80R and were incubated in a 37° C./CO2 humidified incubator for 45 minutes.

2) Each "+1 lysates-80R mixtures" was adsorbed onto Vero-E6 monolayer cells in 24 tissue culture plates in a 37° C./$CO_2$ humidified incubator for 45 minutes 3) 300 μls of fresh MEM/fcs was added to each of the infection as well as corresponding final dilutions of 80R. Incubation continued in a 37° C./$CO_2$ humidified incubator for 3-5 days. Plates were observed daily for CPE.

Results: All three showed good CPE by day 2 (+2 lysates). These were harvested and freeze-thawed 3×. Experiment B was repeated for "+2 lysates" to obtain "+3 lysates." Similarly, Experiment B was repeated for "+3 lysates" in a 25 cm² flasks to get "+4 lysate" stocks for each samples.

Future Studies

Subsequent experiments will focus on the "3° lysates" from Strategy II. Initially, each lysate will be titrated for the highest dilutions that will give complete lysis of Vero-E6 monolayers in triplicate wells in 96 wells tissue culture plates. Next, the SARS-MNt assay will be performed on each lysate in the presence or absence of serial dilutions of 80R. The control virus will be the original stock of SARS-CoV. Complete lysis in the presence of 80R compared to control will suggest the lysate is an "80R-escape-mutant." If that so, the lysate will be treated with RNA extraction buffer for subsequent molecular biological analyses Expression of Mutant S Proteins and Examination of their Receptor and Neutralizing Antibody Binding Activities.

In order to determine whether the mechanism for resistance is due to the ability of the virus to bind ACE2 with higher affinity, the mutant S1 genes of interest are cloned into pcDNA 3.1 with C9 tag for expression. Mutant S1-C9 protein is radio-labeled in 293T cells. To test binding activity to ACE2, the [$^{35}$S-methionine/cysteine] radiolabelled mutant S1 proteins are mixed with soluble ACE2 receptor and immunoprecipitated with anti-ACE2 antibody. The mixture is incubated with protein A sepharose beads for one hour at 4° C., after washing four times with PBS containing 0.25% $NP_{40}$ and 0.01% SDS, the bound proteins are eluted in reducing sample buffer at 100° C. for 5 mins. Proteins are separated by 8% SDS-PAGE and visualized by autoradiography on Kodak Biomax MR film.

By comparing the ACE2 binding properties of both the wild-type and mutant S1 proteins, a determination can be made regarding whether the mutant S1 proteins have higher binding affinities for soluble ACE2 receptor. A similar cell labeling experiment can be performed where different concentrations of radiolabelled wild-type and mutant S1 proteins are incubated with a fixed number of Vero cells, and the radioactive S1 protein bound to the cells can be measured after washing.

Saturable cell binding at lower concentrations of radiolabelled mutant S1 protein would indicate higher affinity binding to ACE2. BIAcore analysis is used to directly measure the affinity binding constants between ACE2 the mutant S1 proteins.

In order to determine whether the mechanism of resistance is due to the lower affinity binding of 80R scFv and IgG1 to the mutant S1 proteins, mutant S1-Ig proteins can be produced and the binding kinetics and affinity of 80R scFv, 80R-IgG1 and receptor ACE2 to the purified S1-Ig can be measured by surface plasmon resonance (BIAcore 3000, Sweden). Purified S1-Ig are covalently immobilized to a CM5 sensor chip via amine group using the amine coupling kit (BIAcore) in 10 mM sodium acetate, pH 4.5 buffer, yielding a surface of 6388 resonance units. Experiments are run at a flow rate of 10 μl/min in HBS-EP buffer (BIAcore). The surface is regenerated with 10 mM glycine-HCl, pH 2.0. Binding kinetic parameters are measured with antibodies or receptor at different molar concentrations and evaluated with the BIA-evaluation 3000 software. Binding constants for the soluble antibodies and ACE2 for binding are compared to the wild-type and mutant S1-Ig proteins.

To determine whether the mechanism of resistance is due to the ability of the virus to better compete for ACE2 receptor binding, the ability of 80R scFv or 80R IgG1 to compete with wild-type or mutant S1 proteins for binding to soluble or cell surface ACE is examined. The requirement for higher concentrations of antibody to compete with mutant S1 for binding to ACE2 would indicate that one mechanism of resistance is that the mutant S1 proteins bind with higher affinity to ACE2.

An increase in S1 binding affinity to ACE2 would suggest that the mutant S1 viruses could enter cells expressing lower concentrations of ACE2. This can be tested using a cell line that expresses ACE2 under the control of a tetracycline switch. A similar approach has recently been reported to examine HIV-1 escape mutants to a CCR5 antagonist. (See Reeves et al., Proc. Natl. Sci. USA 99 (25):16249-54 (2002)). The construction of a self-inactivating (SIN) lentiviral vector that allows tightly regulated tetracycline inducible gene expression in transduced cells has recently been described. (See Ogueta et al., Mol. Med. 7(8):569-79 (2001) and Zhu, et al., Gene Ther Mol Biol. 8:91-102 (2004)).

Cf2 cells (canine thymocyte cell line), which does not express ACE2, are transduced with the tetracycline inducible SIN vector encoding ACE2 under the control of a tetracycline switch (SINmin1piACE2). Purified clonal populations of transduced cells are obtained. Cells are treated with varying concentrations of tetracycline to induce ACE2 expression from low (circa 1000-5000) to high (circa 50,000) levels. ACE2 expression levels is followed by FACS using FITC-labeled anti-ACE2 MAb. Pseudotyping wild-type and mutant S1 proteins onto MuLV or HIV-1 luciferase reporter viruses will be attempted. The optimal conditions for S1 pseudotyping remain to be determined. Virus entry is studied at various time points after infection to determine if the kinetics and magnitude of infection are accelerated due to a higher affinity interaction. If the mutant viruses are more efficient at entering cells expressing lower levels of ACE2, the range of host cells that can be infected with the mutant viruses would likely increase.

To study the pathogenicity of the mutant S1 proteins, membrane fusion will be studied in vitro and SARS-CoV replication in vivo. 293T cells, approximately 30% confluent in T75 flask, are transfected with plasmids encoding the wild-type mutant S1 proteins or ACE2. One day after transfection, cells are trypsinized and washed once in medium. The S protein-expressing cells are mixed at different ratios with cells expressing receptor ACE2 and then plated on 24-well plates. Cells are cultured for 36 hours after mixing, multinucleated giant cells were observed, counted and representative photographs are taken. The numbers and sizes of the syncytium in the mutant S1 expressing cells are determined. If a syncytium-inducing curve that is shifted to the left (so that lower concentrations of mutant S1 give equivalent syncytium to wild-type S1 proteins) is observed, this would imply that the mutant S1 proteins are more pathogenic.

To test the pathogenicity in vivo, the replicative capacity of the 80R escape mutants will be examined in the mouse model until a pathogenic model is available in the non-human primates. Viruses expressing the mutant S1 proteins are sub-cloned as described above and are used to infect the mice by intranasal inoculation. 48 hours post inoculation, the mice are sacrificed, the lungs removed, and the titers of the SARS-CoV on VeroE6 cells from the lung tissue determined. A change in the kinetics or magnitude of infection implies that the mutant S1 proteins are more pathogenic, which would be confirmed by the loss of R80 MAb protection in this model.

Results

The data presented in FIGS. 8B, 8C, and 9B (regarding the D480G mutation) as well as in FIG. 10C (regarding the GD03T sequence) are in agreement with the data presented in Table 1, supra. In the GD03T patient, there is a D to G mutation at position 480, which led to complete resistance of the SARS virus to 80R neutralization. Additional in vitro studies are currently underway.

Example 19

Identification of Neutralizing Epitopes Other than 80R

Although the spike protein represents the major antigenic determinant for coronaviruses, passive immunization studies with murine hepatitis virus (MHV) have demonstrated protection after administration of MAb specific for all major structural proteins of the virus.

As described in Example 2, supra, the 27 billion member non-immune human scFv library to screen for neutralizing antibodies against S1. However, only 288 individual clones were screened after three rounds of selection and one neutralizing anti-S1 antibody, (80R), was identified, which blocked the binding of S1 to its receptor. Tens of thousands of clones were isolated from this third round of panning, and it is likely that many more anti-S1 scFvs have been selected for and that some of these may be directed against different neutralizing epitopes on S1. Thus, a Tecan robot can be used to establish a high-throughput and efficient approach to large scale screening of antibodies from the panned anti-S1 sub-library. This will allow the identification of many new anti-S1 neutralizing antibodies. The Tecan robot will assist in the liquid handling of the large numbers of phage that will be examined when the higher throughput screens are performed on many more thousands of phage.

In addition to rescreening the panned anti-S1 sub-library, panning will also be performed on another functional domain of S protein, the S2 domain, since this domain is responsible for membrane fusion and therefore should also be a useful target for generating neutralizing human antibodies. Moreover, the M glycoprotein is the most abundant transmembrane envelope glycoprotein in the virus particle, and neutralizing epitopes have been reported to be present on M protein for other coronaviruses. (See Kida et al, Arch. Virol. 145:1-12 (2000)). Therefore, it may also be possible to identify neutralizing human antibodies against S2 and M protein from the non-immune human library.

A. SARS-CoV S1, S2 and M Protein Expression and Purification

Plasmids encoding the codon optimized S1 (residues 12-672) and S2 domain (residues 672-1255) of SARS-CoV S protein fused with C9 tag are obtained. The same codon optimizing strategy is applied to obtain the M protein coding DNA sequence and the de novo synthesized DNA-fragment are cloned into a modified pcDNA3.1 vector with C9 expressing tag. The plasmids will be transfected into 293T for recombinant protein expression and anti-C9 antibody 1D4 (National Cell Culture Center) conjugated protein A Sepharose are used for purification of C9-tagged proteins. The C9-tagged proteins are used for selection of phage display library and screening out of the target specific clones. The human IgG1 Fc fragment tagged S1, S2 and M protein will also be expressed because of its higher expression level and its easier purification procedure, as compared to C9-tagged proteins. These proteins will be expressed in 293T cells and purified by protein A Sepharose and they will be used for the further isolation and characterization of target specific antibodies.

B. Library Selection and Screening of Anti-S2 or
M Protein ScFv Expressing Phases (Phage-ScFvs).

Single clones are randomly picked and analyzed for specific binding to S1, S2 or M according to the methods of Example 2, supra. Briefly, 96-well Maxisorp immunoplates (Nunc) are coated with 0.2 µg/well of S1-C9, S2-C9, M-C9 protein or control proteins HIV-1 gp120-C9 and BSA, blocked with 4% nonfat milk/PBS. The detection system is developed by adding HRP-conjugated mouse anti-M13 and TMB substrate.

C. Production of Soluble Target Specific ScFv Abs

Soluble target specific scFv antibodies are produced as described in Example 3, supra.

D. Microneutralization Assay

Microneutralization assays are performed as described in Example 4, supra. Typically, the assays are done in triplicate and the neutralization titer is determined as the last dilution that shows inhibition of growth of ⅔ wells.

E. Syncytia Inhibition Assay for Anti-S1 or S2 Antibodies

Syncytion inhibition assays for anti-S1 or S2 antibodies are performed as described in Example 5, supra. Although it is unclear whether the anti-M neutralizing antibodies will be functional in this assay, they can also be tested for syncytion inhibition.

F. Affinity Measurement by BIAcore

The binding kinetics and affinity of scFvs, and IgG1s to the purified target protein are analyzed according to the procedures set forth in Example 6, supra.

Example 20

Development of SARS Vaccine Strategy

As compared to direct protein or synthetic peptide immunization, the use of "antigenized antibodies" in conjunction with DNA vaccination can significantly enhance antigen presentation and processing. (See Zanetti, Nature 355:476-77 (1992); Ulmer, Nat. Biotech 15:84243 (1997), and Bona et al., Immunol. Today 19:126-33 (1998)). The design and identification of optimal forms of S-IgG and M-IgG molecules as immunogens for induction of host immune responses against SARS viral proteins, which, in turn, may block infection by the SARS virus focuses on the following two major aspects:

1. Molecular cloning and in vitro characterization of novel APF-IgG fusion proteins containing antigenic protein fragments representing neutralization epitopes as determined by the studies described in FIGS. 6 and 11. The epitopes identified will be presented in different scaffolds within an IgG molecule in an effort to preserve their biological functions and/or proper structural features. In order to enhance the vaccine efficacy, the IgG scaffold will be designed to specifically target professional antigen presenting cells (APCs).

2. Testing immunogenicity of the APF-IgG fusion molecules by genetic immunization of mice using a "prime-boost" protocol. Due to the nature of the epitopes, the primary focus will be on characterization of humoral immune responses while monitoring the cell-mediated responses. The immunogenic fitness of each APF-IgG fusion antigen is determined. Ultimately, the best vaccine candidate will be judged by its ability to induce neutralizing antibodies that block SARS virus infection through in vitro neutralization assays.

The main challenges in establishing the SARS APFs as vaccine components include: proper conformational presentation, and maximal enhancement of antigen presentation and processing. Compared to the corresponding peptides, engrafting APFs into an IgG scaffold not only greatly enhances their antigenicity and immunogenicity but also improves immunogenic fitness by preserving the natural conformations of the epitopes within an IgG scaffold. In addition, the APF-Ig fusions should have a much longer serum half-life than their peptide counterparts.

This hypothesis is tested by designing and optimizing different types of APF fusion molecules using in vitro assays. The APF fusion molecules are then tested in vivo for their ability to induce immune responses. The results will provide important insight for rational design of an effective SARS vaccine.

A. Research Design and Methods

APFs are initially presented in two different forms within an IgG molecule: in a linear format as an in-frame fusion with the Fc fragment of a human IgG1 molecule and as a conformationally constrained epitope engrafted into the linker region of an human IgG1 scFv-Fc molecule. The secreted APF-IgG fusion proteins are purified and characterized in vitro. The APF-IgG fusion proteins are then be used as immunogens in a DNA-based prime-boost vaccine strategy in mice. In vitro analysis of the induced immunity includes evaluating both antibody and T-cell responses to the S and M proteins as well as the ability of immune sera to neutralize SARS viral infection in vitro.

Molecular Cloning of APF-IgG Fusion Proteins

Because human IgG1 can bind to murine DCs, the general format for the APF-Fc fusion clones will be: 5'CMV promoter-IgG leader-APF-human IgG1 Fc 3'. In order to present certain epitopes (APFs) in a conformationally constrained structure, they can be grafted into the loops of a novel scaffold in which the they will be inserted into the linker region of an scFv-Fc construct between the heavy ($V_H$) and light ($V_L$) variable regions of IgG. The linker region is utilized because it may be more flexible in adapting epitopes of greater length, since linker length up to 28 amino acids has been reported in engineering an scFv. (See Huston et al., Cell Biophy 22:189-24 (1993)). Moreover, using the linker as the antigen presentation site allows use of both the Fc region and the scFv (such as an anti-MHC II scFv) for APC targeting, thus creating a new multifunctional molecule and potentially enhancing antigen presentation. Based on previous studies with hCCR5 ECL2-IgG1 Fc fusion proteins, it is predicted that when $V_H$ interacts with $V_L$ and forms natural interchain disulfide bonds, the APF epitopes will loop out similarly to the conventional flexible linkers.

APFs are grafted into an anti-MHC class II scFv so that the scFv can serve as an in vivo APC targeting moiety for the APFs. An scFv with anti-mouse MHC II specificity is cloned from a hybridoma cell line such as 14-4-4S from ATCC. The DNA sequence encoding the heavy and light variable regions is PCR amplified from cDNA according to standard procedures. The anti-MHC II scFv is genetically linked to the human IgG1 Fc and is used to present APFs inserted in the linker region or to present APFs at the N-terminus following the leader sequence. Alternatively, the anti-MHC II scFv-Fc fragment can be engineered to favor heterodimer formation with the APF-Fc chimera as described by Carter, J. Immunol. Methods 248:7-15 (2001).

In Vitro Characterization of APF-IgG Fusion Proteins

Biochemical characterization of the fusion protein expression includes assays for secretion, post-translational modifications, and the ability of the APF-IgG fusion to block membrane fusion or viral entry, when appropriate.

One of the keys to success is the correct cleavage of the leader sequence, which leads to efficient secretion of the fusion proteins. Whether the fusion proteins are secreted as monomers or dimers is examined by SDS-PAGE analysis under reducing and non-reducing conditions or by gel filtration chromatography. To evaluate if the APFs are correctly glycosylated, the secreted fusion proteins are treated with glycosidases and analyzed by SDS-PAGE following Protein G isolation.

The ability of the APF-IgG fusion proteins to interfere with membrane fusion by binding to the SARS receptor expressed on 293T cells is assayed. In addition, the ability of APF-IgG fusions to interfere/neutralize SARS virus infection is evaluated in an in vitro microneutralization assay as described in Example 4, supra.

In Vitro Production of APF-IgG Fusion Proteins

To produce sufficient quantities of the secreted APF-IgG fusion proteins for biological assays and vaccination, it may be necessary to test different leader sequences for each individual construct in order to obtain correct cleavage and maximize secretion of the proteins. The secreted APF-Ig fusion proteins are first expressed using the Free-Style 293 Expression System from Invitrogen for large-scale protein production in a serum-free cell suspension environment. The APF-IgG fusion proteins are purified using Protein A/G affinity columns. Stable clones may need to be selected in order to establish a high producer cell line for each fusion protein. Lentiviral vectors with the identical IgG leader and Fc cassette could be utilized to aid stable integration of the APF-IgG fusion genes into the cellular genome. Tetracycline-regulatable gene expression is also available in both the DNA plasmid and lentiviral vector format (See Ogueta et al., Mol. Med. 7(8):569-79 (2001) and Zhu et al., J. Immunol. Meth. 231: 207-22 (2001)) should there be a difficulty in establishing stable cell lines due to cytotoxicity of the produced proteins.

B. Testing Immunogenicity of the APF-IgG Fusion Molecules by Genetic Immunization of Mice Using a "Prime and Boost" Method Immunization of Mice with APF-Ig Immunogens Plasmid DNA encoding APF-IgG fusion proteins previously tested in vitro is used to immunize mice following a prime-boost immunization procedure. (See Zuber, et al., Virology 278:400-11 (2000) and Radaelli et al., Vaccine 21:2061-73 (2003)). Groups of 6-8 week old BALB/c mice (5 mice per group) are immunized three times with individual antigens by intramuscular injection of the quadriceps at a dosage of 50-150 ug plasmid DNA/per mouse every 2-3 weeks. The protein G-affinity purified APF-IgG fusion proteins produced from mammalian cell cultures may be used for boosting immune responses twice at 20 µg/inoculation in a two-four week interval. Blood/serum is collected at 2-week intervals starting at two weeks following initial inoculation as well as at the time of sacrifice in order to monitor the anti-SARS-specific antibody response. Initially, mice are sacrificed four weeks after final boosting and the presence of cell-mediated SARS-specific immune responses are monitored using T lymphocytes isolated from spleen and/or lymph nodes of immunized mice.

The prime-boost protocol is designed to enhance the antibody response since soluble protein antigens, whether secreted by the host cell receiving DNA vaccine or inoculated protein immunogens, is taken up by APC through endocytosis and expected to be mainly presented by MHC class II molecules. Additional protocols for enhancing antibody response may also be tested, including biological adjuvants such as cytokines IL-4 or IL-10 encoded on plasmids (see Piccirillo and Prud'homme, Curr. Pharm. Des. 9:83-94 (2003)), as well as synthetic adjuvants.

Analysis of Immune Responses Induced by Spike-Ig and Membrane-Ig Vaccines

The ability of APF-Ig fusion proteins to elicit humoral immune responses is examined by antibody assays and cell proliferation assays. In addition, cellular immune responses will be monitored for the purpose of accumulating B- and T-cell epitope information for future vaccine design.

(a) Analysis of Humoral Responses.

Antibody assays. Total serum IgG/IgA and specific antibodies to SARS APFs is quantified by ELISA against purified SARS proteins and immune serum is extensively evaluated to determine the immunogenic fitness of the immunizing APF.

In addition, the immunized sera is analyzed for their ability to inhibit SARS virus infection. The specificity of immune sera-mediated inhibition of SARS-CoV is examined initially using the microneutralization assay (see Example 4, supra) both before and after absorption of the serum to the cognate Spike and Membrane antigen to analyze immunologic fitness. The antiviral (neutralizing) activity of the immune animal sera is compared to the convalescent serum from SARS patients.

Analysis of B-cell responses. The number of spleen cells or circulating B cells capable of producing anti-SARS protein-specific IgG antibodies is quantified in vitro two weeks after primary vaccination and four weeks after final boosting using the antibody ELISPOT assay as described by Milligan and Bernstein, Virology 206:234-41 (1995); Kuklin et al., Virology 240:245-53 (1998); and Zuber et al., Virology 278:400-11 (2000)). Human IgG1 molecules that do not contain any APFs are used as a control.

(b) Analysis of Cellular Responses

T cell proliferation assay. The presence of cell-mediated SARS-CoV Spike and Membrane-specific immune responses is first analyzed by in vitro T-cell proliferation assay using T lymphocytes isolated from spleens of mice sacrificed four weeks after final boosting. Briefly, upon depletion of B-cells with Dynabeads Mouse pan B (B220) magnetic beads according to the described protocol (Dynal, Lake Success, N.Y.), splenocytes are cultured in the presence or absence of purified APF-Ig protein immunogen. $^3$H-labeled thymidine is added and thymidine incorporation is measured. (See Zuber et al., Virology 278:400-11 (2000)). PHA or Con A stimulated cells are included as a positive control for cell viability.

Cytokine Assays. The nature of T-cell immune response is further investigated by measuring the level of two type-I cytokines (INF-γ and IL-2) and two type-2 cytokine (IL-4 and IL-10) with specific ELISA kits or by cytokine ELISPOT assay, respectively. The cell-mediated immune responses in mice immunized with various Spike-Ig chimeras are quantified at the cellular level by INF-γ/IL-2 specific ELISPOT for Th1 response and IL4 specific ELISPOT for Th2 response following the protocol by (Gaudulin et al., Proc. Natl. Acad. Sci. USA 96:14031-36 (1999)).

Other Embodiments

Although particular embodiments have been disclosed herein in detail, this has been done by way of example for purposes of illustration only, and is not intended to be limiting with respect to the scope of the appended claims, which follow. In particular, it is contemplated by the inventors that various substitutions, alterations, and modifications may be made to the invention without departing from the spirit and scope of the invention as defined by the claims. Other aspects, advantages, and modifications considered to be within the scope of the following claims. The claims presented are representative of the inventions disclosed herein. Other, unclaimed inventions are also contemplated. Applicants reserve the right to pursue such inventions in later claims.

We claim:

1. A monoclonal antibody which neutralizes SARS-CoV, wherein said monoclonal antibody binds to an epitope on the spike protein (S) of SARS-CoV consisting of amino acids 324 to 503, wherein the antibody neutralizes SARS-CoV, and wherein said monoclonal antibody comprises a heavy chain variable region (VH) comprising the amino acid sequence of SEQ ID NO: 12 and a light chain variable region (VL) comprising the amino acid sequence of SEQ ID NO: 20.

2. A monoclonal antibody which neutralizes SARS-CoV, wherein said monoclonal antibody binds to an epitope on the spike protein (S) of SARS-CoV consisting of amino acids 324 to 503, wherein the antibody neutralizes SARS-CoV, and wherein said monoclonal antibody comprises the amino acid sequences encoded by the nucleotide sequences of SEQ ID NOs: 2, 3, 4, and 5.

3. An scFv antibody which neutralizes SARS-CoV, wherein said scFv antibody binds to an epitope on the spike protein (S) of SARS-CoV consisting of amino acids 324 to 503, wherein said scFv antibody neutralizes SARS-CoV, and wherein said scFv antibody comprises the amino acid sequence encoded by the nucleotide sequence of SEQ ID NO: 1.

4. A monoclonal antibody which neutralizes SARS-CoV, wherein said antibody has a light chain with three CDRs comprising an amino acid sequence selected from the group consisting of the amino acid sequences of RASQVRSNLA (SEQ ID NO:37); DASTAT (SEQ ID NO:38); and QQRSN-WPPT (SEQ ID NO:39), and wherein said antibody has a heavy chain with three CDRs comprising an amino acid sequence selected from the group consisting of the amino acid sequences of AH; VYDNK (SEQ ID NO: 35); and RSYYL (SEQ ID NO:36).

* * * * *

SEQUENCE LISTING

<160> NUMBER OF SEQ ID NOS: 40

<210> SEQ ID NO 1
<211> LENGTH: 717
<212> TYPE: DNA
<213> ORGANISM: Homo sapiens

<400> SEQUENCE: 1

```
gaggtgcagc tggtgcagtc tgggggaggc gtggtccagc ctgggaagtc cctgagactc      60
tcctgtgcag cctctggatt cgccttcagt agttatgcta tgcactgggt ccgccaggct     120
ccaggcaagg ggctggagtg ggtggcagtt atatcatatg atggaagtaa taaatactac     180
gcagactccg tgaagggccg attcaccatc tccagagaca attccaagaa cacgctgtat     240
ctgcaaatga acagcctgag agctgaggac acggctgtgt attactgtgc gagggacagg     300
agctactacc ttgactactg gggccaggga accctggtca ccgtctcctc aggtggcggc     360
ggttccggag gtggtggttc tggcggtggt ggcagcgaaa cgacactcac gcagtctcca     420
gccaccctgt ctttgtctcc aggggaaagg gccaccctct cctgcagggc cagtcagagt     480
gttaggagca acttagcctg gtaccagcag aaacctggcc aggctcccag gcccctcatc     540
tatgatgcat ccaccagggc cactggcatc ccagacaggt tcagtggcag tgggtctggg     600
acagacttca ctctcaccat cagcagactg gagcctgaag attttgcagt ttattactgt     660
cagcagcgta gcaactggcc tccgacgttc ggccaaggga ccaaggtgga agtcaaa       717
```

<210> SEQ ID NO 2
<211> LENGTH: 351
<212> TYPE: DNA
<213> ORGANISM: Homo sapiens

<400> SEQUENCE: 2

```
gaggtgcagc tggtgcagtc tgggggaggc gtggtccagc ctgggaagtc cctgagactc      60
tcctgtgcag cctctggatt cgccttcagt agttatgcta tgcactgggt ccgccaggct     120
ccaggcaagg ggctggagtg ggtggcagtt atatcatatg atggaagtaa taaatactac     180
gcagactccg tgaagggccg attcaccatc tccagagaca attccaagaa cacgctgtat     240
ctgcaaatga acagcctgag agctgaggac acggctgtgt attactgtgc gagggacagg     300
agctactacc ttgactactg gggccaggga accctggtca ccgtctcctc a              351
```

<210> SEQ ID NO 3
<211> LENGTH: 987
<212> TYPE: DNA
<213> ORGANISM: Homo sapiens

<400> SEQUENCE: 3

```
gctagcacca agggcccatc ggtcttcccc ctggcaccct cctccaagag cacctctggg      60
ggcacagcgg ccctgggctg cctggtcaag gactacttcc ccgaaccggt gacggtgtcg     120
tggaactcag gcgccctgac cagcggcgtg cacaccttcc cggctgtcct acagtcctca     180
ggactctact ccctcagcag cgtggtgacc gtgccctcca gcagcttggg cacccagacc     240
tacatctgca acgtgaatca caagcccagc accaaggtgg acaagaaagc agagcccaaa     300
```

```
tcttgtgaca aaactcacac atccccaccg tgcccagcac ctgaactcct ggggggaccg      360
tcagtcttcc tcttcccccc aaaacccaag acaccctca ggatctcccg accccctgag      420
gtcacatgcg tggtggtgga cgtgagccac gaagacctg aggtcaagtt caactggtac      480
gtggacggcg tggaggtgca taatgccaag acaaagccgc gggaggagca gtacagcacg      540
taccgggtgg tcagcgtcct caccgtcctg caccaggact ggctgaatgg caaggagtac      600
aagtgcaagg tctccaacaa agccctccca gcccccatcg agaaaaccat ctccaaagcc      660
aaagggcagc cccgagaacc acaggtgtac accctgcccc catcccggga tgagctgacc      720
aagaaccagg tcagcctgac ctgcctggtc aaaggcttct atcccagcga catcgccgtg      780
gagtgggaga gcaatgggca gccggagaac aactacaaga ccacgcctcc cgtgctggac      840
tccgacggct ccttcttcct ctacagcaag ctcaccgtgg acaagagcag gtggcagcag      900
gggaacgtct tctcatgctc cgtgatgcat gaggctctgc acaaccacta cacgcagaag      960
agcctctccc tgtctccggg taaatga                                          987

<210> SEQ ID NO 4
<211> LENGTH: 318
<212> TYPE: DNA
<213> ORGANISM: Homo sapiens

<400> SEQUENCE: 4
acgacactca cgcagtctcc agccaccctg tctttgtctc caggggaaag ggccaccctc       60
tcctgcaggg ccagtcagag tgttaggagc aacttagcct ggtaccagca gaaacctggc      120
caggctccca ggcccctcat ctatgatgca tccaccaggg ccactggcat cccagacagg      180
ttcagtggca gtgggtctgg gacagacttc actctcacca tcagcagact ggagcctgaa      240
gattttgcag tttattactg tcagcagcgt agcaactggc ctccgacgtt cggccaaggg      300
accaaggtgg aagtcaaa                                                    318

<210> SEQ ID NO 5
<211> LENGTH: 348
<212> TYPE: DNA
<213> ORGANISM: Homo sapiens

<400> SEQUENCE: 5
gatggtacca aggtggaaat caaacgtacg gtggctgcac catctgtctt catcttcccg       60
ccatctgatg agcagttgaa atctggaact gcctctgttg tgtgcctgct gaataacttc      120
tatcccagag aggccaaagt acagtggaag gtggataacg ccctccaatc gggtaactcc      180
caggagagtg tcacagagca ggacagcaag gacagcacct acagcctcag cagcaccctg      240
acgctgagca aagcagacta cgagaaacac aaagtctacg cctgcgaagt cacccatcag      300
ggcctgagct cgcccgtcac aaagagcttc aacaggggag agtgttga                   348

<210> SEQ ID NO 6
<211> LENGTH: 102
<212> TYPE: PRT
<213> ORGANISM: Homo sapiens

<400> SEQUENCE: 6

Gln Val Gln Leu Val Gln Ser Gly Gly Gly Val Pro Gly Ser Leu Arg
 1               5                  10                  15

Leu Ser Cys Ala Ala Ser Gly Phe Thr Phe Ser Ser Tyr Met Ser Trp
             20                  25                  30
```

```
Val Arg Gln Ala Pro Gly Lys Gly Leu Glu Trp Val Ile Ser Gly Ser
        35                  40                  45

Tyr Tyr Ala Asp Ser Val Lys Gly Arg Phe Thr Ile Ser Arg Asp Asn
    50                  55                  60

Ser Lys Asn Thr Leu Tyr Leu Gln Met Asn Ser Leu Arg Ala Glu Asp
65                  70                  75                  80

Thr Ala Val Tyr Tyr Cys Ala Arg Asp Asp Tyr Trp Gly Gln Gly Thr
                85                  90                  95

Leu Val Thr Val Ser Ser
            100
```

<210> SEQ ID NO 7
<211> LENGTH: 116
<212> TYPE: PRT
<213> ORGANISM: Homo sapiens

<400> SEQUENCE: 7

```
Gln Val Gln Leu Val Gln Ser Gly Gly Gly Val Val Gln Pro Gly Arg
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val
        35                  40                  45

Ser Val Ile Tyr Ser Gly Gly Ser Thr Tyr Tyr Ala Asp Ser Val Lys
    50                  55                  60

Gly Arg Phe Thr Ile Ser Arg Asp Asn Ser Lys Asn Thr Leu Tyr Leu
65                  70                  75                  80

Gln Met Asn Ser Leu Arg Ala Glu Asp Thr Ala Val Tyr Tyr Cys Ala
                85                  90                  95

Lys Asp Tyr Gly Glu Gly Phe Asp Tyr Trp Gly Gln Gly Thr Leu Val
                100                 105                 110

Thr Val Ser Ser
        115
```

<210> SEQ ID NO 8
<211> LENGTH: 117
<212> TYPE: PRT
<213> ORGANISM: Homo sapiens

<400> SEQUENCE: 8

```
Glu Val Gln Leu Val Gln Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Gly Val Tyr Tyr Cys
                85                  90                  95

Ala Arg Asp Trp Gly Tyr Ser Phe Gly Asp Trp Gly Gln Gly Thr Leu
                100                 105                 110

Val Thr Val Ser Ser
            115
```

<210> SEQ ID NO 9
<211> LENGTH: 127
<212> TYPE: PRT
<213> ORGANISM: Homo sapiens

<400> SEQUENCE: 9

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Thr Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Gly Tyr Tyr Gly Asp Tyr Ala Trp Gly Tyr Tyr Tyr Tyr
            100                 105                 110

Gly Met Asp Val Trp Gly Gln Gly Thr Leu Val Thr Val Ser Ser
        115                 120                 125

<210> SEQ ID NO 10
<211> LENGTH: 122
<212> TYPE: PRT
<213> ORGANISM: Homo sapiens

<400> SEQUENCE: 10

Gln Val Gln Leu Gln Glu Ser Gly Gly Gly Leu Val Lys Pro Gly Gly
1               5                   10                  15

Ser Leu Arg Leu Ser Cys Ala Ala Ser Gly Phe Thr Phe Ser Asp Tyr
            20                  25                  30

Tyr Met Ser Trp Ile Arg Gln Ala Pro Gly Lys Gly Leu Glu Trp Val
        35                  40                  45

Ser Tyr Ile Ser Ser Ser Gly Ser Thr Ile Tyr Tyr Ala Asp Ser Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Arg Trp Leu Gln Ile Gly Glu Asp Ala Phe Asp Ile Trp
            100                 105                 110

Gly Gln Gly Thr Thr Val Thr Val Ser Ser
        115                 120

<210> SEQ ID NO 11
<211> LENGTH: 116
<212> TYPE: PRT
<213> ORGANISM: Homo sapiens

<400> SEQUENCE: 11

Gln Val Gln Leu Val Gln Ser Gly Gly Gly Leu Ile Gln Pro Gly Gly
1               5                   10                  15

Ser Leu Arg Leu Ser Cys Ala Ala Ser Gly Phe Thr Val Ser Ser Asn
            20                  25                  30

Tyr Met Ser Trp Val Arg Gln Ala Pro Gly Lys Gly Leu Glu Trp Val

-continued

```
                35                   40                 45
Ser Val Ile Tyr Ser Gly Gly Ser Thr Tyr Tyr Ala Asp Ser Val Lys
 50                      55                  60

Gly Arg Phe Thr Ile Ser Arg Asp Asn Ser Lys Asn Thr Leu Tyr Leu
 65                  70                  75                  80

Gln Met Asn Ser Leu Arg Ala Glu Asp Thr Ala Val Tyr Tyr Cys Ala
                 85                  90                  95

Arg Asn Phe Gly Glu Asp Phe Asp Tyr Trp Gly Gln Gly Thr Leu Val
             100                 105                 110

Thr Val Ser Ser
        115

<210> SEQ ID NO 12
<211> LENGTH: 117
<212> TYPE: PRT
<213> ORGANISM: Homo sapiens

<400> SEQUENCE: 12

Glu Val Gln Leu Val Gln Ser Gly Gly Gly Val Val Gln Pro Gly Lys
 1               5                  10                  15

Ser Leu Arg Leu Ser Cys Ala Ala Ser Gly Phe Ala Phe Ser Ser Tyr
                 20                  25                  30

Ala Met His Trp Val Arg Gln Ala Pro Gly Lys Gly Leu Glu Trp Val
             35                  40                  45

Ala Val Ile Ser Tyr Asp Gly Ser Asn Lys Tyr Tyr Ala Asp Ser Val
         50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asp Arg Ser Tyr Tyr Leu Asp Tyr Trp Gly Gln Gly Thr Leu
             100                 105                 110

Val Thr Val Ser Ser
        115

<210> SEQ ID NO 13
<211> LENGTH: 124
<212> TYPE: PRT
<213> ORGANISM: Homo sapiens

<400> SEQUENCE: 13

Gln Val Gln Leu Val Gln Ser Gly Gly Gly Leu Val Gln Pro Gly Gly
 1               5                  10                  15

Ser Leu Arg Leu Ser Cys Ala Ala Ser Gly Phe Thr Phe Ser Ser Ser
                 20                  25                  30

Trp Met Ser Trp Val Arg Gln Ala Pro Gly Lys Gly Leu Glu Trp Val
             35                  40                  45

Ala Tyr Ile Lys Gln Asp Gly Ser Glu Lys Tyr Tyr Val Asp Ser Val
         50                  55                  60

Lys Gly Arg Phe Thr Ile Ser Arg Asp Asn Ala Lys Asn Ser Leu Tyr
 65                  70                  75                  80

Leu Gln Met Asp Ser Leu Arg Ala Glu Asp Thr Ala Val Tyr Tyr Cys
                 85                  90                  95

Ala Arg Asp Gln Gly Trp Gly Trp Asp Gly Thr Glu Tyr Tyr Ser Asp
             100                 105                 110

Tyr Trp Gly Gln Gly Thr Leu Val Thr Val Ser Ser
```

```
            115                 120

<210> SEQ ID NO 14
<211> LENGTH: 123
<212> TYPE: PRT
<213> ORGANISM: Homo sapiens

<400> SEQUENCE: 14

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asp Asp Leu Ser Asp Tyr Gly Glu Trp Leu Gly Pro Asp Tyr
            100                 105                 110

Trp Gly Gln Gly Thr Leu Val Thr Val Ser Ser
        115                 120

<210> SEQ ID NO 15
<211> LENGTH: 81
<212> TYPE: PRT
<213> ORGANISM: Homo sapiens

<400> SEQUENCE: 15

Gln Leu Thr Gln Pro Ser Ser Gly Ser Pro Gly Gln Arg Thr Ile Ser
1               5                   10                  15

Cys Gly Ser Ser Gly Asn Val Ser Trp Tyr Gln Gln Pro Gly Ala Pro
            20                  25                  30

Lys Leu Leu Ile Tyr Arg Pro Ser Gly Val Pro Asp Arg Phe Ser Gly
        35                  40                  45

Ser Lys Ser Gly Thr Ala Ser Leu Thr Ile Ser Gly Leu Gln Glu Asp
    50                  55                  60

Glu Ala Asp Tyr Tyr Cys Val Phe Gly Gly Thr Lys Leu Thr Val Leu
65                  70                  75                  80

Gly

<210> SEQ ID NO 16
<211> LENGTH: 106
<212> TYPE: PRT
<213> ORGANISM: homo sapiens

<400> SEQUENCE: 16

Ile Gln Met Thr Gln Ser Pro Ser Ser Leu Ser Ala Ser Val Gly Asp
1               5                   10                  15

Arg Val Thr Ile Thr Cys Arg Ala Thr Gln Ser Ile Ser Thr His Leu
            20                  25                  30

Asn Trp Tyr Gln Gln Arg Gly Gly Lys Ala Pro Lys Leu Leu Ile Tyr
        35                  40                  45

Gly Ala Ser Thr Leu Glu Ser Gly Val Pro Ser Arg Phe Ser Gly Ser
    50                  55                  60
```

```
Gly Ser Gly Thr Glu Phe Thr Leu Thr Ile Ser Ser Leu Gln Pro Glu
 65                  70                  75                  80

Asp Phe Ala Thr Tyr Tyr Cys Leu Gln His Arg Ser Tyr Pro Trp Thr
                 85                  90                  95

Phe Gly Gln Gly Thr Asn Val Glu Ile Lys
            100                 105

<210> SEQ ID NO 17
<211> LENGTH: 112
<212> TYPE: PRT
<213> ORGANISM: Homo sapiens

<400> SEQUENCE: 17

Ser Tyr Glu Leu Thr Gln Pro Pro Ser Ala Ser Gly Thr Pro Gly Gln
  1               5                  10                  15

Arg Val Thr Ile Ser Cys Ser Gly Ser Ser Ser Ile Gly Ser Glu
             20                  25                  30

Thr Val Asn Trp Tyr Gln Gln Leu Pro Gly Thr Ala Pro Lys Leu Leu
             35                  40                  45

Ile Tyr Ser Asn Asn Gln Arg Pro Ser Gly Val Pro Asp Arg Phe Ser
 50                  55                  60

Gly Ser Lys Ser Gly Thr Ser Ala Ser Leu Ala Ile Ser Gly Leu Gln
 65                  70                  75                  80

Ser Glu Asp Glu Ala Asp Tyr Tyr Cys Thr Ala Trp Asp Thr Leu
                 85                  90                  95

Asn Gly Arg Val Ile Phe Gly Gly Gly Thr Lys Leu Thr Val Leu Gly
            100                 105                 110

<210> SEQ ID NO 18
<211> LENGTH: 111
<212> TYPE: PRT
<213> ORGANISM: Homo sapiens

<400> SEQUENCE: 18

Gln Thr Val Val Thr Gln Glu Pro Ser Phe Ser Val Ser Pro Gly Gly
  1               5                  10                  15

Thr Ile Thr Leu Thr Cys Asp Leu Asn Ser Gly Leu Val Ser Ser Ser
             20                  25                  30

His Tyr Pro Ser Trp Tyr Gln Gln Thr Pro Gly Gln Ala Pro Arg Thr
             35                  40                  45

Leu Ile Tyr Asn Thr Asn Ile Arg Ser Ser Gly Val Pro Asp Arg Phe
 50                  55                  60

Ser Gly Ala Ile Leu Gly Asn Lys Ala Ala Leu Thr Ile Thr Gly Ala
 65                  70                  75                  80

Gln Ala Glu Asp Glu Ser Asp Tyr Tyr Cys Val Leu Tyr Met Gly Ser
                 85                  90                  95

Gly Ile Ser Val Phe Gly Gly Gly Thr Lys Leu Thr Val Leu Gly
            100                 105                 110

<210> SEQ ID NO 19
<211> LENGTH: 111
<212> TYPE: PRT
<213> ORGANISM: Homo sapiens

<400> SEQUENCE: 19

Gln Ser Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Leu Gly Gly His
```

```
                    20                  25                  30

Asn Phe Val Ser Trp Tyr Gln Gln His Pro Gly Lys Ala Pro Lys Leu
                35                  40                  45

Met Ile Tyr Asp Val Phe Asn Arg Pro Ser Gly Val Ser Ser Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Phe Cys Ser Ser Tyr Thr Ile Thr
                85                  90                  95

Asn Ile Val Val Phe Gly Arg Gly Thr Lys Leu Thr Val Leu Gly
                100                 105                 110

<210> SEQ ID NO 20
<211> LENGTH: 106
<212> TYPE: PRT
<213> ORGANISM: Homo sapiens

<400> SEQUENCE: 20

Thr Thr Leu Thr Gln Ser Pro Ala Thr Leu Ser Leu Ser Pro Gly Glu
 1               5                  10                  15

Arg Ala Thr Leu Ser Cys Arg Ala Ser Gln Ser Val Arg Ser Asn Leu
                20                  25                  30

Ala Trp Tyr Gln Gln Lys Pro Gly Gln Ala Pro Arg Pro Leu Ile Tyr
                35                  40                  45

Asp Ala Ser Thr Arg Ala Thr Gly Ile Pro Asp Arg Phe Ser Gly Ser
 50                  55                  60

Gly Ser Gly Thr Asp Phe Thr Leu Thr Ile Ser Arg Leu Glu Pro Glu
 65                  70                  75                  80

Asp Phe Ala Val Tyr Tyr Cys Gln Gln Arg Ser Asn Trp Pro Pro Thr
                85                  90                  95

Phe Gly Gln Gly Thr Lys Val Glu Val Lys
                100                 105

<210> SEQ ID NO 21
<211> LENGTH: 111
<212> TYPE: PRT
<213> ORGANISM: Homo sapiens

<400> SEQUENCE: 21

Gln Ser Ala Leu Thr Gln Pro Ala Ser Val Ser Gly Ser Pro Gly Gln
 1               5                  10                  15

Ser Ile Thr Ile Ser Cys Thr Gly Thr Ser Ser Asp Val Gly Gly Tyr
                20                  25                  30

Asn Tyr Val Ser Trp Tyr Gln Gln His Pro Gly Lys Ala Pro Lys Leu
                35                  40                  45

Met Ile Tyr Asp Val Ser Lys Arg Pro Ser Gly Val Pro Asp Arg Phe
 50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Phe Cys Ser Ser Tyr Thr Ile Thr
                85                  90                  95

Asp Ile Val Val Phe Gly Gly Gly Thr Lys Leu Thr Val Leu Arg
                100                 105                 110

<210> SEQ ID NO 22
<211> LENGTH: 111
<212> TYPE: PRT
```

<213> ORGANISM: Homo sapiens

<400> SEQUENCE: 22

Gln Pro Gly Leu Thr Gln Pro Pro Ser Ala Ser Gly Thr Pro Gly Gln
1               5                   10                  15

Arg Val Thr Ile Ser Cys Ser Gly Ser Arg Ser Asn Ile Gly Gly Asn
            20                  25                  30

Thr Val Asn Trp Tyr Gln His Val Pro Gly Thr Ala Pro Lys Leu Leu
        35                  40                  45

Ile Tyr Ser Asn Asn Gln Arg Pro Ser Gly Val Pro Asp Arg Phe Ser
    50                  55                  60

Gly Ser Lys Ser Gly Thr Ser Ala Ser Leu Ala Ile Ser Gly Leu Arg
65                  70                  75                  80

Ser Glu Asp Glu Ala Glu Tyr Tyr Cys Ala Thr Trp Glu Asp Ser Leu
                85                  90                  95

Ser Gly Tyr Val Phe Gly Pro Gly Thr Lys Val Thr Val Leu Gly
            100                 105                 110

<210> SEQ ID NO 23
<211> LENGTH: 15
<212> TYPE: PRT
<213> ORGANISM: Homo sapiens

<400> SEQUENCE: 23

Arg Thr Met His Pro Ser Asp Glu Phe Leu Pro Leu Gly Met Pro
1               5                   10                  15

<210> SEQ ID NO 24
<211> LENGTH: 15
<212> TYPE: PRT
<213> ORGANISM: Homo sapiens

<400> SEQUENCE: 24

Val Val Pro Leu Gly Arg Cys Val Ser His Pro Ala Ile Cys Ala
1               5                   10                  15

<210> SEQ ID NO 25
<211> LENGTH: 15
<212> TYPE: PRT
<213> ORGANISM: Homo sapiens

<400> SEQUENCE: 25

Ser Val Asp Asp Cys Arg Trp Asn Leu Asn Cys Glu Pro Pro
1               5                   10                  15

<210> SEQ ID NO 26
<211> LENGTH: 13
<212> TYPE: PRT
<213> ORGANISM: Homo sapiens

<400> SEQUENCE: 26

Cys Leu Ser Ala Thr Cys Asp Cys Thr Leu Cys Gly Pro
1               5                   10

<210> SEQ ID NO 27
<211> LENGTH: 15
<212> TYPE: PRT
<213> ORGANISM: Homo sapiens

<400> SEQUENCE: 27

Gly Thr Gly Leu Val Pro Leu Phe Asp Pro Arg Tyr Arg Phe Leu
1               5                   10                  15

<210> SEQ ID NO 28
<211> LENGTH: 15
<212> TYPE: PRT
<213> ORGANISM: Homo sapiens

<400> SEQUENCE: 28

Pro Asn Cys Trp Val Gly Leu Thr Gly Ala His Ser Cys Phe Leu
1               5                   10                  15

<210> SEQ ID NO 29
<211> LENGTH: 14
<212> TYPE: PRT
<213> ORGANISM: Homo sapiens

<400> SEQUENCE: 29

Tyr Gln Ala Asp Cys Leu Met Asn Arg Cys Pro Thr Ala Glu
1               5                   10

<210> SEQ ID NO 30
<211> LENGTH: 669
<212> TYPE: PRT
<213> ORGANISM: Homo sapiens

<400> SEQUENCE: 30

Met Phe Ile Phe Leu Leu Phe Leu Thr Leu Thr Ser Gly Ser Asp Leu
1               5                   10                  15

Asp Arg Cys Thr Thr Phe Asp Asp Val Gln Ala Pro Asn Tyr Thr Gln
                20                  25                  30

His Thr Ser Ser Met Arg Gly Val Tyr Tyr Pro Asp Glu Ile Phe Arg
            35                  40                  45

Ser Asp Thr Leu Tyr Leu Thr Gln Asp Leu Phe Leu Pro Phe Tyr Ser
    50                  55                  60

Asn Val Thr Gly Phe His Thr Ile Asn His Thr Phe Gly Asn Pro Val
65                  70                  75                  80

Ile Pro Phe Lys Asp Gly Ile Tyr Phe Ala Ala Thr Glu Lys Ser Asn
                85                  90                  95

Val Val Arg Gly Trp Val Phe Gly Ser Thr Met Asn Asn Lys Ser Gln
                100                 105                 110

Ser Val Ile Ile Ile Asn Asn Ser Thr Asn Val Val Ile Arg Ala Cys
            115                 120                 125

Asn Phe Glu Leu Cys Asp Asn Pro Phe Phe Ala Val Ser Lys Pro Met
    130                 135                 140

Gly Thr Gln Thr His Thr Met Ile Phe Asp Asn Ala Phe Asn Cys Thr
145                 150                 155                 160

Phe Glu Tyr Ile Ser Asp Ala Phe Ser Leu Asp Val Ser Glu Lys Ser
                165                 170                 175

Gly Asn Phe Lys His Leu Arg Glu Phe Val Phe Lys Asn Lys Asp Gly
                180                 185                 190

Phe Leu Tyr Val Tyr Lys Gly Tyr Gln Pro Ile Asp Val Val Arg Asp
            195                 200                 205

Leu Pro Ser Gly Phe Asn Thr Leu Lys Pro Ile Phe Lys Leu Pro Leu
    210                 215                 220

Gly Ile Asn Ile Thr Asn Phe Arg Ala Ile Leu Thr Ala Phe Ser Pro
225                 230                 235                 240

Ala Gln Asp Ile Trp Gly Thr Ser Ala Ala Ala Tyr Phe Val Gly Tyr
                245                 250                 255

-continued

```
Leu Lys Pro Thr Thr Phe Met Leu Lys Tyr Asp Glu Asn Gly Thr Ile
            260                 265                 270

Thr Asp Ala Val Asp Cys Ser Gln Asn Pro Leu Ala Glu Leu Lys Cys
            275                 280                 285

Ser Val Lys Ser Phe Glu Ile Asp Lys Gly Ile Tyr Gln Thr Ser Asn
            290                 295                 300

Phe Arg Val Val Pro Ser Gly Asp Val Val Arg Phe Pro Asn Ile Thr
305                 310                 315                 320

Asn Leu Cys Pro Phe Gly Glu Val Phe Asn Pro Ser Val Tyr Ala Trp
                325                 330                 335

Glu Arg Lys Lys Ile Ser Asn Cys Val Ala Asp Tyr Ser Val Leu Tyr
            340                 345                 350

Asn Ser Thr Phe Phe Ser Thr Phe Lys Cys Tyr Gly Val Ser Ala Thr
            355                 360                 365

Lys Leu Asn Asp Leu Cys Phe Ser Asn Val Tyr Ala Asp Ser Phe Val
    370                 375                 380

Val Lys Gly Asp Asp Val Arg Gln Ile Ala Pro Gly Gln Thr Gly Val
385                 390                 395                 400

Ile Ala Asp Tyr Asn Tyr Lys Leu Pro Asp Asp Phe Met Gly Cys Val
                405                 410                 415

Leu Ala Trp Asn Thr Arg Asn Ile Asp Ala Thr Ser Thr Gly Asn Tyr
            420                 425                 430

Asn Tyr Lys Tyr Arg Tyr Leu Arg His Gly Lys Leu Arg Pro Phe Glu
        435                 440                 445

Arg Asp Ile Ser Asn Val Pro Phe Ser Pro Asp Gly Lys Pro Cys Thr
    450                 455                 460

Pro Pro Ala Leu Asn Cys Tyr Trp Pro Leu Asn Asp Tyr Gly Phe Tyr
465                 470                 475                 480

Thr Thr Thr Gly Ile Gly Tyr Gln Pro Tyr Arg Val Val Val Leu Ser
                485                 490                 495

Phe Glu Leu Leu Asn Ala Pro Ala Thr Val Cys Gly Pro Lys Leu Ser
            500                 505                 510

Thr Asp Leu Ile Lys Asn Gln Cys Val Asn Phe Asn Phe Asn Gly Leu
            515                 520                 525

Thr Gly Thr Gly Val Leu Thr Pro Ser Ser Lys Arg Phe Gln Pro Phe
    530                 535                 540

Gln Gln Phe Gly Arg Asp Val Ser Asp Phe Thr Asp Ser Val Arg Asp
545                 550                 555                 560

Pro Lys Thr Ser Glu Ile Leu Asp Ile Ser Pro Cys Ala Phe Gly Gly
                565                 570                 575

Val Ser Val Ile Thr Pro Gly Thr Asn Ala Ser Ser Glu Val Ala Val
            580                 585                 590

Leu Tyr Gln Asp Val Asn Cys Thr Asp Val Ser Thr Ala Ile His Ala
            595                 600                 605

Asp Gln Leu Thr Pro Ala Trp Arg Ile Tyr Ser Thr Gly Asn Asn Val
    610                 615                 620

Phe Gln Thr Gln Ala Gly Cys Leu Ile Gly Ala Glu His Val Asp Thr
625                 630                 635                 640

Ser Tyr Glu Cys Asp Ile Pro Ile Gly Ala Gly Ile Cys Ala Ser Tyr
                645                 650                 655

His Thr Val Ser Leu Leu Arg Ser Thr Ser Gln Lys Ser
            660                 665
```

```
<210> SEQ ID NO 31
<211> LENGTH: 20
<212> TYPE: PRT
<213> ORGANISM: Homo sapiens

<400> SEQUENCE: 31

Arg Val Val Val Leu Ser Phe Glu Leu Gly Pro Pro Gly Gly Pro Phe
1               5                   10                  15

Gly Glu Val Phe
            20

<210> SEQ ID NO 32
<211> LENGTH: 14
<212> TYPE: PRT
<213> ORGANISM: Homo sapiens

<400> SEQUENCE: 32

Val Val Val Ser Phe Glu Leu Asn Leu Cys Pro Phe Gly Glu
1               5                   10

<210> SEQ ID NO 33
<211> LENGTH: 11
<212> TYPE: PRT
<213> ORGANISM: Homo sapiens
<220> FEATURE:
<221> NAME/KEY: MISC_FEATURE
<222> LOCATION: (5)..(7)
<223> OTHER INFORMATION: Wherein Xaa is any amino acid.

<400> SEQUENCE: 33

Ser Phe Glu Leu Xaa Xaa Xaa Pro Phe Gly Glu
1               5                   10

<210> SEQ ID NO 34
<211> LENGTH: 13
<212> TYPE: PRT
<213> ORGANISM: Homo sapiens
<220> FEATURE:
<221> NAME/KEY: MISC_FEATURE
<222> LOCATION: (5)..(9)
<223> OTHER INFORMATION: Wherein Xaa is any amino acid.

<400> SEQUENCE: 34

Ser Phe Glu Leu Xaa Xaa Xaa Xaa Xaa Pro Phe Gly Glu
1               5                   10

<210> SEQ ID NO 35
<211> LENGTH: 5
<212> TYPE: PRT
<213> ORGANISM: Homo sapiens

<400> SEQUENCE: 35

Val Tyr Asp Asn Lys
1               5

<210> SEQ ID NO 36
<211> LENGTH: 5
<212> TYPE: PRT
<213> ORGANISM: Homo sapiens

<400> SEQUENCE: 36

Arg Ser Tyr Tyr Leu
1               5

<210> SEQ ID NO 37
<211> LENGTH: 10
```

```
<212> TYPE: PRT
<213> ORGANISM: Homo sapiens

<400> SEQUENCE: 37

Arg Ala Ser Gln Val Arg Ser Asn Leu Ala
1               5                   10

<210> SEQ ID NO 38
<211> LENGTH: 6
<212> TYPE: PRT
<213> ORGANISM: Homo sapiens

<400> SEQUENCE: 38

Asp Ala Ser Thr Ala Thr
1               5

<210> SEQ ID NO 39
<211> LENGTH: 9
<212> TYPE: PRT
<213> ORGANISM: Homo sapiens

<400> SEQUENCE: 39

Gln Gln Arg Ser Asn Trp Pro Pro Thr
1               5

<210> SEQ ID NO 40
<211> LENGTH: 13
<212> TYPE: PRT
<213> ORGANISM: Homo sapiens

<400> SEQUENCE: 40

Cys Leu Ser Ala Thr Cys Asp Cys Thr Leu Cys Gly Pro
1               5                   10
```